United States Patent
Fang et al.

(10) Patent No.: US 11,427,874 B1
(45) Date of Patent: Aug. 30, 2022

(54) METHODS AND SYSTEMS FOR DETECTION OF PROSTATE CANCER BY DNA METHYLATION ANALYSIS

(71) Applicant: Epi One Inc., Brooklyn, NY (US)

(72) Inventors: Fang Fang, New York, NY (US); Neng Yang, New York, NY (US)

(73) Assignee: Epi One Inc., Brooklyn, NY (US)

( * ) Notice: Subject to any disclaimer, the term of this patent is extended or adjusted under 35 U.S.C. 154(b) by 0 days.

(21) Appl. No.: 16/995,180

(22) Filed: Aug. 17, 2020

Related U.S. Application Data

(60) Provisional application No. 62/891,673, filed on Aug. 26, 2019.

(51) Int. Cl.
*C12Q 1/68* (2018.01)
*C12P 19/34* (2006.01)
*C12Q 1/6886* (2018.01)

(52) U.S. Cl.
CPC ...... *C12Q 1/6886* (2013.01); *C12Q 2600/112* (2013.01); *C12Q 2600/154* (2013.01)

(58) Field of Classification Search
None
See application file for complete search history.

(56) References Cited

U.S. PATENT DOCUMENTS

| | | |
|---|---|---|
| 2003/0124600 A1 | 7/2003 | Sidransky |
| 2005/0153316 A1 | 7/2005 | Jeddeloh et al. |
| 2005/0272065 A1 | 12/2005 | Lakey et al. |
| 2006/0051768 A1 | 3/2006 | Hoon et al. |
| 2006/0194208 A1 | 8/2006 | Tetzner et al. |
| 2007/0178506 A1 | 8/2007 | Martienssen et al. |
| 2009/0170088 A1 | 7/2009 | Budiman et al. |
| 2009/0305234 A1 | 12/2009 | Olek et al. |
| 2010/0144836 A1 | 6/2010 | Van Engeland et al. |
| 2012/0122088 A1 | 5/2012 | Zou et al. |
| 2012/0322058 A1 | 12/2012 | Regan et al. |
| 2013/0078626 A1 | 3/2013 | Wasserstrom et al. |
| 2013/0224740 A1 | 8/2013 | Thierry et al. |
| 2014/0057259 A1 | 2/2014 | Allawi et al. |
| 2014/0227700 A1 | 8/2014 | Sledziewski et al. |
| 2014/0322707 A1 | 10/2014 | He et al. |
| 2014/0363815 A1 | 12/2014 | Dahl et al. |
| 2016/0201142 A1 | 7/2016 | Lo et al. |
| 2017/0233820 A1 | 8/2017 | Kottwitz et al. |
| 2018/0100196 A1 | 4/2018 | Yegnasubramanian et al. |

FOREIGN PATENT DOCUMENTS

| | | |
|---|---|---|
| CN | 106795562 A | 5/2017 |
| EP | 1342794 A1 | 9/2003 |
| EP | 1423533 A2 | 6/2004 |
| EP | 2313341 A2 | 4/2011 |
| EP | 2971170 A1 | 1/2016 |
| EP | 3034628 A1 | 6/2016 |
| WO | WO 2005/040399 * | 5/2005 ............... C12Q 1/68 |
| WO | WO-2007018601 A1 | 2/2007 |
| WO | WO-2011070441 A2 | 6/2011 |
| WO | WO-2011101728 A2 | 8/2011 |
| WO | WO-2011132061 A2 | 10/2011 |
| WO | WO-2012070037 A2 | 5/2012 |
| WO | WO 2005/085477 * | 9/2015 ............... C12Q 1/68 |
| WO | WO-2019068082 A1 | 4/2019 |

OTHER PUBLICATIONS

Costello et al. Graded Methylation in the Promoter and Body of the O6-Methylguanine DNA Methyltransferase (MGMT) Gene Correlates with MGMT Expression in Human Glioma Cells (1994) Journal of Biological Chemistry vol. 269, No. 25, pp. 17228-17237 (Year: 1994).*

NCBI Reference Sequence: NM_001276713.2, Dec. 15, 2000) available at https://www.ncbi.nlm.nih.gov/nuccore/NM_001276713.2 ?report=genbank. (Year: 2000).*

Christensen et al. Aging and Environmental Exposures Alter Tissue-Specific DNA Methylation Dependent upon CpG Island Context (2009) PLoS Genetics vol. 5, No. 8, 13 pages (Year: 2009).*

Goni et al The qPCR data statistical analysis Integromics White Paper—Sep. 2009, available at https://gene-quantification.de/integromics-qpcr-statistics-white-paper.pdf (Year: 2009).*

Cheow et al., Multiplexed locus-specific analysis of DNA methylation in single cells (2015) Nature Protocols vol. 10, No. 4 pp. 619-631 (Year: 2015).*

Murat Bioinformatics analysis of epigenetic variants associated with melanoma. Diss. University of Bradford, Jul. 30, 2018, available at https://bradscholars.brad.ac.uk/handle/10454/17220 (Year: 2018).*

* cited by examiner

*Primary Examiner* — Stephen T Kapushoc
(74) *Attorney, Agent, or Firm* — Wilson Sonsini Goodrich & Rosati

(57) ABSTRACT

The present disclosure provides methods and systems directed to detection of prostate cancer. A method for processing or analyzing DNA molecules from a biological sample of a subject may comprise processing (a) providing a first set of DNA fragments derived from a first portion of the DNA molecules upon subjecting the first portion to CpG site fragmentation conditions; (b) providing a second set of DNA fragments derived from a second portion of the DNA molecules, the second portion not subjected to fragmentation conditions; (c) for a genomic region, processing the first and the second sets of DNA fragments or derivatives thereof to yield first and second quantitative measures of DNA methylation; and (d) processing the first quantitative measure with the second quantitative measure to yield a third quantitative measure of DNA methylation at the genomic region, thereby generating a methylation profile of the DNA molecules at the genomic region.

20 Claims, 8 Drawing Sheets
Specification includes a Sequence Listing.

US 11,427,874 B1

METHODS AND SYSTEMS FOR DETECTION OF PROSTATE CANCER BY DNA METHYLATION ANALYSIS

CROSS-REFERENCE

This application claims the benefit of U.S. Provisional Patent Application No. 62/891,673, filed Aug. 26, 2019, which is incorporated by reference herein in its entirety.
INCORPORATION BY REFERENCE OF SEQUENCE LISTING PROVIDED AS A TEXT FILE
A Sequence Listing is provided herewith as a text file, "55223-701_201_SL.txt" created on Feb. 9, 2022, and having a size of 87,479 bytes. The contents of the text file are hereby incorporated by reference herein in their entirety.

BACKGROUND

Prostate cancer is the second most common form of cancer in men worldwide, accounting for about 15% of the cancers diagnosed in men. Currently, the only available blood molecular screening method for prostate cancer is a prostate-specific antigen (PSA) test, which aims to detect prostate cancer at an early stage when the disease is amenable to curative treatment and reduce the overall disease-specific mortality. However, PSA is not a cancer-specific biomarker, and its level often increases abnormally in prostate-benign patients. Further, only a small minority of men with an elevated PSA level are actually found to have prostate cancer when a biopsy is performed. Therefore, there is scant evidence to establish that PSA screening for prostate cancer can save lives. Currently, biopsy is the only method for prostate cancer diagnosis, but high false negative rates of biopsy can leads significant percentages of men remaining undiagnosed after the first biopsy. Further, marker of prostate cancer such as the tumor stage, Gleason score, and PSA level cannot accurately identify the individuals ultimately failing of a treatment. Thus, there is an urgent need to develop high performance assays with panels of good biomarkers for tissue and blood tests to reduce the need for repeated biopsies for prostate cancer diagnosis and to monitor treated patients for recurrence and metastasis.

SUMMARY

The present disclosure provides methods, systems, and kits for detecting prostate cancers by processing nucleic acids from biological samples (e.g., tissue samples and/or bodily fluid samples) obtained from or derived from a subject. Biological samples obtained from subjects may be analyzed to measure a presence, absence, or relative assessment of the prostate cancer. The analysis may be performed at a set of genomic regions, such as a panel of DNA methylation biomarker regions. The subjects may include subjects with prostate cancer (e.g., prostate cancer patients) and subjects without prostate cancer (e.g., normal or healthy controls).

In an aspect, the present disclosure provides a method for processing or analyzing a plurality of deoxyribonucleic (DNA) molecules from a biological sample of a subject, comprising: (a) providing a first set of DNA fragments derived from a first portion of said plurality of DNA molecules upon subjecting said first portion of said plurality of DNA molecules to fragmentation conditions sufficient to fragment at least a subset of said first portion of said plurality of DNA molecules at one or more CpG sites, wherein at least a subset of said first set of DNA fragments comprises methylated nucleic acid bases; (b) providing a second set of DNA fragments derived from a second portion of said plurality of DNA molecules, wherein said second portion of said plurality of DNA molecules is not subjected to fragmentation conditions; (c) for a genomic region, processing (i) said first set of DNA fragments or derivatives thereof to yield a first quantitative measure of DNA methylation and (ii) said second set of DNA fragments or derivatives thereof to yield a second quantitative measure of DNA methylation; and (d) processing said first quantitative measure with said second quantitative measure to yield a third quantitative measure of DNA methylation at said genomic region, thereby generating a methylation profile of said plurality of DNA molecules at said genomic region.

In some embodiments, said biological sample is obtained or derived from a tissue sample, a blood sample, a plasma sample, a serum sample, an exosome sample, a urine sample, a sweat sample, or a saliva sample.

In some embodiments, the method further comprises performing an assay selected from the group consisting of methylation-sensitive restriction enzyme (MSRE) digestion, polymerase chain reaction (PCR), quantitative PCR (qPCR), nucleic acid sequencing, target capture, mass spectrometry-based target fragmentation assay, flap endonuclease-based assay, CRISPR-based assay, methylation-specific assay comprising bisulfite treatment, methylation-specific PCR, targeted sequencing, targeted bisulfite sequencing, pyrosequencing, mass spectroscopy-based bisulfite sequencing (EpiTYPER), reduced representation bisulfite sequence (RRBS), whole genome sequencing (WGS), and a combination thereof.

In some embodiments, said fragmentation conditions comprise MSRE digestion of said first portion of said plurality of DNA molecules to fragment said at least said subset of said first portion of said plurality of DNA molecules at said one or more CpG sites. In some embodiments, said MSRE is selected from the group consisting of AatII, Acc65I, AccI, Acil, ACII, Afel, Agel, Apal, ApaLI, AscI, AsiSI, Aval, AvaII, Aox I, BaeI, BanI, BbeI, BceAI, BegI, BfuCI, BglI, BisI, BisI, BmgBI, BsaAI, BsaBI, BsaHI, BsaI, BseYI, BsiEI, BsiWI, BslI, BsmAI, BsmBI, BsmFI, BspDI, BsrBI, BsrFI, BssHII, BssKI, BstAPI, BstBI, BstUI, BstZ17I, Cac8I, ClaI, DpnI, DrdI, EaeI, EagI, Eagl-IF, EciI, EcoRI, EcoRI-HF, FauI, Fnu4HI, FseI, FspI, Gla I, Glu I, HaeII, HgaI, HhaI, HincII, HincII, Hinfl, HinPlI, HpaI, HpaII, Hpyl66ii, Hpyl88iii, Hpy99I, HpyCH4IV, KasI, Kro I, Mal I, MluI, MmeI, MspAII, Mte I, MwoI, NaeI, NacI, NgoNIV, Nhe-HFI, NheI, NlaIV, NotI, NotI-HF, NruI, Nt.BbvCI, Nt.BsmAI, Nt.CviPII, PaeR7I, PleI, PmeI, PmlI, Pcs I, Pkr I, PshAI, PspOMI, PvuI, RsaI, RsrII, SacII, SalI, SalI-HF, Sau3AI, Sau96I, ScrFI, SfiI, SfoI, SgrAI, Smal, SnaBI, TfiI, TscI, TseI, TspMI, and ZraI.

In some embodiments, processing said first set of DNA fragments or derivatives thereof in (c) (i) comprises subjecting said first set of DNA fragments or derivatives thereof to amplification, and wherein processing said second set of DNA fragments or derivatives thereof in (c) (ii) comprises subjecting said second set of DNA fragments or derivatives thereof to said amplification. In some embodiments, said amplification comprises targeted quantitative polymerase chain reaction (qPCR) at said genomic region. In some embodiments, processing said first set of DNA fragments or derivatives thereof in (c) (i) comprises determining a first cycle threshold (Ct) value for said amplification of said first set of DNA fragments or derivatives thereof at said genomic region, and wherein processing said second set of DNA fragments or derivatives thereof in (c) (ii) comprises determining a second cycle threshold (Ct) value for said amplification of said second set of DNA fragments or derivatives thereof at said genomic region. In some embodiments, (c) comprises determining a reference Ct value for said amplification of said first set of DNA fragments or derivatives thereof and said second set of DNA fragments or derivatives thereof at a reference genomic region, and normalizing said first quantitative measure and said second quantitative measure using said reference Ct value. In some embodiments, said normalizing comprises subtracting said reference Ct value from said first quantitative measure and said second quantitative measure. In some embodiments, processing said first quantitative measure with said second quantitative measure in (d) comprises calculating an intensity ratio of said first quantitative measure and said second quantitative measure at said genomic region. In some embodiments, calculating said intensity ratio comprises determining a difference between said first quantitative measure and said second quantitative measure at said genomic region. In some embodiments, calculating said intensity ratio comprises determining an exponentiation of a base value and said determined difference at said genomic region. In some embodiments, said base value is 2. In some embodiments, calculating said intensity ratio comprises determining a reciprocal of said determined exponentiation at said genomic region.

In some embodiments, the method further comprises subjecting said first set of DNA fragments and said second set of DNA fragments, or derivatives thereof, to conditions sufficient to permit said methylated nucleic acid bases to be distinguished from unmethylated nucleic acid bases. In some embodiments, subjecting said first set of DNA fragments and said second set of DNA fragments, or derivatives thereof, to said conditions comprises performing bisulfite treatment on first set of DNA fragments and said second set of DNA fragments, or derivatives thereof.

In some embodiments, the method further comprises processing said methylation profile with one or more reference methylation profiles. In some embodiments, said one or more reference methylation profiles are obtained from reference biological samples of one or more additional subjects. In some embodiments, said one or more additional subjects comprise healthy subjects. In some embodiments, said one or more additional subjects comprise subjects having a disease or disorder. In some embodiments, said disease or disorder is a cancer. In some embodiments, said disease or disorder is a cancer selected from the group consisting of pancreatic cancer, liver cancer, lung cancer, colorectal cancer, leukemia, bladder cancer, bone cancer, brain cancer, breast cancer, cervical cancer, endometrial cancer, esophageal cancer, gastric cancer, head and neck cancer, melanoma, ovarian cancer, and prostate cancer. In some embodiments, said cancer is prostate cancer.

In some embodiments, said genomic region comprises one or more CpG sites. In some embodiments, said genomic region comprises a plurality of CpG sites. In some embodiments, said plurality of CpG sites comprises at least about 10 CpG sites.

In some embodiments, said genomic region comprises one or more genes selected from the group consisting of SCGB3A1, ANKDD1B, C5orf49, C9orf3, and GPR75-ASB3. In some embodiments, said genomic region is selected from Table 1, Table 2, or SEQ ID NO:1-SEQ ID NO:276. In some embodiments, said genomic region comprises at least about 10, at least about 20, at least about 30, at least about 40, at least about 50, at least about 60, at least about 70, at least about 80, at least about 90, at least about 100, at least about 120, at least about 140, at least about 160, at least about 180, at least about 200, at least about 220, at least about 240, or at least about 260 distinct genomic regions selected from Table 1, Table 2, or SEQ ID NO:1-SEQ ID NO:276. In some embodiments, said genomic region is selected from Table 2.

In some embodiments, the method further comprises electronically outputting a report indicative of said methylation profile. In some embodiments, the method further comprises processing said methylation profile to generate a likelihood of said subject as having or being suspected of having a disease or disorder. In some embodiments, said disease or disorder is a cancer. In some embodiments, said disease or disorder is a cancer selected from the group consisting of pancreatic cancer, liver cancer, lung cancer, colorectal cancer, leukemia, bladder cancer, bone cancer, brain cancer, breast cancer, cervical cancer, endometrial cancer, esophageal cancer, gastric cancer, head and neck cancer, melanoma, ovarian cancer, and prostate cancer. In some embodiments, said cancer is prostate cancer.

In some embodiments, said likelihood is generated with a sensitivity of at least about 80%. In some embodiments, said likelihood is generated with a sensitivity of at least about 90%. In some embodiments, said likelihood is generated with a specificity of at least about 90%. In some embodiments, said likelihood is generated with a specificity of at least about 95%. In some embodiments, said likelihood is generated with an accuracy of at least about 90%. In some embodiments, said likelihood is generated with an accuracy of at least about 95%. In some embodiments, said likelihood is generated with an area under the curve (AUC) of at least about 0.90.

In some embodiments, said first set of DNA fragments and said second set of DNA fragments each comprises a first amount of external DNA molecules, wherein said external DNA molecules do not contain CpG sites.

In another aspect, the present disclosure provides a method for processing or analyzing a plurality of deoxyribonucleic (DNA) molecules from a biological sample of a subject, comprising: (a) providing a first set of DNA fragments derived from a first portion of said plurality of DNA molecules upon subjecting said first portion of said plurality of DNA molecules to fragmentation conditions sufficient to fragment at least a subset of said first portion of said plurality of DNA molecules at one or more CpG sites, wherein at least a subset of said first set of DNA fragments comprises methylated nucleic acid bases; (b) providing a second set of DNA fragments derived from a second portion of said plurality of DNA molecules, wherein said second portion has a substantially equal amount of DNA as said first portion; (c) for a genomic region, processing (i) said first set of DNA fragments or derivatives thereof to yield a first quantitative measure of DNA methylation and (ii) said second set of DNA fragments or derivatives thereof to yield a second quantitative measure of DNA methylation; and (d) processing said first quantitative measure with said second quantitative measure to yield a third quantitative measure of DNA methylation at said genomic region, thereby generating a methylation profile of said plurality of DNA molecules at said genomic region.

In some embodiments, said biological sample is obtained or derived from a tissue sample, a blood sample, a plasma sample, a serum sample, an exosome sample, a urine sample, a sweat sample, or a saliva sample.

In some embodiments, the method further comprises performing an assay selected from the group consisting of methylation-sensitive restriction enzyme (MSRE) digestion, polymerase chain reaction (PCR), quantitative PCR (qPCR), nucleic acid sequencing, target capture, mass spectrometry-based target fragmentation assay, flap endonuclease-based assay, CRISPR-based assay, methylation-specific assay comprising bisulfite treatment, methylation-specific PCR, targeted sequencing, targeted bisulfite sequencing, pyrosequencing, mass spectroscopy-based bisulfite sequencing (EpiTYPER), reduced representation bisulfite sequence (RRBS), whole genome sequencing (WGS), and a combination thereof.

In some embodiments, said fragmentation conditions comprise MSRE digestion of said first portion of said plurality of DNA molecules to fragment said at least said subset of said first portion of said plurality of DNA molecules at said one or more CpG sites. In some embodiments, said MSRE is selected from the group consisting of AatII, Acc65I, AccI, AciI, ACII, AfeI, AgeI, ApaI, ApaLI, AscI, AsiSI, AvaI, AvaII, Aox I, BaeI, BanI, BbeI, BceAI, BcgI, BfuCI, BglI, BisI, BlsI, BmgBI, BsaAI, BsaBI, BsaHI, BsaI, BseYI, BsiEI, BsiWI, BslI, BsmAI, BsmBI, BsmFI, BspDI, BsrBI, BsrFI, BssHII, BssKI, BstAPI, BstBI, BstUI, BstZ17I, Cac8I, ClaI, DpnI, DrdI, EaeI, EagI, Eagl-IF, EciI, EcoRI, EcoRI-HF, FauI, Fnu4HI, FseI, FspI, Gla I, Glu 1, HaeII, HgaI, HhaI, HincII, HincII, Hinfl, HinPII, HpaI, HpaII, Hpyl66ii, Hpyl88iii, Hpy99I, HpyCH4IV, KasI, Kro I, Mal I, MluI, MmeI, MspAII, Mte I, MwoI, NaeI, NacI, NgoNIV, Nhe-HFI, NheI, NlaIV, NotI, NotI-HF, NruI, Nt.BbvCI, Nt.BsmAI, Nt.CviPII, PaeR7I, PleI, PmeI, PmlI, Pcs I, Pkr I, PshAI, PspOMI, PvuI, RsaI, RsrII, SacII, SalI, SalI-HF, Sau3AI, Sau96I, ScrFI, SfiI, SfoI, SgrAI, SmaI, SnaBI, TfiI, TscI, TseI, TspMI, and ZraI.

In some embodiments, processing said first set of DNA fragments or derivatives thereof in (c) (i) comprises subjecting said first set of DNA fragments or derivatives thereof to amplification, and wherein processing said second set of DNA fragments or derivatives thereof in (c) (ii) comprises subjecting said second set of DNA fragments or derivatives thereof to said amplification. In some embodiments, said amplification comprises targeted quantitative polymerase chain reaction (qPCR) at said genomic region. In some embodiments, processing said first set of DNA fragments or derivatives thereof in (c) (i) comprises determining a first cycle threshold (Ct) value for said amplification of said first set of DNA fragments or derivatives thereof at said genomic region, and wherein processing said second set of DNA fragments or derivatives thereof in (c) (ii) comprises determining a second cycle threshold (Ct) value for said amplification of said second set of DNA fragments or derivatives thereof at said genomic region. In some embodiments, (c) comprises determining a reference Ct value for said amplification of said first set of DNA fragments or derivatives thereof and said second set of DNA fragments or derivatives thereof at a reference genomic region, and normalizing said first quantitative measure and said second quantitative measure using said reference Ct value. In some embodiments, said normalizing comprises subtracting said reference Ct value from said first quantitative measure and said second quantitative measure. In some embodiments, processing said first quantitative measure with said second quantitative measure in (d) comprises calculating an intensity ratio of said first quantitative measure and said second quantitative measure at said genomic region. In some embodiments, calculating said intensity ratio comprises determining a difference between said first quantitative measure and said second quantitative measure at said genomic region. In some embodiments, calculating said intensity ratio comprises determining an exponentiation of a base value and said determined difference at said genomic region. In some embodiments, said base value is 2. In some embodiments, calculating said intensity ratio comprises determining a reciprocal of said determined exponentiation at said genomic region.

In some embodiments, the method further comprises subjecting said first set of DNA fragments and said second set of DNA fragments, or derivatives thereof, to conditions sufficient to permit said methylated nucleic acid bases to be distinguished from unmethylated nucleic acid bases. In some embodiments, subjecting said first set of DNA fragments and said second set of DNA fragments, or derivatives thereof, to said conditions comprises performing bisulfite treatment on first set of DNA fragments and said second set of DNA fragments, or derivatives thereof.

In some embodiments, the method further comprises processing said methylation profile with one or more reference methylation profiles. In some embodiments, said one or more reference methylation profiles are obtained from reference biological samples of one or more additional subjects. In some embodiments, said one or more additional subjects comprise healthy subjects. In some embodiments, said one or more additional subjects comprise subjects having a disease or disorder. In some embodiments, said disease or disorder is a cancer. In some embodiments, said disease or disorder is a cancer selected from the group consisting of pancreatic cancer, liver cancer, lung cancer, colorectal cancer, leukemia, bladder cancer, bone cancer, brain cancer, breast cancer, cervical cancer, endometrial cancer, esophageal cancer, gastric cancer, head and neck cancer, melanoma, ovarian cancer, and prostate cancer. In some embodiments, said cancer is prostate cancer.

In some embodiments, said genomic region comprises one or more CpG sites. In some embodiments, said genomic region comprises a plurality of CpG sites. In some embodiments, said plurality of CpG sites comprises at least about 10 CpG sites.

In some embodiments, said genomic region comprises one or more genes selected from the group consisting of SCGB3A1, ANKDDIB, C5orf49, C9orf3, and GPR75-ASB3. In some embodiments, said genomic region is selected from Table 1, Table 2, or SEQ ID NO:1-SEQ ID NO:276. In some embodiments, said genomic region comprises at least about 10, at least about 20, at least about 30, at least about 40, at least about 50, at least about 60, at least about 70, at least about 80, at least about 90, at least about 100, at least about 120, at least about 140, at least about 160, at least about 180, at least about 200, at least about 220, at least about 240, or at least about 260 distinct genomic regions selected from Table 1, Table 2, or SEQ ID NO:1-SEQ ID NO:276. In some embodiments, said genomic region is selected from Table 2.

In some embodiments, the method further comprises electronically outputting a report indicative of said methylation profile. In some embodiments, the method further comprises processing said methylation profile to generate a likelihood of said subject as having or being suspected of having a disease or disorder. In some embodiments, said disease or disorder is a cancer. In some embodiments, said disease or disorder is a cancer selected from the group consisting of pancreatic cancer, liver cancer, lung cancer, colorectal cancer, leukemia, bladder cancer, bone cancer, brain cancer, breast cancer, cervical cancer, endometrial cancer, esophageal cancer, gastric cancer, head and neck cancer, melanoma, ovarian cancer, and prostate cancer. In some embodiments, said cancer is prostate cancer.

In some embodiments, said first set of DNA fragments and said second set of DNA fragments each comprises a first amount of external DNA molecules, wherein said external DNA molecules do not contain CpG sites.

In another aspect, the present disclosure provides a method for identifying prostate cancer of a subject, comprising: (a) using a methylation assay to process a plurality of deoxyribonucleic acid (DNA) molecules from a biological sample of the subject to determine quantitative measures of methylation at each of one or more genes, thereby generating a DNA methylation signature of said biological sample of said subject, wherein said one or more genes comprise genes selected from the group consisting of SCGB3A1, ANKDD1B, C5orf49, C9orf3, and GPR75-ASB3; (b) comparing said DNA methylation signature with one or more reference DNA methylation signatures; and (c) based at least in part on the comparing in (b), identifying the prostate cancer of said subject.

In some embodiments, said biological sample is obtained or derived from a tissue sample, a blood sample, or a urine sample.

In some embodiments, said methylation assay comprises one or more assays selected from the group consisting of: methylation-sensitive restriction enzyme (MSRE) digestion, polymerase chain reaction (PCR), quantitative PCR (qPCR), nucleic acid sequencing, target capture, mass spectrometry-based target fragmentation assay, flap endonuclease-based assay, CRISPR-based assay, methylation-specific assay comprising bisulfite treatment, methylation-specific PCR, targeted sequencing, targeted bisulfite sequencing, pyrosequencing, mass spectroscopy-based bisulfite sequencing (EpiTYPER), reduced representation bisulfite sequence (RRBS), whole genome sequencing (WGS), and a combination thereof.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
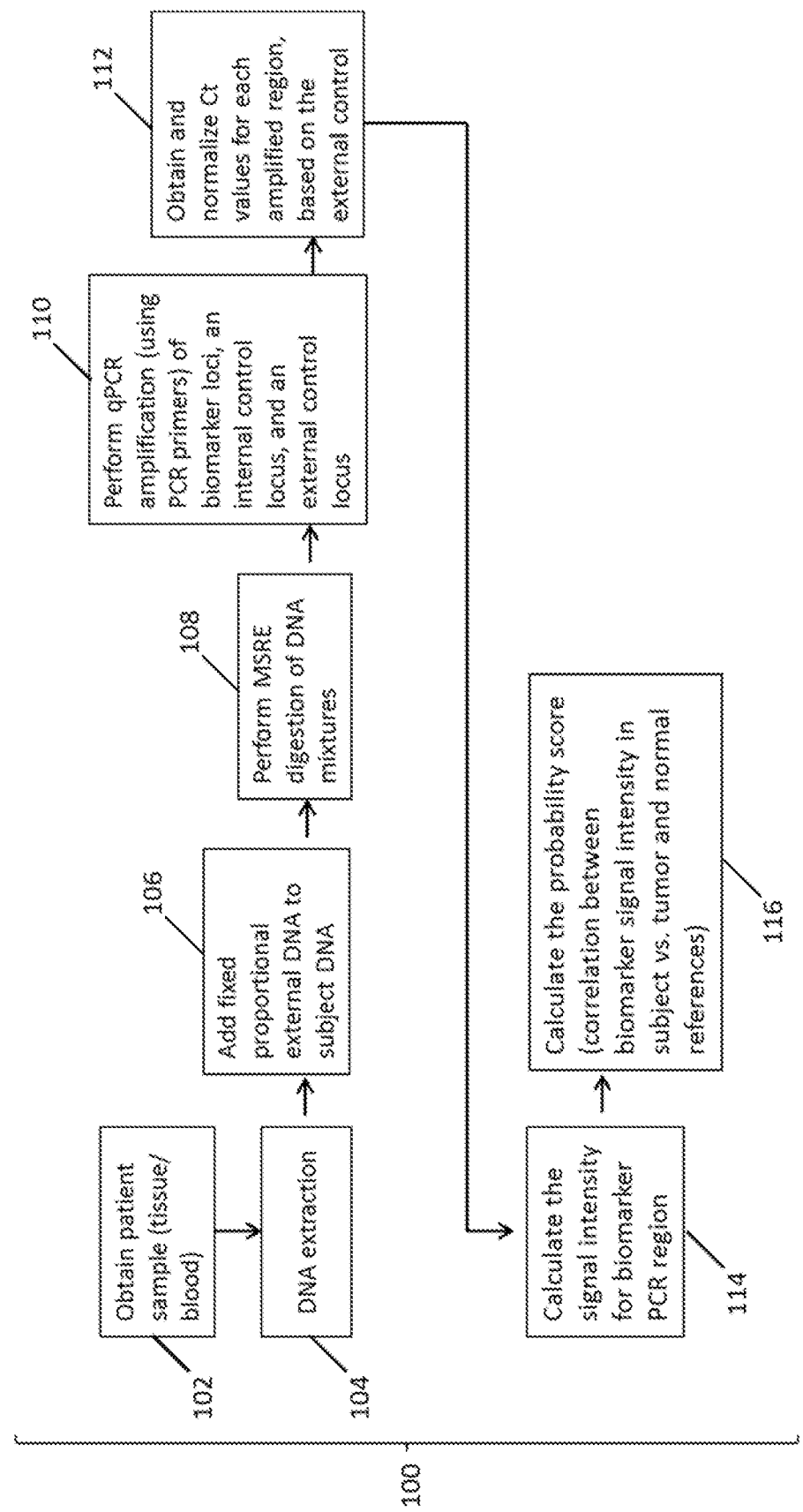
FIG. 1 illustrates a flow-chart for a method 100 of prostate cancer identification in a subject, in accordance with disclosed embodiments.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used in the specification and claims, the singular form "a," "an," and "the" include plural references unless the context clearly dictates otherwise. For example, the term "a nucleic acid" includes a plurality of nucleic acids, including mixtures thereof.

As used herein, the term "nucleic acid" generally refers to a polymeric form of nucleotides of any length, either deoxyribonucleotides (dNTPs) or ribonucleotides (rNTPs), or analogs thereof. Nucleic acids may have any three-dimensional structure, and may perform any function, known or unknown. Non-limiting examples of nucleic acids include DNA, RNA, coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogs. If present, modifications to the nucleotide structure may be made before or after assembly of the nucleic acid. The sequence of nucleotides of a nucleic acid may be interrupted by non-nucleotide components. A nucleic acid may be further modified after polymerization, such as by conjugation or binding with a reporter agent.

As used herein, the term "target nucleic acid" generally refers to a nucleic acid molecule in a starting population of nucleic acid molecules having a nucleotide sequence whose presence, amount, and/or sequence, or changes in one or more of these, are desired to be determined. A target nucleic acid may be any type of nucleic acid, including DNA, RNA, and analogs thereof. As used herein, a "target ribonucleic acid (RNA)" generally refers to a target nucleic acid that is RNA. As used herein, a "target deoxyribonucleic acid (DNA)" generally refers to a target nucleic acid that is DNA.

As used herein, the term "target" generally refers to a genomic region within a marker gene or marker region. As used herein, the term "reference" generally refers to a sample obtained or derived from a subject who is diagnosed with prostate cancer (prostate cancer patient) or who has received a negative clinical indication of prostate cancer (e.g., a healthy or control subject without prostate cancer).

As used herein, the terms "locus" or "region" are generally interchangeable and refer to a specific genomic region on the genome represented by chromosome number, start position, and end position.

As used herein, the term "subject," generally refers to an entity or a medium that has testable or detectable genetic information. A subject can be a person or individual, such as a patient. A subject can be a vertebrate, such as, for example, a mammal. Non-limiting examples of mammals include murines, simians, humans, farm animals, sport animals, and pets.

As used herein, the term "sample" generally refers to a bodily sample or part(s) of a subject, which is obtained and analyzed to measure or to determine the character of the whole, such as a specimen of tissue, blood, or urine.

As used herein, the term "tumor suppression genes" generally refers to a group of genes directing the production of the protein that regulates cell division. The tumor suppressor protein can play a role in keeping cell division in check. When mutated, a tumor suppressor gene may become unable to control cell division and lead to uncontrolled cell growth, an important mechanism in tumorigenesis.

As used herein, the term "biomarker" generally refers to any substance, structure, or process that can be measured in a subject's body or its products and be used to influence or predict a clinical outcome or disease with or without treatment, select an appropriate treatment (or predict whether treatment would be effective), or monitor a current treatment and potentially change the treatment.

As used herein, the term "methylation" refers to 5-methyl cytosine (5mc) or 5-hydroxymethylcytosine (5hmC), including cytosine residues that are part of the sequence CG, also denoted as CpG dinucleotides (cytosine residues that are part of other sequences are not methylated). Some CG dinucleotides in the human genome are methylated, and others are not. In addition, methylation can be cell-specific and tissue-specific, such that a specific CG dinucleotide can be methylated in a certain cell and at the same time unmethylated in a different cell, or methylated in a certain tissue and at the same time unmethylated in different tissues. DNA methylation can be an important regulator of gene transcription. Aberrant DNA methylation patterns, both hypermethylation and hypomethylation, as compared to normal tissue, may be associated with a large number of human malignancies. In some embodiments, 5hmC residues of a sequence may be subjected to glucosylation prior to subsequent bisulfite treatment and MSRE digestion. For example, the glucosylation may be performed using a glucosyltransferase.

As used herein, the terms "methylation state," "methylation status," and "methylation profile" generally refer to the presence of absence of one or more methylated nucleotide bases in the nucleic acid molecule. For example, a nucleic acid molecule (e.g., DNA molecule) containing a methylated cytosine is considered methylated (e.g., the methylation state of the nucleic acid molecule is methylated). A nucleic acid molecule that does not contain any methylated nucleotides is considered unmethylated.

As used herein, the term "bisulfite treatment" generally refers to the treatment of DNA with bisulfite that converts cytosine residues to uracil residues, but leaves 5-methylcytosine residues unaffected. Therefore, DNA that has been treated with bisulfite may retain only methylated cytosines.

As used herein, the term "pyrosequencing" generally refers to a sequencing-by-synthesis method that quantitatively monitors the real-time incorporation of nucleotides through the enzymatic conversion of released pyrophosphate into a proportional light signal. Analysis of DNA methylation patterns by pyrosequencing may combine a simple reaction protocol with reproducible and accurate measures of the degree of methylation at several CpGs in close proximity with high quantitative resolution. After bisulfite treatment and PCR, the degree of each methylation at each CpG position in a sequence may be determined from the ratio of T and C. The process of purification and sequencing can be repeated for the same template to analyze other CpGs in the same amplification product.

As used herein, the terms "amplifying" and "amplification" are used interchangeably and generally refer to generating one or more copies or "amplified product" of a nucleic acid. The term "DNA amplification" generally refers to generating one or more copies of a DNA molecule or "amplified DNA product." The term "reverse transcription amplification" generally refers to the generation of deoxyribonucleic acid (DNA) from a ribonucleic acid (RNA) template via the action of a reverse transcriptase. Amplification may be performed by polymerase chain reaction (PCR), which is based on using DNA polymerase to synthesize new strands of DNA complementary to the initial template strands.

As used herein, the term "polymerase chain reaction (PCR)" generally refers to a method for increasing the concentration of a segment of a target sequence in a mixture of genomic DNA without cloning or purification. This process for amplifying the target sequence may comprise introducing a large excess of two oligonucleotide primers to the DNA mixture containing the desired target sequence, followed by a precise sequence of thermal cycling in the presence of a DNA polymerase. The two primers may be complementary to their respective strands of the double-stranded target sequence. To perform amplification, the mixture may be denatured and the primers may be annealed to their complementary sequences within the target molecule. Following annealing, the primers may be extended with a polymerase so as to form a new pair of complementary strands. The steps of denaturation, primer annealing, and polymerase extension can be repeated many times (e.g., denaturation, annealing and extension constitute one "cycle"; there can be numerous "cycles") to obtain a high concentration of an amplified segment of the desired target sequence. The length of the amplified segment of the desired target sequence may be determined by the relative positions of the primers with respect to each other, and therefore, this length is a controllable parameter. By virtue of the repeating aspect of the process, the method is referred to as "polymerase chain reaction" (PCR). Because the desired amplified segments of the target sequence become the predominant sequences (in terms of concentration) in the mixture, they are said to be "PCR amplified" and are "PCR products" or "amplicons."

As used herein, the term "DNA template" generally refers to the sample DNA that contains the target sequence. At the beginning of the reaction, high temperature is applied to the original double-stranded DNA molecule to separate the strands from each other.

As used herein, the term "primer" generally refers to a short piece of single-stranded DNA that are complementary to the DNA template. The polymerase begins synthesizing new DNA from the end of the primer.

As used herein, the term "Ct value" generally refers to the number of cycles required for the fluorescent signal to cross a given cycle threshold (e.g., at which the signal exceeds a background level). Ct levels may be inversely proportional to the amount of target nucleic acid in a sample (e.g., the lower the Ct level of a given sample, the greater the amount of target nucleic acid in the sample).

As used herein, the term "restriction enzyme" generally refers to an enzyme that cuts DNA at or near specific recognition nucleotide sequences (e.g., restriction sites).

As used herein, the term "methylation-sensitive" restriction enzyme (MSRE) generally refers to a restriction endonuclease that cleaves its recognition sequence only if it is unmethylated (leaving methylated sites remain intact). The DNA cutting intensity of a "methylation-sensitive" restriction enzyme may depend on the methylation level of the specific sequence, where higher methylation levels lead to less digestion.

As used herein, the term "internal control" generally refers to a sequence from a human genome that does not contain the specific sequences required for methylation-sensitive restriction enzymes to cut.

As used herein, the term "external control" generally refers to a sequence from a non-human genome that does not contain a CG site.

As used herein, the term "methylation-specific PCR (MSP)" generally refers to a tool for qualitative DNA methylation analysis. MSP may have advantages such as ease of design and execution, sensitivity in the ability to detect small quantities of methylated DNA, and the ability to rapidly screen a large number of samples without expensive laboratory equipment. This assay may require modification of the genomic DNA by sodium bisulfite and two independent primer sets for PCR amplification, one pair designed to recognize the methylated versions of the bisulfite-modified sequence and the other pair designed to recognize the unmethylated versions of the bisulfite-modified sequence. The amplicons may be visualized using ethidium bromide staining following agarose gel electrophoresis. Amplicons of the expected size produced from either primer pair may be indicative of the presence of DNA in the original sample with the respective methylation status.

As used herein, the term "reduced representation bisulfite sequencing (RRBS)" generally refers to an efficient and high-throughput technique for analyzing the genome-wide methylation profiles on a single nucleotide level. Reduced representation bisulfite sequencing (RRBS) may combine restriction enzymes and bisulfite sequencing to enrich for areas of the genome with a high CpG content. RRBS can reduce the amount of nucleotides required to sequence to 1% of the genome. The fragments that comprise the reduced genome may still include the majority of promoters, as well as regions such as repeated sequences that are difficult to profile using conventional bisulfite sequencing approaches.

As used herein, the term "targeted (bisulfite) sequencing" generally refers to an accurate, efficient, and economical technology for DNA methylation analysis of target regions, which may include a hybridization-based step on platforms containing pre-designed oligonucleotides (oligos) that capture the CpG islands, gene promoters, and other significant methylated regions, or a PCR-based step to amplify multiple bisulfite-converted DNA regions in a single reaction. Specific primers may be designed to capture the region of interest and evaluate site-specific DNA methylation changes.

As used herein, the term "sensitivity" generally refers to the percentage of a set of samples that report a DNA methylation value above a threshold value that distinguishes between neoplastic (e.g., prostate cancer) and non-neoplastic (e.g., healthy or control) samples. In some embodiments, a positive is defined as a histology-confirmed neoplasia that reports a DNA methylation value above a threshold value (e.g., the range associated with disease), and a false negative is defined as a histology-confirmed neoplasia that reports a DNA methylation value below the threshold value (e.g., the range associated with no disease). The value of sensitivity may reflect the probability that a DNA methylation measurement for a given marker obtained from a diseased sample falls in the range of disease-associated measurements. The clinical relevance of the calculated sensitivity value may represent an estimation of the probability that a given marker can detect or predict the presence of a clinical condition when applied to a subject having the clinical condition.

As used herein, the term "specificity" generally refers to the percentage of non-neoplastic samples that report a DNA methylation value below a threshold value that distinguishes between neoplastic and non-neoplastic samples. In some embodiments, a negative is defined as a histology-confirmed non-neoplastic sample that reports a DNA methylation value below the threshold value (e.g., the range associated with no disease) and a false positive is defined as a histology-confirmed non-neoplastic sample that reports a DNA methylation value above the threshold value (e.g., the range associated with disease). The value of specificity may reflect the probability that a DNA methylation measurement for a given marker obtained from a non-neoplastic (e.g., healthy or control) sample falls in the range of non-disease associated measurements. The clinical relevance of the calculated specificity value may represent an estimation of the probability that a given marker can detect or predict the absence of a clinical condition when applied to a subject not having the clinical condition.

As used herein, the term "AUC" or "AUROC" generally refers to an abbreviation for the area under a Receiver Operating Characteristic (ROC) curve. The ROC curve may be a plot of the true positive rate (TPR) against the false positive rate (FPR) for a plurality of different possible thresholds or cut points of a diagnostic test, thereby illustrating the trade-off between sensitivity and specificity depending on the selected cut point (e.g., any increase in sensitivity is accompanied by a decrease in specificity). The area under an ROC curve (AUC) can be a measure for the accuracy of a diagnostic test (e.g., the larger the area, the more accurate the diagnosis), with an optimal value of 1. In comparison, a random test may have an ROC curve lying on the diagonal with an AUC of 0.5 (e.g., representing a random or worthless test).

Prostate cancer is the second most common form of cancer in men worldwide, accounting for about 15% of the cancers diagnosed in men. Currently, the only available blood molecular screening method for prostate cancer is a prostate-specific antigen (PSA) test, which aims to detect prostate cancer at an early stage when the disease is amenable to curative treatment and reduce the overall disease-specific mortality. However, PSA is not a cancer-specific biomarker, and its level often increases abnormally in prostate-benign patients. Further, only a small minority of men with an elevated PSA level are actually found to have prostate cancer when a biopsy is performed. Therefore, there is scant evidence to establish that PSA screening for prostate cancer can save lives. Currently, biopsy is the only method for prostate cancer diagnosis, but high false negative rates of biopsy can leads significant percentages of men remaining undiagnosed after the first biopsy. Further, marker of prostate cancer such as the tumor stage, Gleason score, and PSA level cannot accurately identify the individuals ultimately failing of a treatment. Thus, there is an urgent need to develop high performance assays with panels of good biomarkers to reduce the need for repeated biopsies for prostate cancer diagnosis and to direct treatment strategies for prostate cancer.

Inactivation of tumor suppression genes is an important event contributing to the development of neoplastic malignancies. The alteration of a gene promoter DNA methylation may be often correlated to gene expression level changes. DNA methylation can occur when DNA methyltransferase adds a methyl group to a DNA molecule at a cytosine-phosphate-guanine (CpG) site without changing the sequence of the DNA molecule. DNA methylation may be an early event during tumorigenesis, and global abnormal DNA methylation may be observed in different tumor types. In general, cancer can be characterized by global hypomethylation (resulting in increased oncogene expression and genomic instability) and by gene-specific promoter hypermethylation resulting in suppressed DNA repair and other tumor-suppressive functions. DNA methylation may be stable in fixed samples over time and may be detectable in various bodily fluids and tissue. DNA methylation may also be cell-type specific. Further, various techniques for measuring DNA methylation can be performed. In light of all these characteristics, DNA methylation may be promising targets for the development of powerful diagnostic, prognostic, and predictive biomarkers for cancers.

The present disclosure provides methods, systems, and kits for detecting prostate cancer in a subject by analyzing nucleic acids from biological samples (e.g., tissue samples and/or bodily fluid samples) obtained from or derived from the subject for abnormal methylation profiles (e.g., relative to reference samples or methylation profiles). Biological samples obtained from subjects may be analyzed to measure a presence, absence, or relative assessment of the prostate cancer. The analysis may be performed at a set of genomic regions, such as DNA methylation marker regions. The subjects may include subjects with prostate cancer (e.g., prostate cancer patients) and subjects without prostate cancer (e.g., normal or healthy controls).

Methods and systems of the present disclosure may use methylation-sensitive restriction enzymes (MSRE) to analyze the methylation status of cytosine residues in CpG sequences. The enzymes may be unable to cleave methylated-cytosine residues and therefore leave methylated DNA intact. In some embodiments, sample DNA obtained or derived from a test subject can be digested with at least one methylation-sensitive restriction enzyme. For example, biomarkers of the present disclosure may include genomic loci that contain at least one specific MSRE recognized sequence (recognition site). The sample DNA can be cut (digested) according to its methylation level, where higher methylation results in less digestion by the enzyme. For example, if a DNA sample from a healthy subject is less methylated than another DNA sample from a cancer patient for the CpGs on the recognition sequence, it will be cut more extensively.

In some embodiments, a control locus is designed to be without MSRE cutting sites. In some embodiments, a fixed proportion of control DNA is added into the sample DNA for all test subjects. In some embodiments, at least one pair of qPCR primers is designed for each target genomic region of a biomarker. For each patient, two qPCR reactions are run independently on the same qPCR target: a first qPCR reaction is run on a first portion of the sample DNA that contains MSRE-digested DNA template, and a second qPCR reaction is run on a second portion of the sample DNA that contains undigested DNA templates. The undigested template may be used to represent the fully methylated DNA. After the purification of the MSRE digestion, the same amount of DNA may be used for the digested and undigested templates. The signal intensity of the qPCR reaction may be generated from the cycle threshold (Ct) values. For each locus of a given subject, the Ct difference (delta Ct) between the first qPCR reaction (run on the digested DNA template) and the second qPCR reaction (run on the undigested DNA template) is calculated and used to indicate the DNA methylation level of the subject. Thus, the delta Ct value can represent the subject's DNA methylation level for the target region. For example, the undigested DNA may have low Ct values, while the digested DNA from a normal individual may have high Ct values, thereby resulting in large absolute delta Ct values. Otherwise, the delta Ct values from a prostate cancer patient may be small (e.g., close to 0).

Using methods and systems of the present disclosure, prostate cancer can be accurately detected using a non user-dependent assay with high sensitivity and specificity in prostate tissue samples. The blood-based assay can use a set of biomarkers that accurately distinguish prostate cancer samples from control samples across all stages of prostate cancer. Further, the blood-based assay may offer high specificity, thereby facilitating the non-invasive application of prostate cancer associated biomarkers for treatment monitoring of prostate cancer patients.

The use of methods, systems, and kits of the present disclosure for prostate cancer detection based on analysis of aberrant methylation profiles (e.g., containing abnormal DNA methylation over a panel of predetermined biomarker genomic regions) may comprise the following steps:

1) Extracting DNA molecules from a biological sample (e.g., tissue, blood, urine, or exosome) of a test subject;

2) Preparing two sub-samples of equal or substantially equal size (e.g., amount and/or volume) obtained or derived from the same subject;

3) Digesting the first sub-sample of the DNA mixture with at least one MSRE to produce DNA fragments, and purifying the digested DNA fragments;

4) Performing qPCR amplification of the digested DNA fragments and the undigested DNA molecules for a panel of one or more target genes (e.g., prostate cancer biomarker genes or biomarker regions) and an internal control locus;

5) Normalizing the cycle threshold (Ct) values by subtracting the control Ct from the target Ct measured for the same subject;

6) Calculating the intensity ratio given by: $1/2^{\wedge(Ct\ of\ normalized\ MSRE\ digested\ DNA-Ct\ of\ normalized\ undigested\ DNA)}$ to produce an intensity ratio of the test sample; and 7) Comparing the intensity ratio of the test sample to the intensity ratio of reference samples obtained or derived from one or more prostate cancer patients and one or more control (e.g., healthy or normal) subjects.

Processing Biological Samples

In an aspect, the present disclosure provides a method for identifying or monitoring prostate cancer in a subject by processing or analyzing DNA molecules from a biological sample of the subject. The method may comprise providing a first set of DNA fragments derived from a first portion of the DNA molecules upon subjecting the first portion to CpG site fragmentation conditions. For example, DNA molecules of a urine sample may be split into two sub-samples, and the first DNA sub-sample may be MSRE-digested to fragment the DNA molecules at CpG sites. The two sub-samples may be of equal or substantially equal size (e.g., amount or volume). Next, the method may comprise providing a second set of DNA fragments derived from a second portion of the DNA molecules, wherein the second portion is not subjected to fragmentation conditions. For example, after the DNA molecules of a urine sample are split into two sub-samples, the second DNA sub-sample may not be subjected to fragmentation conditions such as MSRE digestion. Next, the method may comprise, for a genomic region, processing (i) the first set of DNA fragments or derivatives thereof to yield a first quantitative measure of DNA methylation and (ii) the second set of DNA fragments or derivatives thereof to yield a second quantitative measure of DNA methylation. Next, the method may comprise processing the first quantitative measure with the second quantitative measure to yield a third quantitative measure of DNA methylation at the genomic region, to generate a methylation profile of the plurality of DNA molecules at the genomic region.

FIG. 1 illustrates a flow-chart for a method 100 of prostate cancer identification in a subject, in accordance with disclosed embodiments. The method 100 may comprise obtaining a biological sample (e.g., tissue, blood, and/or urine sample) from a subject (e.g., a patient) (as in operation 102). Next, DNA molecules may be extracted from the biological sample (as in operation 104). Next, at least a first portion of the extracted DNA molecules may be subjected to CpG site fragmentation conditions, such as digestion with methylation-sensitive restriction enzymes (MSREs), while a second portion of the extracted DNA molecules may not be subjected to such fragmentation conditions (as in operation 106). Next, qPCR amplification of at least one biomarker locus, an internal control locus, may be performed (e.g., using qPCR primers) (as in operation 108). Next, cycle threshold (Ct) values may be obtained for each amplified region of a set of genomic regions (e.g., prostate cancer associated biomarkers) and normalized based on the internal control (as in operation 110). Next, a qPCR signal intensity may be calculated for the biomarker region, where the signal intensity=2^[Ct, biomarker restriction locus−Ct, internal control locus] (as in operation 112). Next, a probability score may be calculated, which reflects the correlation between the biomarker signal intensity in the subject and tumor references and/or the correlation between the biomarker signal intensity in the subject and normal references (as in operation 114).

The biological samples may be obtained (as in operation 102) or derived from a tissue sample, a blood sample, a plasma sample, a serum sample, a saliva sample, a sputum sample, a urine sample, a stool sample, a sweat sample, a Pap smear sample, or an exosome sample from a human subject. The biological samples may be stored in a variety of storage conditions before processing, such as different temperatures (e.g., at room temperature, under refrigeration or freezer conditions, at 4° C., at −18° C., −20° C., or at −80° C.) or different preservatives (e.g., alcohol, formaldehyde, or potassium dichromate).

The biological sample may be obtained from a subject with a disease or disorder, from a subject that is suspected of having the disease or disorder, or from a subject that does not have or is not suspected of having the disease or disorder. The disease or disorder may be an infectious disease, an immune disorder or disease, a cancer, a genetic disease, a degenerative disease, a lifestyle disease, an injury, a rare disease or an age related disease. The infectious disease may be caused by bacteria, viruses, fungi, and/or parasites. The cancer may be a prostate cancer. The sample may be taken before and/or after treatment of a subject with a disease or disorder. Samples may be taken before and/or after a treatment. Samples may be taken during a treatment or a treatment regime. Multiple samples may be taken from a subject to monitor the effects of the treatment over time. The sample may be taken from a subject known or suspected of having a prostate cancer for which a definitive positive or negative diagnosis is not available via clinical tests.

The sample may be taken from a subject suspected of having a disease or a disorder. The sample may be taken from a subject experiencing unexplained symptoms, such as fatigue, nausea, weight loss, aches and pains, weakness, or memory loss. The sample may be taken from a subject having explained symptoms. The sample may be taken from a subject at risk of developing a disease or disorder due to factors such as familial history, age, environmental exposure, lifestyle risk factors, or presence of other known risk factors.

After obtaining a biological sample from the subject, the biological sample obtained from the subject may be assayed to generate methylation data indicative of a presence, absence, or relative assessment of a prostate cancer of a subject. For example, a presence, absence, or relative assessment of nucleic acid molecules of the biological sample at a panel of prostate cancer-associated genomic loci (e.g., quantitative measures of methylation at a plurality of prostate cancer-associated genomic loci) may be indicative of prostate cancer of the subject. The biological samples obtained or derived from the subject may be processed by (i) subjecting the biological sample to conditions that are sufficient to isolate, enrich, or extract a plurality of nucleic acid molecules (e.g., DNA molecules), and (ii) assaying the plurality of nucleic acid molecules to generate a methylation profile of the nucleic acid molecules at the panel of prostate cancer-associated genomic loci.

A plurality of nucleic acid molecules may be extracted from the biological sample (as in operation 104) and subjected to further assaying (e.g., sequencing to generate a plurality of sequencing reads). The nucleic acid molecules may comprise deoxyribonucleic acid (DNA) or ribonucleic acid (RNA). The nucleic acid molecules (e.g., DNA or RNA) may be extracted from the biological sample by a variety of methods, such as a FastDNA Kit protocol from MP Biomedicals or a DNeasy Blood & Tissue Kit from QIAGEN. The extraction method may extract all DNA molecules from a sample. Alternatively, the extraction method may selectively extract a portion of DNA molecules from a sample. Extracted RNA molecules from a sample may be converted to DNA molecules by reverse transcription (RT).

The method may comprise a variety of assays suitable for assessing the presence of DNA methylation (e.g., at one or more CpG sites) at the prostate cancer-specific markers in a biological sample. The DNA molecules may be assayed using an assay including, for example, methylation-sensitive restriction enzyme (MSRE) digestion, polymerase chain reaction (PCR), quantitative PCR (qPCR), digital PCR (dPCR), nucleic acid sequencing, target capture, mass spectrometry-based target fragmentation assay, flap endonuclease-based assay, CRISPR-based assay, methylation-specific assay comprising bisulfite treatment, methylation-specific PCR (MSP), COLD-PCR, targeted sequencing, targeted bisulfite sequencing, pyrosequencing, mass spectroscopy-based bisulfite sequencing (EpiTYPER), reduced representation bisulfite sequence (RRBS), whole genome sequencing (WGS), amplification fragment length polymorphism, amplification fragment length polymorphism (AFLP), enzyme-linked immunosorbent assay (ELISA), luminometric methylation assay (LUMA), methyl-sensitive cut counting (MSCC), high-performance liquid chromatograph (HPLC), microarray, bead array, or a combination thereof. For example, the assay may comprise restriction landmark genomic scanning and/or methylation-sensitive restriction enzyme (MSRE) digestion followed by quantitative PCR. The assay may utilize bisulfite treatment of DNA as a step of methylation analysis. After the bisulfite treatment, subsequent steps can include methylation-specific PCR (MSP), targeted sequencing, pyrosquencing, Epityper, reduced representation sequencing, whole genome sequencing, whole genome bisulfite sequencing (WGBS), or a combination thereof. All these methods are prevented from being used to measure DNA methylation of a single/multiple CpG sites in current invented region on the human genome.

In some embodiments, the methylation-sensitive restriction enzyme (MSRE) is selected from the group consisting of AatII, Acc65I, AccI, AciI, ACII, AfeI, AgeI, ApaI, ApaLI, AscI, AsiSI, AvaI, AvaII, Aox I, BaeI, BanI, BbeI, BceAI, BcgI, BfuCI, BglI, BisI, BlsI, BmgBI, BsaAI, BsaBI, BsaHI, BsaI, BseYI, BsiEI, BsiWI, BslI, BsmAI, BsmBI, BsmFI, BspDI, BsrBI, BsrFI, BssHII, BssKI, BstAPI, BstBI, BstUI, BstZ17I, Cac8J, ClaI, DpnI, DrdI, EaeI, EagI, Eagl-IF, EciI, EcoRI, EcoRI-HF, FauI, Fnu4HI, FseI, FspI, Gla I, Glu I, HaeII, HgaI, HhaI, HincII, HincII, HinfI, HinPlI, HpaI, HpaII, Hpyl66ii, Hpyl88iii, Hpy99I, HpyCH4IV, KasI, Kro I, Mal I, MluI, MmeI, MspAlI, Mte I, MwoI, NaeI, NacI, NgoNIV, Nhe-HFI, NheI, NlaIV, NotI, NotI-HF, NruI, Nt.BbvCI, Nt.BsmAI, Nt.CviPII, PaeR7I, PleI, PmeI, PmlI, Pcs I, Pkr I, PshAI, PspOMI, PvuI, RsaI, RsrII, SacII, SalI, SalI-HF, Sau3AI, Sau96I, ScrFI, SfiI, SfoI, SgrAI, SmaI, SnaBI, TfiI, TscI, TseI, TspMI, and ZraI.

The nucleic acid sequencing may be performed by any suitable sequencing methods, such as massively parallel sequencing, paired-end sequencing, high-throughput sequencing, next-generation sequencing (NGS), shotgun sequencing, single-molecule sequencing, nanopore sequencing, semiconductor sequencing, pyrosequencing, sequencing-by-synthesis (SBS), sequencing-by-ligation, and sequencing-by-hybridization, RNA-Seq (Illumina). The sequencing may comprise nucleic acid amplification (e.g., of DNA or RNA molecules). In some embodiments, the nucleic acid amplification is polymerase chain reaction (PCR). A suitable number of rounds of PCR (e.g., PCR, qPCR, reverse-transcriptase PCR, digital PCR, etc.) may be performed to sufficiently amplify an initial amount of nucleic acid (e.g., DNA) to a desired input quantity for subsequent sequencing. In some cases, the PCR may be used for global amplification of nucleic acids. This may comprise using adapter sequences that may be first ligated to different molecules followed by PCR amplification using universal primers. PCR may be performed using any of a number of commercial kits, e.g., provided by Life Technologies, Affymetrix, Promega, Qiagen, etc. In other cases, only certain target nucleic acids within a population of nucleic acids may be amplified (e.g., one or more of the panel of prostate cancer biomarkers or prostate cancer-associated genomic loci). Specific primers, possibly in conjunction with adapter ligation, may be used to selectively amplify certain targets for downstream sequencing. The PCR may comprise targeted amplification of one or more genomic loci, such as genomic loci associated with prostate cancer (e.g., listed in databases such as TCGA or COSMIC). The sequencing may comprise use of simultaneous reverse transcription (RT) and polymerase chain reaction (PCR), such as a OneStep RT-PCR kit protocol by Qiagen, NEB, Thermo Fisher Scientific, or Bio-Rad.

DNA or RNA molecules may be tagged, e.g., with identifiable tags, to allow for multiplexing of a plurality of samples. Any number of DNA or RNA samples may be multiplexed. For example a multiplexed reaction may contain DNA or RNA from at least about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or more than 100 initial samples. For example, a plurality of samples may be tagged with sample barcodes such that each DNA molecule may be traced back to the sample (and the subject) from which the DNA molecule originated. Such tags may be attached to DNA or RNA molecules by ligation or by PCR amplification with primers.

After subjecting the nucleic acid molecules to sequencing, suitable bioinformatics processes may be performed on the sequence reads to generate the methylation data indicative of the presence, absence, or relative assessment of the prostate cancer. For example, the sequence reads may be aligned to one or more reference genomes (e.g., a genome of one or more species such as a human genome). The aligned sequence reads may be quantified at a panel of genomic loci to generate the data indicative of a distribution of the presence, absence, or relative assessment of the prostate cancer. For example, quantification of sequences corresponding to a panel of genomic loci associated with prostate cancer may generate the methylation data indicative of the presence, absence, or relative assessment of the prostate cancer.

The prostate cancer may be identified or monitored in the subject by using probes configured to selectively enrich nucleic acid (e.g., DNA or RNA) molecules corresponding to the panel of genomic loci (e.g., prostate cancer-associated genomic loci). The probes may be nucleic acid primers. The probes may have sequence complementarity with nucleic acid sequences (e.g., about 5 nucleotides, about 10 nucleotides, about 15 nucleotides, about 20 nucleotides, about 25 nucleotides, about 30 nucleotides, about 35 nucleotides, about 40 nucleotides, about 45 nucleotides, about 50 nucleotides, about 55 nucleotides, about 60 nucleotides, about 65 nucleotides, about 70 nucleotides, about 75 nucleotides, about 80 nucleotides, about 85 nucleotides, about 90 nucleotides, about 95 nucleotides, about 100 nucleotides, or more than about 100 nucleotides) from one or more of the individual genomic loci (e.g., prostate cancer-associated genomic loci). The one or more genomic loci (e.g., prostate cancer-associated genomic loci) may comprise 1, 2, 3, 4, 5, 6, 7, 8, 9, 10, about 15, about 20, about 25, about 30, about 35, about 40, about 45, about 50, about 55, about 60, about 65, about 70, about 75, about 80, about 85, about 90, about 95, about 100, or more than about 100 distinct genomic loci (e.g., prostate cancer-associated genomic loci). In some embodiments, the panel of genomic loci comprises one or more prostate cancer-associated genomic loci listed in Table 1.

The biological sample may be processed without any nucleic acid extraction. For example, the processing may comprise assaying the biological sample using probes that are selected for the panel of genomic loci (e.g., prostate cancer-associated genomic loci). The panel of genomic loci (e.g., prostate cancer-associated genomic loci) may comprise 1, 2, 3, 4, 5, 6, 7, 8, 9, 10, about 15, about 20, about 25, about 30, about 35, about 40, about 45, about 50, about 55, about 60, about 65, about 70, about 75, about 80, about 85, about 90, about 95, about 100, or more than about 100 distinct genomic loci (e.g., prostate cancer-associated genomic loci). In some embodiments, the panel of genomic loci comprises one or more prostate cancer-associated genomic loci listed in Table 1.

The processing may comprise assaying the biological sample using probes that are selective for the one or more genomic loci (e.g., prostate cancer-associated genomic loci) among other genomic loci in the biological sample. The probes may be nucleic acid molecules (e.g., DNA or RNA) having sequence complementarity with nucleic acid sequences (e.g., about 5 nucleotides, about 10 nucleotides, about 15 nucleotides, about 20 nucleotides, about 25 nucleotides, about 30 nucleotides, about 35 nucleotides, about 40 nucleotides, about 45 nucleotides, about 50 nucleotides, about 55 nucleotides, about 60 nucleotides, about 65 nucleotides, about 70 nucleotides, about 75 nucleotides, about 80 nucleotides, about 85 nucleotides, about 90 nucleotides, about 95 nucleotides, about 100 nucleotides, or more than about 100 nucleotides) from one or more of the individual genomic loci (e.g., prostate cancer-associated genomic loci). These nucleic acid molecules may be primers or enrichment sequences. The assaying of the biological sample using probes that are selected for the one or more genomic loci (e.g., prostate cancer-associated genomic loci) may comprise use of array hybridization, polymerase chain reaction (PCR), or nucleic acid sequencing (e.g., DNA sequencing or RNA sequencing).

The assay readouts may be quantified at one or more of the panel of genomic loci (e.g., prostate cancer-associated genomic loci) to generate the methylation data indicative of a presence, absence, or relative assessment of the prostate cancer. For example, quantification of array hybridization or polymerase chain reaction (PCR) corresponding to the panel of prostate cancer-associated genomic loci may generate methylation data at the panel of prostate cancer-associated genomic loci in the biological sample. Assay readouts may comprise quantitative PCR (qPCR) values, digital PCR (dPCR) values, digital droplet PCR (ddPCR) values, fluorescence values, etc.

Cycle threshold (Ct) values may be obtained for each amplified region of a set of genomic regions (e.g., prostate cancer associated biomarkers) and normalized based on the external control locus (as in operation 112). For example, a first cycle threshold (Ct) value may be determined for the amplification of a set of digested DNA fragments or derivatives thereof at one or more genomic regions, and a second cycle threshold (Ct) value may be determined for the amplification of a set of undigested DNA molecules or derivatives thereof at the one or more genomic regions. The undigested template may be used to represent the fully methylated DNA. After the purification of the MSRE digestion, the same amount of DNA may be used for the qPCR analysis of the digested and undigested templates. Reference Ct values may be generated based on the external control locus for (i) the amplification of the set of digested DNA fragments or derivatives thereof at the one or more genomic regions, and for (ii) the amplification of the set of undigested DNA molecules or derivatives thereof at the one or more genomic regions. Then, the first Ct value (for amplification of digested DNA) and the second Ct value (for amplification of undigested DNA) can be normalized using the difference of the internal control gene's Ct values before and after the digestion (delta $Ct^c$). The normalization may comprise subtracting the delta $Ct^c$ value from the difference between the first Ct value (for amplification of digested DNA) and the second Ct value (for amplification of undigested DNA).

For each locus of a given subject, the Ct difference (delta Ct) between the first qPCR reaction (run on the digested DNA template) and the second qPCR reaction (run on the undigested DNA template) is calculated and used to indicate the DNA methylation level of the subject. Thus, the delta Ct value can represent the subject's DNA methylation level for the target region. For example, the undigested DNA may have low Ct values, while the digested DNA from a normal individual may have high Ct values, thereby resulting in large absolute delta Ct values. Otherwise, the delta Ct values from a prostate cancer patient may be small (e.g., close to 0).

Next, the qPCR signal intensity may be calculated for the biomarker region from the cycle threshold (Ct) values (as in operation 114). For example, the signal intensity can be given by 2^[Ct, biomarker restriction locus–Ct, internal control locus]. An intensity ratio may be calculated using the first Ct value (for amplification of digested DNA) and the second Ct value (for amplification of undigested DNA), such as by determining the reciprocal of an exponentiation of (i) a base value (e.g., 2, 10, or e) and (ii) a difference between the first Ct value and the second Ct value.

Next, a likelihood (e.g., a probability score) may be calculated, which reflects the correlation between the biomarker signal intensity in the subject and tumor references and/or the correlation between the biomarker signal intensity in the subject and normal references (as in operation 116). Such a likelihood or probability score may be determined using a classifier, as described herein.

Kits

The present disclosure provides kits for identifying or monitoring a prostate cancer in a subject. A kit may comprise probes for identifying a presence, absence, or relative amount of sequences at the panel of prostate cancer-associated genomic loci in a biological sample of the subject, which may be indicative of a prostate cancer. The probes may be selective for the sequences at the panel of prostate cancer-associated genomic loci in the biological sample. A kit may comprise instructions for using the probes to process the biological sample to generate methylation data at the panel of prostate cancer-associated genomic loci in a biological sample of the subject.

The probes in the kit may be selective for the sequences at the plurality of prostate cancer-associated genomic loci in the biological sample. The probes in the kit may be configured to selectively enrich nucleic acid (e.g., DNA or RNA) molecules corresponding to the panel of prostate cancer-associated genomic loci. The probes in the kit may be nucleic acid primers. The probes in the kit may have sequence complementarity with nucleic acid sequences from one or more of the prostate cancer-associated genomic loci. The one or more genomic loci (e.g., prostate cancer-associated genomic loci) may comprise 1, 2, 3, 4, 5, 6, 7, 8, 9, 10, about 15, about 20, about 25, about 30, about 35, about 40, about 45, about 50, about 55, about 60, about 65, about 70, about 75, about 80, about 85, about 90, about 95, about 100, or more than about 100 distinct genomic loci (e.g., prostate cancer-associated genomic loci). In some embodiments, the one or more genomic loci comprise one or more prostate cancer-associated genomic loci listed in Table 1.

The instructions in the kit may comprise instructions to assay the biological sample using the probes that are selective for the sequences at the panel of prostate cancer-associated genomic loci in the biological sample. The probes may be nucleic acid molecules (e.g., DNA or RNA) having sequence complementarity with nucleic acid sequences (e.g., about 5 nucleotides, about 10 nucleotides, about 15 nucleotides, about 20 nucleotides, about 25 nucleotides, about 30 nucleotides, about 35 nucleotides, about 40 nucleotides, about 45 nucleotides, about 50 nucleotides, about 55 nucleotides, about 60 nucleotides, about 65 nucleotides, about 70 nucleotides, about 75 nucleotides, about 80 nucleotides, about 85 nucleotides, about 90 nucleotides, about 95 nucleotides, about 100 nucleotides, or more than about 100 nucleotides) from one or more of the individual genomic loci (e.g., prostate cancer-associated genomic loci). These nucleic acid molecules may be primers or enrichment sequences. The instructions to assay the biological sample may comprise introductions to perform array hybridization, polymerase chain reaction (PCR), or nucleic acid sequencing (e.g., DNA sequencing or RNA sequencing) to process the biological sample to generate methylation data indicative of a presence, absence, or relative amount of sequences at the panel of prostate cancer-associated genomic loci in the biological sample, which may be indicative of a prostate cancer.

The instructions in the kit may comprise instructions to measure and interpret assay readouts, which may be quantified at one or more of the panel of prostate cancer-associated genomic loci to generate the methylation data indicative of a presence, absence, or relative amount of sequences at the panel of prostate cancer-associated genomic loci in the biological sample. For example, quantification of array hybridization or polymerase chain reaction (PCR) corresponding to the panel of prostate cancer-associated genomic loci may generate methylation data at the panel of prostate cancer-associated genomic loci in the biological sample. Assay readouts may comprise quantitative PCR (qPCR) values, digital PCR (dPCR) values, digital droplet PCR (ddPCR) values, fluorescence values, etc., or normalized values thereof.

Classifiers

After processing the biological sample from the subject, a classifier may be used to process the methylation data at the panel of prostate cancer-associated genomic loci to classify the biological sample, thereby identifying or assessing a prostate cancer of the subject. The classifier may be configured to identify the prostate cancer with an accuracy of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more than 99% for at least about 25, at least about 50, at least about 100, at least about 150, at least about 200, at least about 250, at least about 300, at least about 350, at least about 400, at least about 450, at least about 500, or more than about 500 independent samples.

The classifier may comprise a supervised machine learning algorithm or an unsupervised machine learning algorithm. The classifier may comprise a classification and regression tree (CART) algorithm. The classifier may comprise, for example, a support vector machine (SVM), a linear regression, a logistic regression, a nonlinear regression, a neural network, a Random Forest, a deep learning algorithm, a naïve Bayes classifier.

The classifier may be configured to accept a plurality of input variables and to produce one or more output values based on the plurality of input variables. The plurality of input variables may comprise data indicative of a presence, absence, or relative amount of sequences or methylated residues at each of the plurality of prostate cancer-associated genomic loci. For example, an input variable may comprise a number of sequences or methylated residues corresponding to or aligning to each of the plurality of prostate cancer-associated genomic loci.

The classifier may have one or more possible output values, each comprising one of a fixed number of possible values (e.g., a linear classifier, a logistic regression classifier, etc.) indicating a classification of the biological sample by the classifier. The classifier may comprise a binary classifier, such that each of the one or more output values comprises one of two values (e.g., {0, 1}, {positive, negative}, or {cancerous, non-cancerous}) indicating a classification of the biological sample by the classifier. The classifier may be another type of classifier, such that each of the one or more output values comprises one of more than two values (e.g., {0, 1, 2}, {positive, negative, or indeterminate}, or {cancerous, non-cancerous, or indeterminate}) indicating a classification of the biological sample by the classifier. The output values may comprise descriptive labels, numerical values, or a combination thereof. Some of the output values may comprise descriptive labels. Such descriptive labels may provide an identification or indication of the disease state of the subject, and may comprise, for example, positive, negative, cancerous, non-cancerous, or indeterminate. Such descriptive labels may provide an identification of a treatment for the subject's disease state, and may comprise, for example, a therapeutic intervention, a duration of the therapeutic intervention, and/or a dosage of the therapeutic intervention. Such descriptive labels may provide an identification of secondary clinical tests that may be appropriate to perform on the subject, and may comprise, for example, a biopsy, a blood test, a computed tomography (CT) scan, a magnetic resonance imaging (MRI) scan, an ultrasound scan, a chest X-ray, a positron emission tomography (PET) scan, or a PET-CT scan. Such descriptive labels may provide a prognosis of the disease state of the subject. Some descriptive labels may be mapped to numerical values, for example, by mapping "positive" to 1 and "negative" to 0.

Some of the output values may comprise numerical values, such as binary, integer, or continuous values. Such binary output values may comprise, for example, {0, 1}. Such integer output values may comprise, for example, {0, 1, 2}. Such continuous output values may comprise, for example, a probability value of at least 0 and no more than 1. Such continuous output values may comprise, for example, an un-normalized probability value of at least 0. Such continuous output values may comprise, for example, an un-normalized probability value of at least 0. Such continuous output values may indicate a prognosis of the disease or disorder state of the subject and may comprise, for example, an indication of an expected or average progression-free survival (PFS) or overall survival (OS) of the subject. Such continuous output values may indicate a prediction of the course of treatment to treat the disease or disorder state of the subject and may comprise, for example, an indication of an expected duration of efficacy of the course of treatment. Some numerical values may be mapped to descriptive labels, for example, by mapping 1 to "positive" and 0 to "negative."

Some of the output values may be assigned based on one or more cutoff values. For example, a binary classification of samples may assign an output value of "positive" or 1 if the sample indicates that the subject has at least a 50% probability of being diseased. For example, a binary classification of samples may assign an output value of "negative" or 0 if the sample indicates that the subject has less than a 50% probability of being diseased. In this case, a single cutoff value of 50% is used to classify samples into one of the two possible binary output values. Examples of single cutoff values may include about 1%, about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 98%, and about 99%.

As another example, a classification of samples may assign an output value of "positive" or 1 if the sample indicates that the subject has a probability of being diseased of at least 50%, at least about 55%, at least about 60%, at least about 65%, at least about 70%, at least about 75%, at least about 80%, at least about 85%, at least about 90%, at least about 95%, at least about 98%, or at least about 99%. The classification of samples may assign an output value of "positive" or 1 if the sample indicates that the subject has a probability of being diseased of more than 50%, more than 55%, more than 60%, more than 65%, more than 70%, more than 75%, more than 80%, more than 85%, more than 90%, more than 95%, more than 98%, or more than 99%. The classification of samples may assign an output value of "negative" or 0 if the sample indicates that the subject has a probability of being diseased of less than 50%, less than 45%, less than 40%, less than 35%, less than 30%, less than 25%, less than 20%, less than 10%, less than 5%, less than 2%, or less than 1%. The classification of samples may assign an output value of "negative" or 0 if the sample indicates that the subject has a probability of being diseased of no more than 50%, no more than 45%, no more than 40%, no more than 35%, no more than 30%, no more than 25%, no more than 20%, no more than 10%, no more than 5%, no more than 2%, or no more than 1%. The classification of samples may assign an output value of "indeterminate" or 2 if the sample has not been classified as "positive," "negative," 1, or 0. In this case, a set of two cutoff values is used to classify samples into one of the three possible output values. Examples of sets of cutoff values may include {1%, 99%}, {2%, 98%}, {5%, 95%}, {10%, 90%}, {15%, 85%}, {20%, 80%}, {25%, 75%}, {30%, 70%}, {35%, 65%}, {40%, 60%}, and {45%, 55%}. Similarly, sets of n cutoff values may be used to classify samples into one of n+1 possible output values, where n is any positive integer.

The classifier may be trained with a plurality of independent training samples. Each of the independent training samples may comprise a biological sample from a subject, associated data obtained by processing the biological sample (as described elsewhere herein), and one or more known output values corresponding to the biological sample (e.g., a clinical diagnosis, prognosis, treatment efficacy, or absence of a disease or disorder such as a prostate cancer of the subject). Independent training samples may comprise biological samples and associated data and outputs obtained from a plurality of different subjects. Independent training samples may comprise biological samples and associated data and outputs obtained at a plurality of different time points from the same subject (e.g., before, after, and/or during a course of treatment to treat a disease or disorder of the subject). Independent training samples may be associated with presence of the prostate cancer (e.g., training samples comprising biological samples and associated data and outputs obtained from a plurality of subjects known to have the prostate cancer). Independent training samples may be associated with absence of the prostate cancer (e.g., training samples comprising biological samples and associated data and outputs obtained from a plurality of subjects who are known to not have a previous diagnosis of the prostate cancer, or otherwise who are asymptomatic for the prostate cancer).

The classifier may be trained with at least about 50, at least about 100, at least about 150, at least about 200, at least about 250, at least about 300, at least about 350, at least about 400, at least about 450, or at least about 500 independent training samples. The independent training samples may comprise samples associated with presence of the prostate cancer and/or samples associated with absence of the prostate cancer. The classifier may be trained with no more than 500, no more than 450, no more than 400, no more than 350, no more than 300, no more than 250, no more than 200, no more than 150, no more than 100, or no more than 50 independent training samples associated with presence of the prostate cancer. In some embodiments, the biological sample is independent of samples used to train the classifier.

The classifier may be trained with a first number of independent training samples associated with presence of the prostate cancer and a second number of independent training samples associated with absence of the prostate cancer. The first number of independent training samples associated with presence of the prostate cancer may be no more than the second number of independent training samples associated with absence of the prostate cancer. The first number of independent training samples associated with presence of the prostate cancer may be equal to the second number of independent training samples associated with absence of the prostate cancer. The first number of independent training samples associated with presence of the prostate cancer may be greater than the second number of independent training samples associated with absence of the prostate cancer.

The classifier may be configured to identify the prostate cancer with an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more than about 99%, for at least about 50, at least about 100, at least about 150, at least about 200, at least about 250, at least about 300, or more than about 300 independent samples. The accuracy of identifying the prostate cancer by the classifier may be calculated as the percentage of independent test samples (e.g., subjects having the prostate cancer, or apparently healthy subjects with negative clinical test results for the prostate cancer) that are correctly identified or classified as having or not having the prostate cancer, respectively.

The classifier may be configured to identify the prostate cancer with a positive predictive value (PPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more than about 99%. The PPV of identifying the prostate cancer by the classifier may be calculated as the percentage of biological samples identified or classified as having the prostate cancer that correspond to subjects that truly have the prostate cancer. A PPV may also be referred to as a precision.

The classifier may be configured to identify the prostate cancer with a negative predictive value (NPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more than about 99%. The NPV of identifying the prostate cancer by the classifier may be calculated as the percentage of biological samples identified or classified as not having the prostate cancer that correspond to subjects that truly do not have the prostate cancer.

The classifier may be configured to identify the prostate cancer with a clinical sensitivity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more than about 99%. The clinical sensitivity of identifying the prostate cancer by the classifier may be calculated as the percentage of independent test samples associated with presence of the prostate cancer (e.g., subjects known to have the prostate cancer) that are correctly identified or classified as having the prostate cancer. A clinical sensitivity may also be referred to as a recall.

The classifier may be configured to identify the prostate cancer with a clinical specificity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more than about 99%. The clinical specificity of identifying the prostate cancer by the classifier may be calculated as the percentage of independent test samples associated with absence of the prostate cancer (e.g., apparently healthy subjects with negative clinical test results for the prostate cancer) that are correctly identified or classified as not having the prostate cancer.

The classifier may be configured to identify the prostate cancer with an Area-Under-Curve (AUC) of at least about 0.50, at least about 0.55, at least about 0.60, at least about 0.65, at least about 0.70, at least about 0.75, at least about 0.80, at least about 0.81, at least about 0.82, at least about 0.83, at least about 0.84, at least about 0.85, at least about 0.86, at least about 0.87, at least about 0.88, at least about 0.89, at least about 0.90, at least about 0.91, at least about 0.92, at least about 0.93, at least about 0.94, at least about 0.95, at least about 0.96, at least about 0.97, at least about 0.98, at least about 0.99, or more than about 0.99. The AUC may be calculated as an integral of the Receiver Operator Characteristic (ROC) curve (e.g., the area under the ROC curve) associated with the classifier in classifying biological samples as having or not having the prostate cancer.

The classifier may be adjusted or tuned to improve the performance, accuracy, PPV, NPV, clinical sensitivity, clinical specificity, or AUC of identifying the prostate cancer. The classifier may be adjusted or tuned by adjusting parameters of the classifier (e.g., a set of cutoff values used to classify a sample as described elsewhere herein, or weights of a neural network). The classifier may be adjusted or tuned continuously during the training process or after the training process has completed.

After the classifier is initially trained, a subset of the inputs may be identified as most influential or most important to be included for making high-quality classifications. For example, a subset of the plurality of prostate cancer-associated genomic loci may be identified as most influential or most important to be included for making high-quality classifications or identifications of prostate cancer. The plurality of prostate cancer-associated genomic loci or a subset thereof may be ranked based on metrics indicative of each genomic locus's influence or importance toward making high-quality classifications or identifications of prostate cancer. Such metrics may be used to reduce, in some cases significantly, the number of input variables (e.g., predictor variables) that may be used to train the classifier to a desired performance level (e.g., based on a desired minimum accuracy, PPV, NPV, clinical sensitivity, clinical specificity, or AUC). For example, if training the training algorithm with a plurality comprising several dozen or hundreds of input variables in the classifier results in an accuracy of classification of more than 99%, then training the training algorithm instead with only a selected subset of 1, 2, 3, 4, 5, 6, 7, 8, 9, 10, no more than about 10, no more than about 15, no more than about 20, no more than about 25, no more than about 30, no more than about 35, no more than about 40, no more than about 45, no more than about 50, or no more than about 100 such most influential or most important input variables (e.g., marker genes, marker regions, or other genomic loci) among the plurality results in decreased but still acceptable accuracy of classification (e.g., at least about 70%, at least about 75%, at least about 80%, at least about 85%, at least about 90%, at least about 95%, at least about 96%, at least about 97%, or at least about 98%). The subset may be selected by rank-ordering the entire plurality of input variables and selecting a predetermined number (e.g., 1, 2, 3, 4, 5, 6, 7, 8, 9, 10, no more than about 10, no more than about 15, no more than about 20, no more than about 25, no more than about 30, no more than about 35, no more than about 40, no more than about 45, no more than about 50, or no more than about 100) of input variables with the best metrics. In some embodiments, the selected subset of the influential or most important input variables comprises one or more genomic loci listed in Table 2.

Identifying or Monitoring a Prostate Cancer

After using a classifier to process the methylation data at the panel of prostate cancer-associated genomic loci to classify the biological sample, a quantitative measure indicative of the presence, absence, or relative assessment of the prostate cancer may be determined (e.g., likelihood or probability of prostate cancer), and the prostate cancer may be identified or a progression or regression of the prostate cancer may be monitored in the subject based at least in part on the quantitative measure (e.g., likelihood or probability of prostate cancer).

The prostate cancer may be identified in the subject with an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more than about 99%. The accuracy of identifying the prostate cancer by the classifier may be calculated as the percentage of independent test samples (e.g., subjects having the prostate cancer, or apparently healthy subjects with negative clinical test results for the prostate cancer) that are correctly identified or classified as having or not having the prostate cancer, respectively.

The prostate cancer may be identified in the subject with a positive predictive value (PPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more than about 99%. The PPV of identifying the prostate cancer by the classifier may be calculated as the percentage of biological samples identified or classified as having the prostate cancer that correspond to subjects that truly have the prostate cancer. A PPV may also be referred to as a precision.

The prostate cancer may be identified in the subject with a negative predictive value (NPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more than about 99%. The NPV of identifying the prostate cancer by the classifier may be calculated as the percentage of biological samples identified or classified as not having the prostate cancer that correspond to subjects that truly do not have the prostate cancer.

The prostate cancer may be identified in the subject with a clinical sensitivity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more than about 99%. The clinical sensitivity of identifying the prostate cancer by the classifier may be calculated as the percentage of independent test samples associated with presence of the prostate cancer (e.g., subjects having the prostate cancer) that are correctly identified or classified as having the prostate cancer. A clinical sensitivity may also be referred to as a recall.

The prostate cancer may be identified in the subject with a clinical specificity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more than about 99%. The clinical specificity of identifying the prostate cancer by the classifier may be calculated as the percentage of independent test samples associated with absence of the prostate cancer (e.g., apparently healthy subjects with negative clinical test results for the prostate cancer) that are correctly identified or classified as not having the prostate cancer.

After the prostate cancer is identified in a subject, a stage of the prostate cancer (e.g., stage I, stage II, stage III, or stage IV) may further be identified. The stage of the prostate cancer may be determined based at least in part on the methylation data at a panel of prostate cancer-associated genomic loci (e.g., quantitative measures of mutations at the prostate cancer-associated genomic loci).

Upon identifying the subject as having the prostate cancer, the subject may be provided with a therapeutic intervention (e.g., prescribing an appropriate course of treatment to treat the prostate cancer of the subject). The therapeutic intervention may comprise a surgical tumor resection, an effective dose of chemotherapy, an effective dose of radiotherapy, an effective dose of targeted therapy, an effective dose of immunotherapy. If the subject is currently being treated for the prostate cancer with a course of treatment, the therapeutic intervention may comprise a subsequent different course of treatment (e.g., to increase treatment efficacy due to tumor resistance, tumor recurrence, non-response of the current course of treatment).

The therapeutic intervention may comprise recommending the subject for a secondary clinical test to confirm a diagnosis of the prostate cancer. This secondary clinical test may comprise a biopsy, an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof.

The subject may be treated upon identifying the subject as having the prostate cancer. Treating the subject may comprise administering an appropriate therapeutic intervention to treat the prostate cancer of the subject. The therapeutic intervention may comprise a surgical tumor resection, an effective dose of chemotherapy, an effective dose of radiotherapy, an effective dose of targeted therapy, an effective dose of immunotherapy, or any combination thereof. If the subject is currently being treated for the prostate cancer with a course of treatment, the administered therapeutic intervention may comprise a subsequent different course of treatment (e.g., to increase treatment efficacy due to tumor resistance, tumor recurrence, non-response of the current course of treatment).

The methylation data at the panel of prostate cancer-associated genomic loci (e.g., quantitative measures of methylation at the prostate cancer-associated genomic loci) may be assessed over a duration of time to monitor a patient (e.g., subject who has prostate cancer or who is being treated for prostate cancer). In such cases, the quantitative measures of methylation at the prostate cancer-associated genomic loci of the patient may change during the course of treatment. For example, the quantitative measures of methylation at the prostate cancer-associated genomic loci of a patient whose prostate cancer is regressing due to an effective treatment (e.g., chemotherapy or surgical resection) may shift toward the methylation profile or distribution of a healthy subject. Conversely, for example, the quantitative measures of methylation at the prostate cancer-associated genomic loci of a patient whose prostate cancer is progressing due to an ineffective treatment (e.g., when the tumor becomes resistant) may shift toward the methylation profile or distribution of a subject with more advanced stage prostate cancer.

The progression or regression of the prostate cancer in the subject may be monitored by monitoring a course of treatment for treating the prostate cancer in the subject. The monitoring may comprise assessing the prostate cancer in the subject at two or more time points. The assessing may be based at least on the methylation data at a panel of prostate cancer-associated genomic loci (e.g., quantitative measures of methylation at the prostate cancer-associated genomic loci) determined at each of the two or more time points.

A difference in methylation data at a panel of prostate cancer-associated genomic loci (e.g., quantitative measures of methylation at the prostate cancer-associated genomic loci) determined between the two or more time points may be indicative of one or more clinical indications, such as (i) a diagnosis of the prostate cancer in the subject, (ii) a prognosis of the prostate cancer in the subject, (iii) a progression of the prostate cancer in the subject, (iv) a regression of the prostate cancer in the subject, (v) an efficacy of the course of treatment for treating the prostate cancer in the subject, and (vi) a resistance of the prostate cancer toward the course of treatment for treating the prostate cancer in the subject.

A difference in methylation data at a panel of prostate cancer-associated genomic loci (e.g., quantitative measures of methylation at the prostate cancer-associated genomic loci) determined between the two or more time points may be indicative of a diagnosis of the prostate cancer in the subject. For example, if the prostate cancer was not detected in the subject at an earlier time point but was detected in the subject at a later time point, then the difference is indicative of a diagnosis of the prostate cancer in the subject. A clinical action or decision may be made based on this indication of diagnosis of the prostate cancer in the subject, e.g., prescribing a new therapeutic intervention for the subject.

A difference in methylation data at a panel of prostate cancer-associated genomic loci (e.g., quantitative measures of methylation at the prostate cancer-associated genomic loci) determined between the two or more time points may be indicative of a prognosis of the prostate cancer in the subject.

A difference in methylation data at a panel of prostate cancer-associated genomic loci (e.g., quantitative measures of methylation at the prostate cancer-associated genomic loci) determined between the two or more time points may be indicative of a progression of the prostate cancer in the subject. For example, if the prostate cancer was detected in the subject both at an earlier time point and at a later time point, and if the difference is a negative difference (e.g., the presence, absence, or relative assessment of methylation at a panel of prostate cancer-associated genomic loci (e.g., quantitative measures of methylation at the prostate cancer-associated genomic loci) increased from the earlier time point to the later time point), then the difference may be indicative of a progression (e.g., increased tumor load, tumor burden, or tumor size) of the prostate cancer in the subject. A clinical action or decision may be made based on this indication of the progression, e.g., prescribing a new therapeutic intervention or switching therapeutic interventions (e.g., ending a current treatment and prescribing a new treatment) for the subject.

A difference in methylation data at a panel of prostate cancer-associated genomic loci (e.g., quantitative measures of methylation at the prostate cancer-associated genomic loci) determined between the two or more time points may be indicative of a regression of the prostate cancer in the subject. For example, if the prostate cancer was detected in the subject both at an earlier time point and at a later time point, and if the difference is a positive difference (e.g., the presence, absence, or relative assessment of methylation at a panel of prostate cancer-associated genomic loci (e.g., quantitative measures of methylation at the prostate cancer-associated genomic loci) decreased from the earlier time point to the later time point), then the difference may be indicative of a regression (e.g., decreased tumor load, tumor burden, or tumor size) of the prostate cancer in the subject. A clinical action or decision may be made based on this indication of the regression, e.g., continuing or ending a current therapeutic intervention for the subject.

A difference in methylation data at a panel of prostate cancer-associated genomic loci (e.g., quantitative measures of methylation at the prostate cancer-associated genomic loci) determined between the two or more time points may be indicative of an efficacy of the course of treatment for treating the prostate cancer in the subject. For example, if the prostate cancer was detected in the subject at an earlier time point but was not detected in the subject at a later time point, then the difference may be indicative of an efficacy of the course of treatment for treating the prostate cancer in the subject. A clinical action or decision may be made based on this indication of the efficacy of the course of treatment for treating the prostate cancer in the subject, e.g., continuing or ending a current therapeutic intervention for the subject.

A difference in methylation data at a panel of prostate cancer-associated genomic loci (e.g., quantitative measures of methylation at the prostate cancer-associated genomic loci) determined between the two or more time points may be indicative of a resistance of the prostate cancer toward the course of treatment for treating the prostate cancer in the subject. For example, if the prostate cancer was detected in the subject both at an earlier time point and at a later time point, and if the difference is a negative or zero difference (e.g., the presence, absence, or relative assessment of methylation at a panel of prostate cancer-associated genomic loci (e.g., quantitative measures of methylation at the prostate cancer-associated genomic loci) increased or remained at a constant level from the earlier time point to the later time point), and if an efficacious treatment was indicated at an earlier time point, then the difference may be indicative of a resistance (e.g., increased or constant tumor load, tumor burden, or tumor size) of the course of treatment for treating the prostate cancer in the subject. A clinical action or decision may be made based on this indication of the resistance of the course of treatment for treating the prostate cancer in the subject, e.g., ending a current therapeutic intervention and/or switching to (e.g., prescribing) a different new therapeutic intervention for the subject.

Outputting a Report of the Prostate Cancer

After the prostate cancer is identified or a progression or regression of the prostate cancer is monitored in the subject, a report may be electronically outputted that identifies or provides an indication of the identification, prognosis, progression, or regression of the prostate cancer in the subject. The subject may not display a benign or prostate cancer (e.g., is asymptomatic of the benign or prostate cancer). The report may be presented on a graphical user interface (GUI) of an electronic device of a user. The user may be the subject, a caretaker, a physician, a nurse, or another health care worker.

The report may include one or more clinical indications such as (i) a diagnosis of the prostate cancer in the subject, (ii) a prognosis of the prostate cancer in the subject, (iii) a progression of the prostate cancer in the subject, (iv) a regression of the prostate cancer in the subject, (v) an efficacy of the course of treatment for treating the prostate cancer in the subject, and (vi) a resistance of the prostate cancer toward the course of treatment for treating the prostate cancer in the subject. The report may include one or more clinical actions or decisions made based on these one or more clinical indications.

For example, a clinical indication of a diagnosis of the prostate cancer in the subject may be accompanied with a clinical action of prescribing a new therapeutic intervention for the subject. As another example, a clinical indication of a progression of the prostate cancer in the subject may be accompanied with a clinical action of prescribing a new therapeutic intervention or switching therapeutic interventions (e.g., ending a current treatment and prescribing a new treatment) for the subject. As another example, a clinical indication of a regression of the prostate cancer in the subject may be accompanied with a clinical action of continuing or ending a current therapeutic intervention for the subject. As another example, a clinical indication of an efficacy of the course of treatment for treating the prostate cancer in the subject may be accompanied with a clinical action of continuing or ending a current therapeutic intervention for the subject. As another example, a clinical indication of a resistance of the course of treatment for treating the prostate cancer in the subject may be accompanied with a clinical action of ending a current therapeutic intervention and/or switching to (e.g., prescribing) a different new therapeutic intervention for the subject.

Computer Systems

Figure 4:
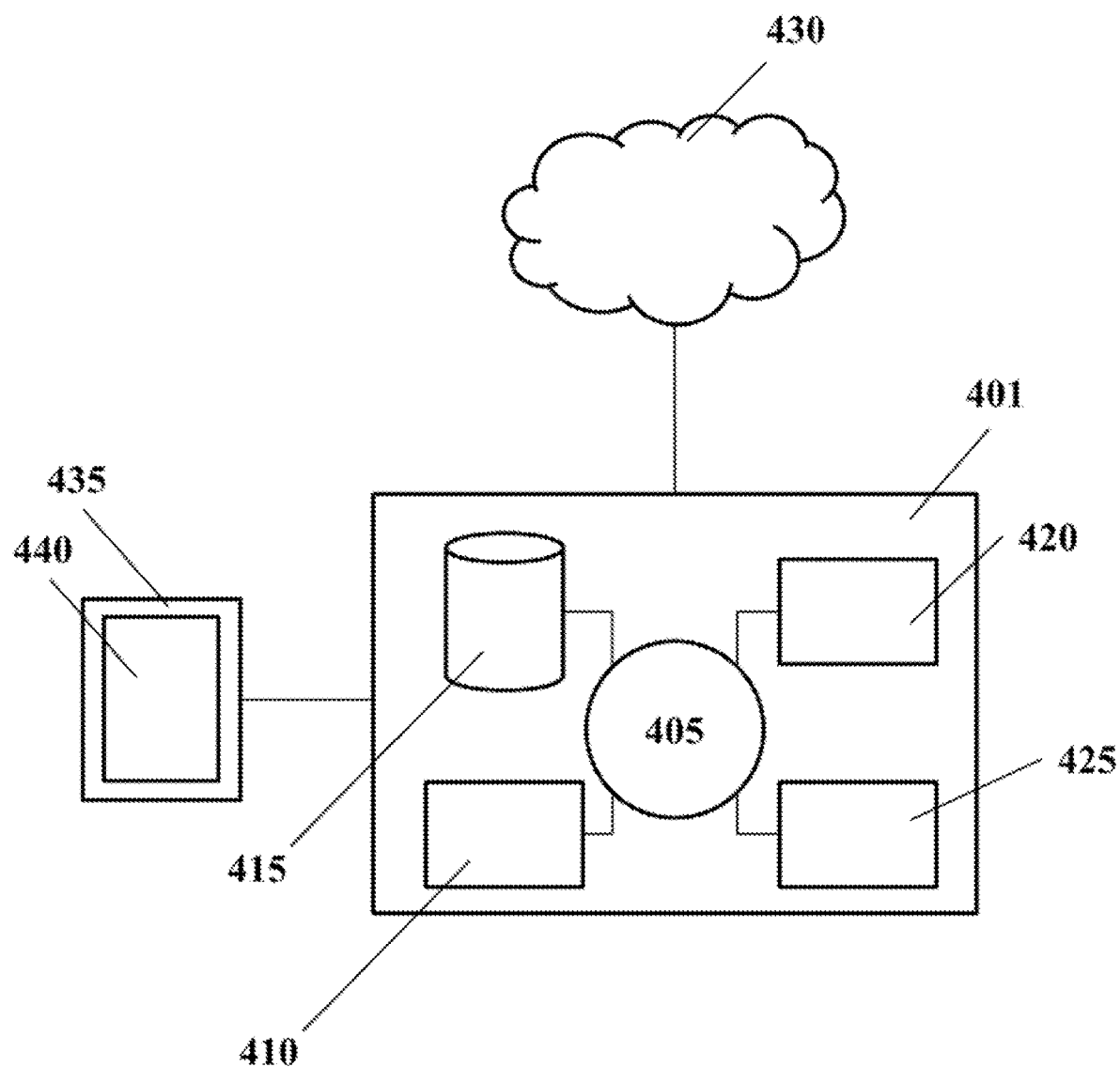
FIG. 4 illustrates a computer system that is programmed or otherwise configured to implement methods provided herein.

The present disclosure provides computer systems that are programmed to implement methods of the disclosure. FIG. 4 shows a computer system 401 that is programmed or otherwise configured to, for example, determine quantitative measures of DNA methylation to generate methylation profiles of DNA molecules at genomic regions; determine cycle threshold (Ct) values for amplification of DNA fragments or derivatives thereof at genomic regions; calculate intensity ratio values of first quantitative measures and second quantitative measures at genomic regions; determine a quantitative measure indicative of a presence, absence, or relative assessment of prostate cancer of a subject; identify or provide an indication of the prostate cancer of the subject; and electronically output a report that identifies or provides an indication of the prostate cancer of the subject.

The computer system 401 can regulate various aspects of analysis, calculation, and generation of the present disclosure, such as, for example, determining quantitative measures of DNA methylation to generate methylation profiles of DNA molecules at genomic regions; determining cycle threshold (Ct) values for amplification of DNA fragments or derivatives thereof at genomic regions; calculating intensity ratio values of first quantitative measures and second quantitative measures at genomic regions; determining a quantitative measure indicative of a presence, absence, or relative assessment of prostate cancer of a subject; identifying or providing an indication of the prostate cancer of the subject; and electronically outputting a report that identifies or provides an indication of the prostate cancer of the subject. The computer system 401 can be an electronic device of a user or a computer system that is remotely located with respect to the electronic device. The electronic device can be a mobile electronic device.

The computer system 401 includes a central processing unit (CPU, also "processor" and "computer processor" herein) 405, which can be a single core or multi core processor, or a plurality of processors for parallel processing. The computer system 401 also includes memory or memory location 410 (e.g., random-access memory, read-only memory, flash memory), electronic storage unit 415 (e.g., hard disk), communication interface 420 (e.g., network adapter) for communicating with one or more other systems, and peripheral devices 425, such as cache, other memory, data storage and/or electronic display adapters. The memory 410, storage unit 415, interface 420, and peripheral devices 425 are in communication with the CPU 405 through a communication bus (solid lines), such as a motherboard. The storage unit 415 can be a data storage unit (or data repository) for storing data. The computer system 401 can be operatively coupled to a computer network ("network") 430 with the aid of the communication interface 420. The network 430 can be the Internet, an internet and/or extranet, or an intranet and/or extranet that is in communication with the Internet.

The network 430 in some cases is a telecommunication and/or data network. The network 430 can include one or more computer servers, which can enable distributed computing, such as cloud computing. For example, one or more computer servers may enable cloud computing over the network 430 ("the cloud") to perform various aspects of analysis, calculation, and generation of the present disclosure, such as, for example, determining quantitative measures of DNA methylation to generate methylation profiles of DNA molecules at genomic regions; determining cycle threshold (Ct) values for amplification of DNA fragments or derivatives thereof at genomic regions; calculating intensity ratio values of first quantitative measures and second quantitative measures at genomic regions; determining a quantitative measure indicative of a presence, absence, or relative assessment of prostate cancer of a subject; identifying or providing an indication of the prostate cancer of the subject; and electronically outputting a report that identifies or provides an indication of the prostate cancer of the subject. Such cloud computing may be provided by cloud computing platforms such as, for example, Amazon Web Services (AWS), Microsoft Azure, Google Cloud Platform, and IBM cloud. The network 430, in some cases with the aid of the computer system 401, can implement a peer-to-peer network, which may enable devices coupled to the computer system 401 to behave as a client or a server.

The CPU 405 may comprise one or more computer processors and/or one or more graphics processing units (GPUs). The CPU 405 can execute a sequence of machine-readable instructions, which can be embodied in a program or software. The instructions may be stored in a memory location, such as the memory 410. The instructions can be directed to the CPU 405, which can subsequently program or otherwise configure the CPU 405 to implement methods of the present disclosure. Examples of operations performed by the CPU 405 can include fetch, decode, execute, and writeback.

The CPU 405 can be part of a circuit, such as an integrated circuit. One or more other components of the system 401 can be included in the circuit. In some cases, the circuit is an application specific integrated circuit (ASIC).

The storage unit 415 can store files, such as drivers, libraries and saved programs. The storage unit 415 can store user data, e.g., user preferences and user programs. The computer system 401 in some cases can include one or more additional data storage units that are external to the computer system 401, such as located on a remote server that is in communication with the computer system 401 through an intranet or the Internet.

The computer system 401 can communicate with one or more remote computer systems through the network 430. For instance, the computer system 401 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 401 via the network 430.

Methods as described herein can be implemented by way of machine (e.g., computer processor) executable code stored on an electronic storage location of the computer system 401, such as, for example, on the memory 410 or electronic storage unit 415. The machine executable or machine readable code can be provided in the form of software. During use, the code can be executed by the processor 405. In some cases, the code can be retrieved from the storage unit 415 and stored on the memory 410 for ready access by the processor 405. In some situations, the electronic storage unit 415 can be precluded, and machine-executable instructions are stored on memory 410.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 401 can include or be in communication with an electronic display 435 that comprises a user interface (UI) 440 for providing, for example, a visual display of data indicative of a presence, absence, or relative assessment of prostate cancer of a subject, a determined presence, absence, or relative assessment of prostate cancer of a subject, an identification of a subject as having prostate cancer, or an electronic report that identifies or provides an indication of the prostate cancer of the subject. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 405. The algorithm can, for example, determine quantitative measures of DNA methylation to generate methylation profiles of DNA molecules at genomic regions; determine cycle threshold (Ct) values for amplification of DNA fragments or derivatives thereof at genomic regions; calculate intensity ratio values of first quantitative measures and second quantitative measures at genomic regions; determine a quantitative measure indicative of a presence, absence, or relative assessment of prostate cancer of a subject; identify or provide an indication of the prostate cancer of the subject; and electronically output a report that identifies or provides an indication of the prostate cancer of the subject.

EXAMPLES

Example 1

Figure 2A:
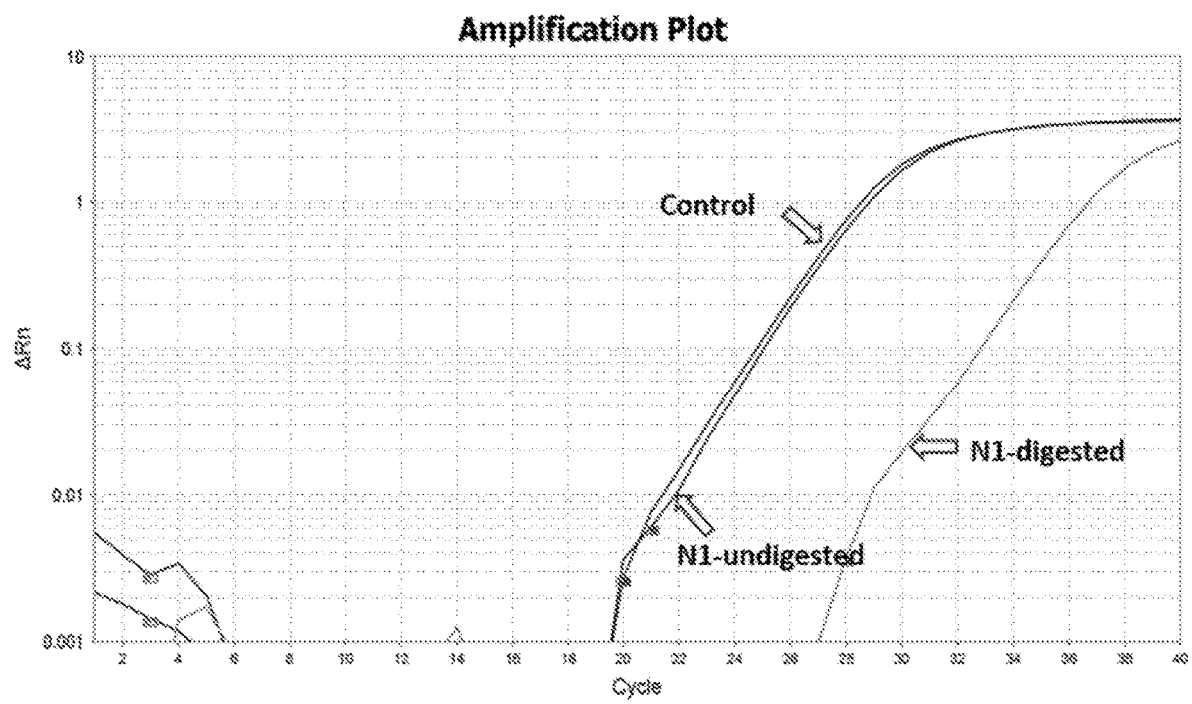
FIGS. 2A and 2B illustrate an example of quantitative polymerase chain reaction (qPCR) amplification plots for a control locus and two restriction loci tested in a healthy (prostate normal) sample ("N1-digested" and "N1-undigested") and a prostate cancer sample ("T1-digested" and "T1-undigested"), respectively, in accordance with disclosed embodiments.
Figure 2B:
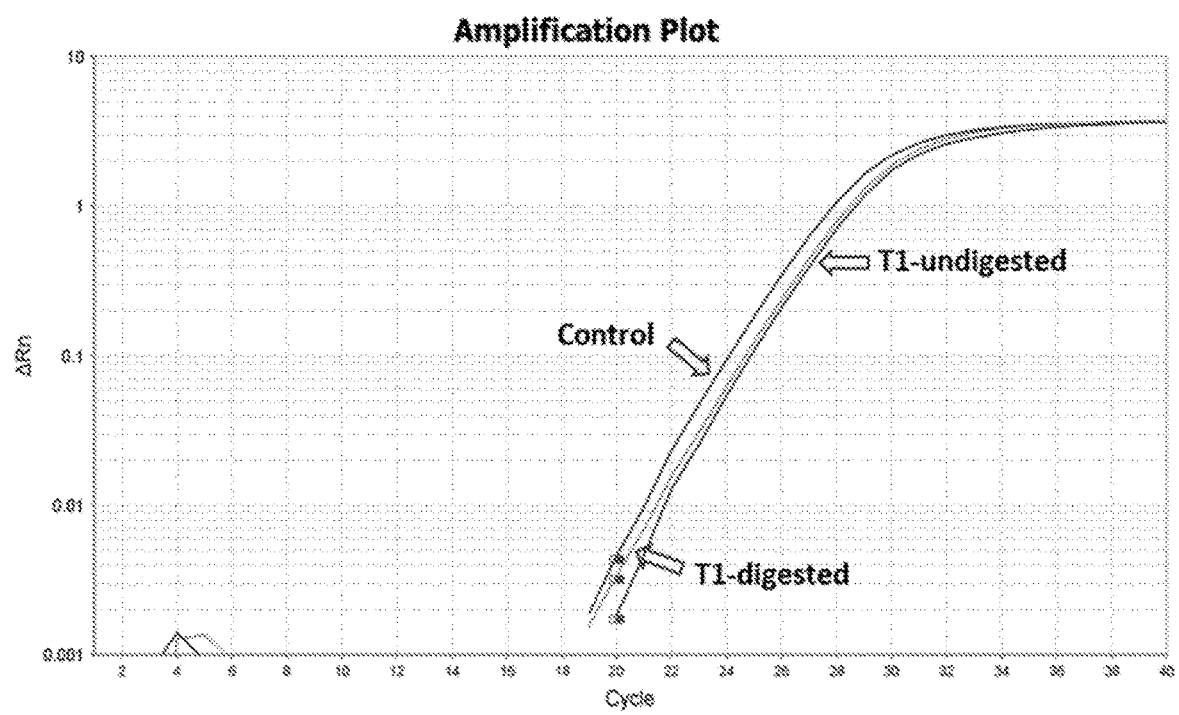
Figure 3A:
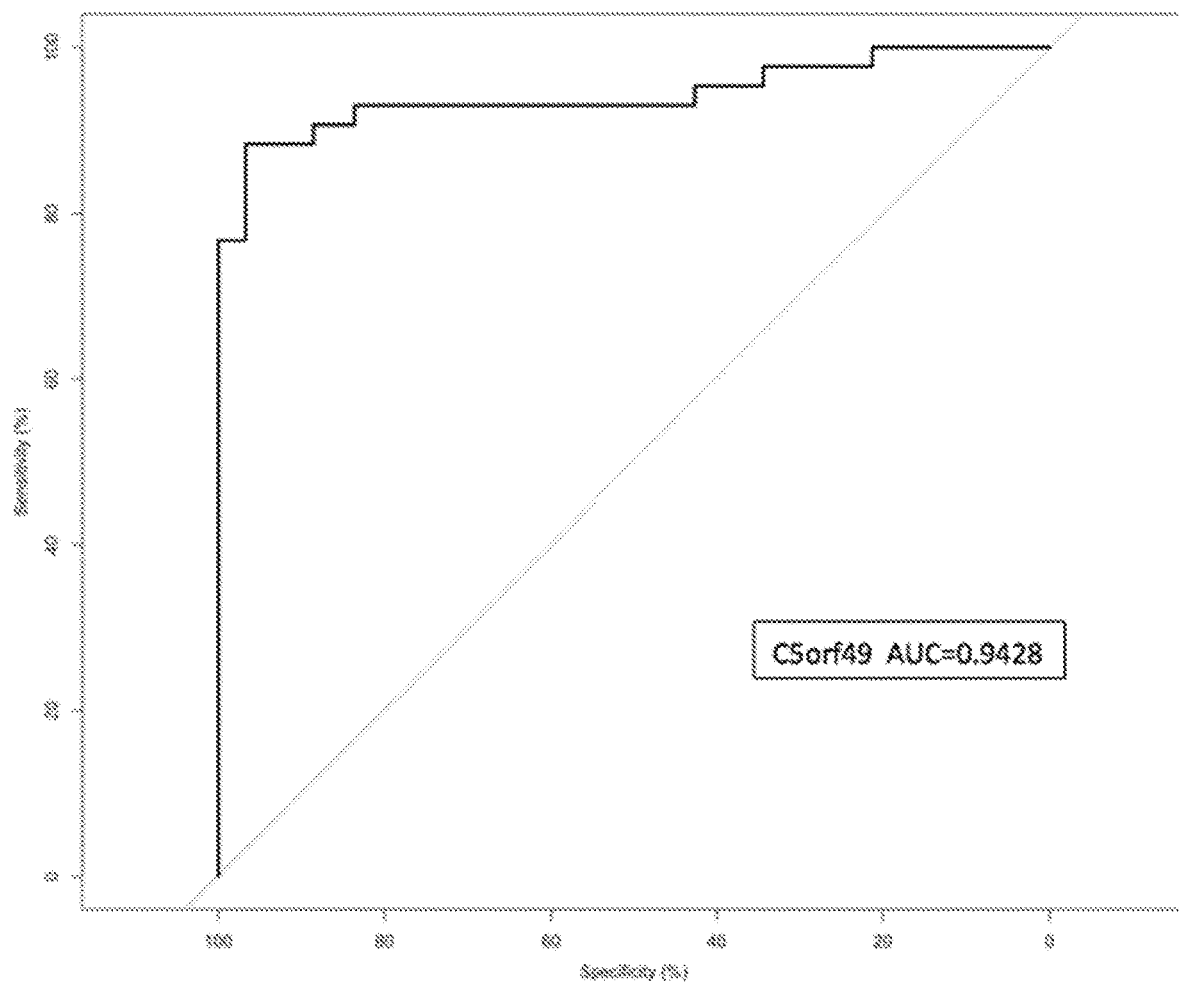
FIGS. 3A-3E illustrate receiver operating characteristic (ROC) plots with area under the ROC (AUC) values for the top 5 target genes C5orf49 (AUC=0.9428), GPR75-ASB3 (AUC=0.883), ANKDD18 (AUC=0.9098), SCGB3A1 (AUC=0.9238), and C9orf3 (AUC=0.9212), respectively, in accordance with disclosed embodiments.
Figure 3B:
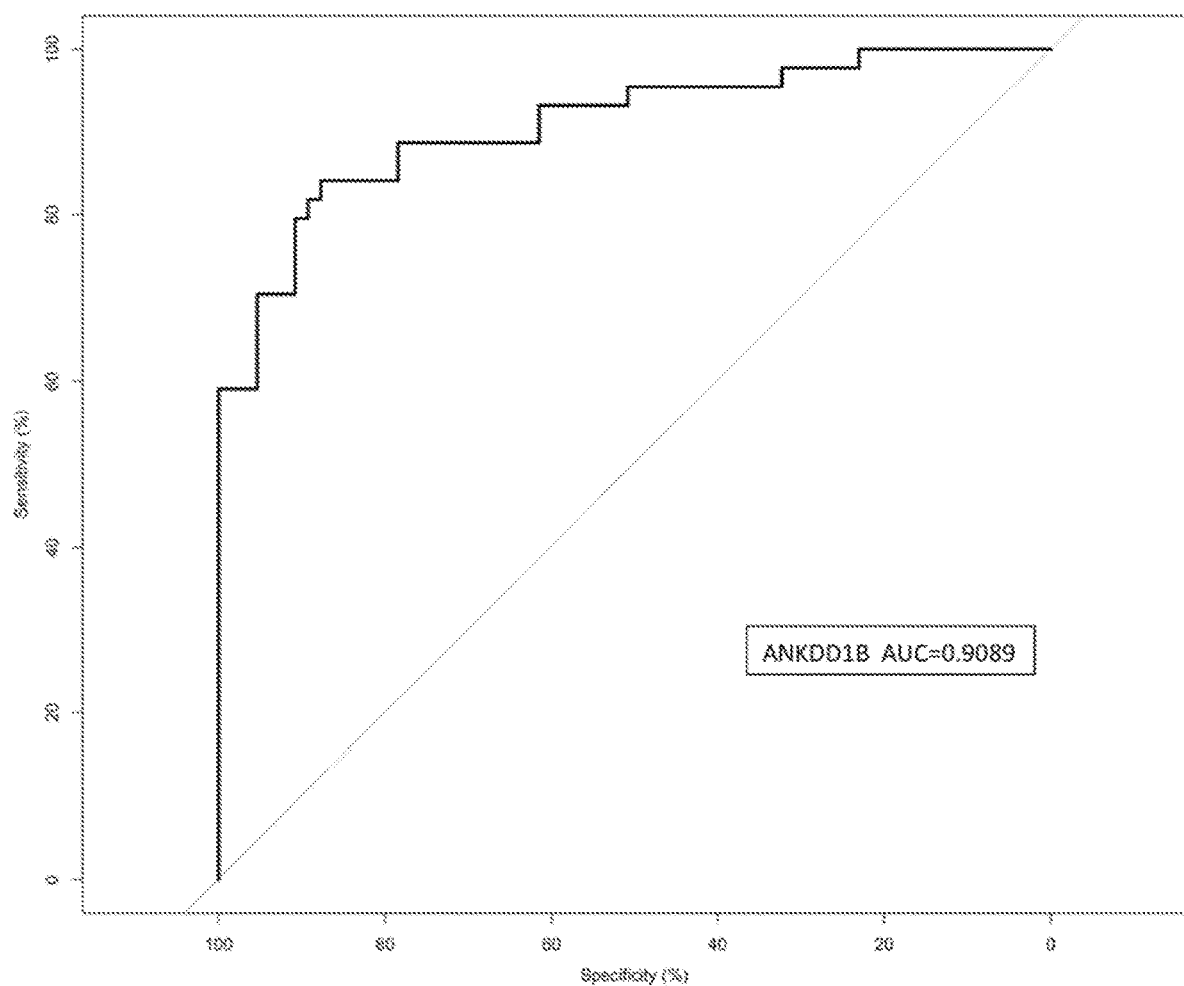
Figure 3C:
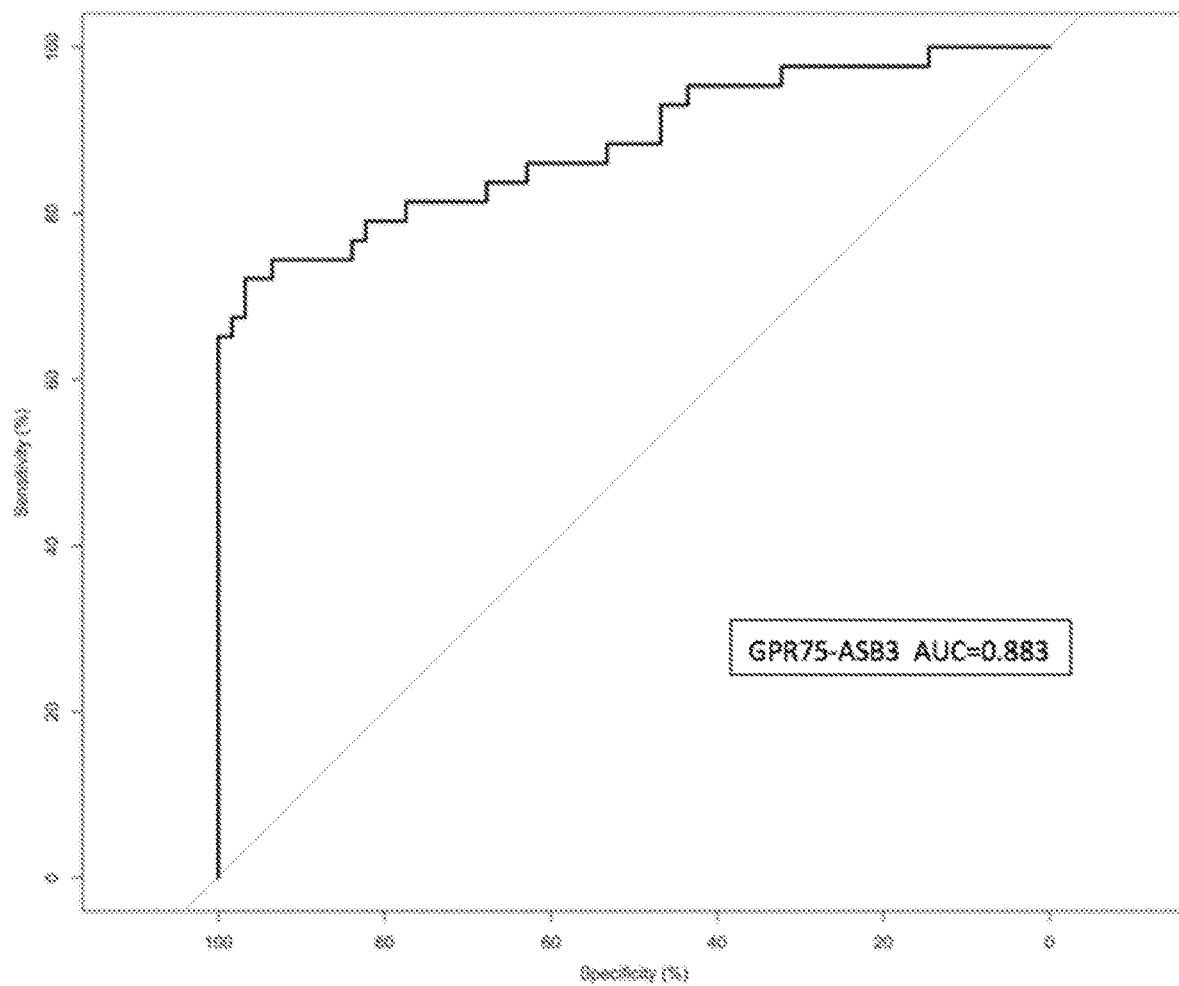
Figure 3D:
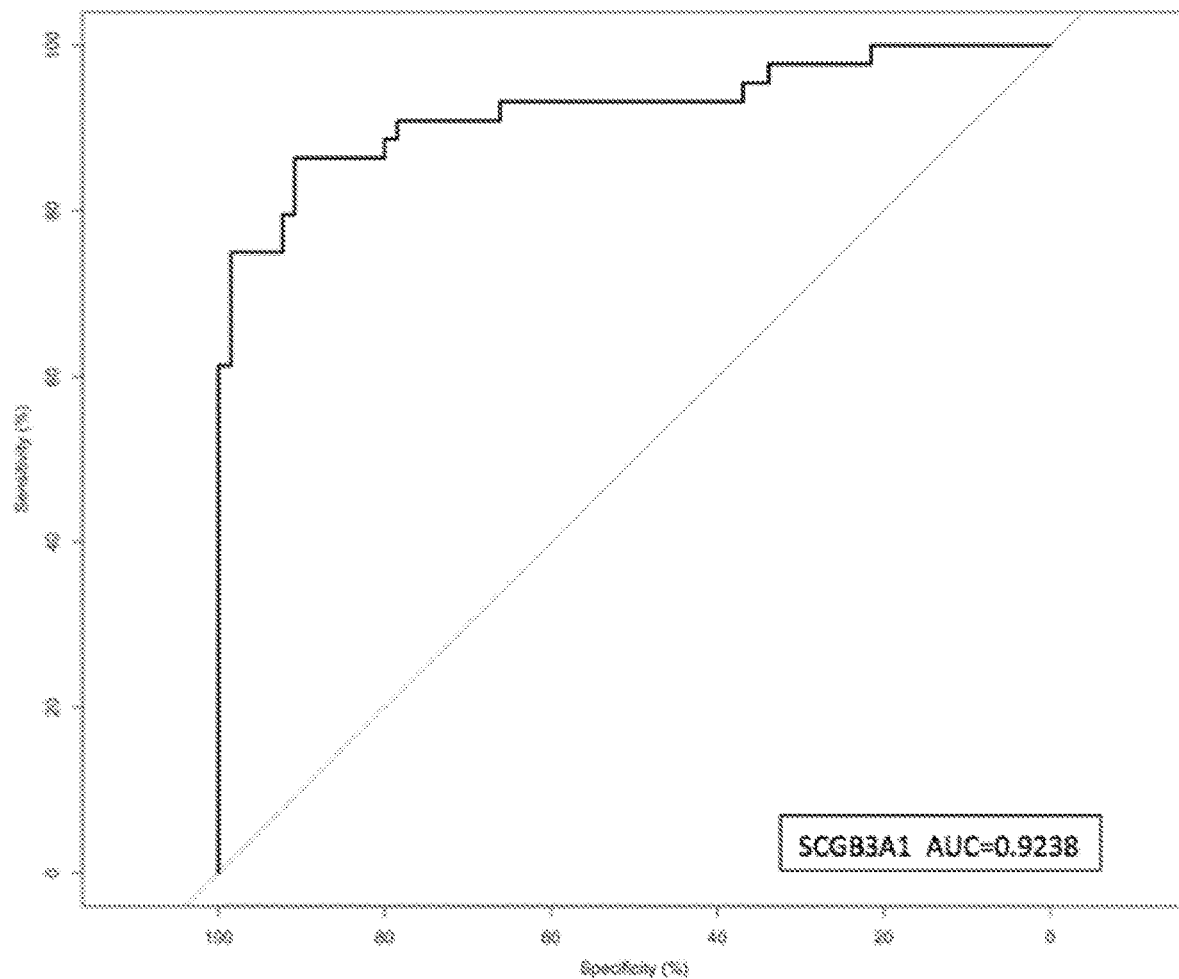
Figure 3E:
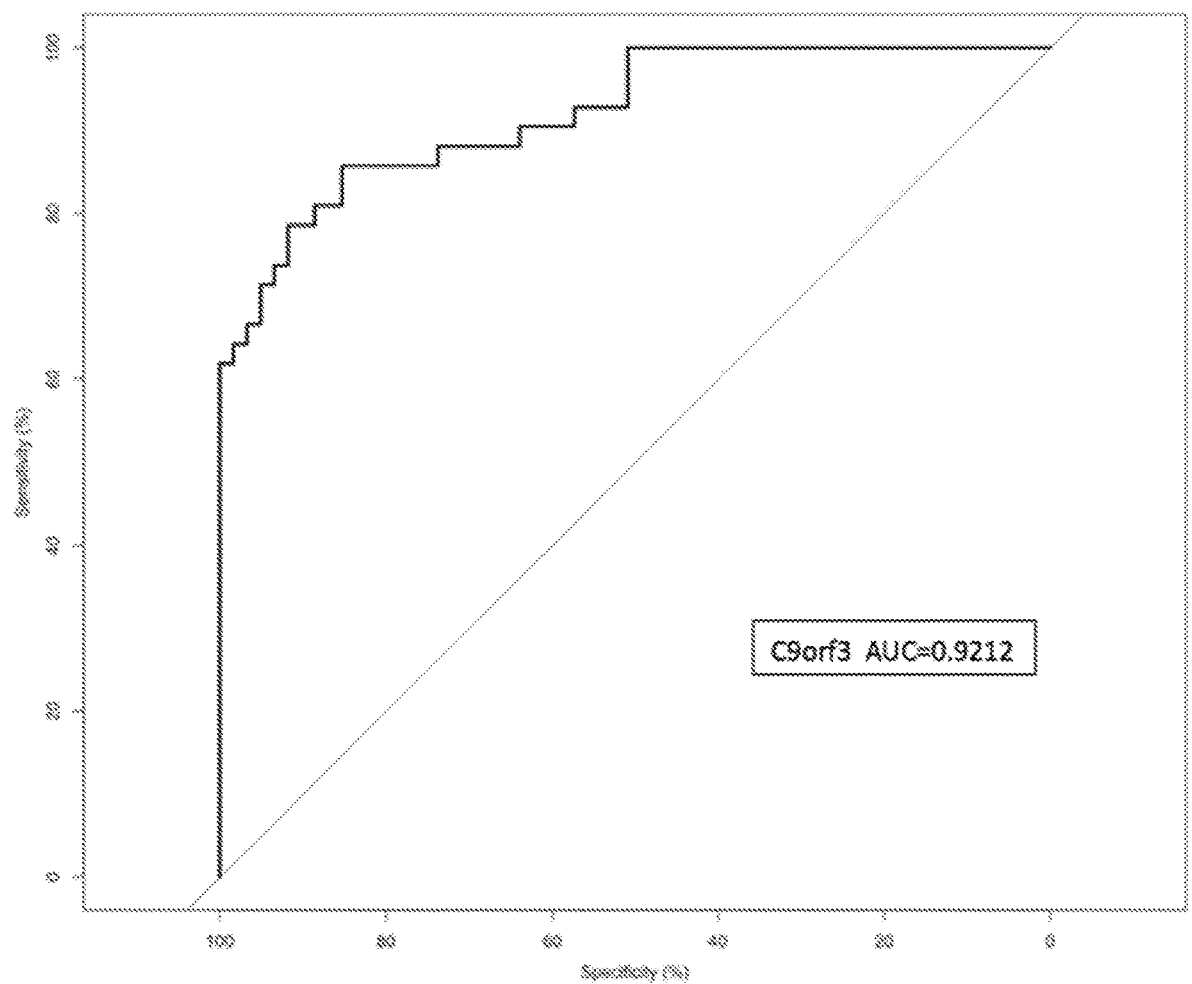

A healthy (prostate normal) sample and a prostate cancer sample were each processed using methods of the present disclosure, including quantitative polymerase chain reaction (qPCR) amplification at a control locus and two restriction loci. FIGS. 2A and 2B illustrate an example of quantitative polymerase chain reaction (qPCR) amplification plots for the control locus and two restriction loci tested in the healthy (prostate normal) sample ("N1-digested" and "N1-undigested") and the prostate cancer sample ("T1-digested" and "T1-undigested"), respectively, in accordance with disclosed embodiments.

FIGS. 3A-3F illustrate receiver operating characteristic (ROC) plots with area under the ROC (AUC) values for the target 5 genes C5orf49 (AUC=0.9428), GPR75-ASB3 (AUC=0.883), ANKDD18 (AUC=0.9098), SCGB3A1 (AUC=0.9238), and C9orf3 (AUC=0.9212), respectively, in accordance with disclosed embodiments.

Table 1 provides a list of marker regions, genomic coordinates, and strands for a set of prostate cancer-specific biomarkers. Marker regions may include marker genes or intergenic regions. Panels of one or more prostate cancer-specific genomic loci can be selected from this list. The genomic coordinates may comprise portions of genes or intergenic regions.

Table 2 provides a list of selected marker regions that are observed to be most influential or most important toward classification of samples for prostate cancer assessment. Table 3 provides performance data (including sensitivity, specificity, positive predictive value (PPV), negative predictive value (NPV), and area under the ROC (AUC)) for this set of selected marker regions that are observed to be most influential or most important toward classification of samples for prostate cancer assessment. Table 4 provides signal ratio values (mean ratio and standard deviation) measured for this set of selected marker regions that are observed to be most influential or most important toward classification of samples for prostate cancer assessment, across the set of normal samples and the set of tumor samples.

TABLE 1

Differentially methylated regions (DMRs) with genomic coordinates

| Marker Region Name | Genomic Coordinates | Strand |
|---|---|---|
| FOXE3 | chr1:47882821-47883001 | + |
| INTchr1_178456064_178456230 | chr11:78456064-178456230 | NA |
| SYT15 | chr10:46970108-46970295 | −;− |
| EPS8L2 | chr11:721572-721764 | + |
| SLC15A3 | chr11:60718471-60718618 | − |
| KDM2A | chr11:66885273-66885367 | + |
| INT.chr11_69452031_69452146 | chr11:69452031-69452146 | NA |
| INT.chr11_69452505_69452633 | chr11:69452505-69452633 | NA |
| BIN2 | chr12:51718739-51718869 | − |
| RHOF | chr12:122231231-122231336 | − |
| ZIC2 | chr13:100637718-100637764 | + |
| NPAS3 | chr14:34269667-34269714 | + |
| INT.chr14_54413694_54413930 | chr14:54413694-54413930 | NA |
| AMN | chr14:103394658-103394809 | + |
| SYNGR3 | chr16:2042521-2042624 | + |
| FAM18A | chr16:10912373-10912435 | − |
| INT.chr16_88700552_88700661 | chr16:88700552-88700661 | NA |
| CYBA | chr16:88717186-88717443 | − |
| ALOX12;LOC100506713 | chr17:6898966-6899129 | +;− |
| RAI1 | chr17:17603974-17604067 | + |
| STAC2 | chr17:37381086-37381291 | − |
| HSF5 | chr17:56564955-56565159 | − |
| UTS2R | chr17:80332893-80332988 | + |
| CELF4 | chr18:34833673-34833820 | − |
| NFATC1 | chr18:77280255-77280394 | +;+ |
| INT.chr18_77377808_77378030 | chr18:77377808-77378030 | NA |
| GNG7 | chr19:2561966-2562267 | − |
| S1PR4 | chr19:3178378-3178763 | + |
| S1PR4 | chr19:3179843-3180439 | + |
| ICAM5 | chr19:10398645-10398816 | +;+ |
| INT.chr19_13209661_13209782 | chr19:13209661-13209782 | NA |
| LYL1 | chr19:13210312-13210610 | − |
| KCNN4 | chr19:44278646-44278776 | − |
| DACT3 | chr19:47152943-47153124 | − |
| GRIN2D | chr19:48946038-48946234 | + |
| ARHGEF33;LOC375196 | chr2:39186942-39187340 | −;+ |
| GPR75-ASB3 | chr2:54086834-54087146 | − |
| LOXL3;DOK1 | chr2:74782170-74782343 | −;+;+ |
| SPEG | chr2:220299387-220299671 | + |
| OBSL1;MIR3132 | chr2:220416365-220416499 | −;− |
| ADRA1D | chr20:4202298-4202568 | − |
| M1R5095;RBM38 | chr20:55965671-55965845 | +;+ |
| PR1C285 | chr20:62200059-62200211 | − |
| INT.chr21_44819085_44819433 | chr21:44819085-44820000 | NA |
| CLDN5 | chr22:19511041-19511173 | − |
| SCARF2 | chr22:20783492-20784226 | − |
| BCR | chr22:23523796-23524384 | + |
| BAIAP2L2 | chr22:38485113-38485188 | − |
| CELSR1 | chr22:46932291-46932543 | − |
| PLXNB2 | chr22:50738284-50738549 | − |
| GPR62 | chr3:51989765-51989989 | + |
| CTBP1 | chr4:1210457-1211157 | − |
| INT.chr4_55015512_55015839 | chr4:55015512-55015839 | NA |
| SCGB3A1 | chr5:180017902-180018673 | − |
| C5orf49 | chr5:7849801-7850443 | − |
| MCI | chr5:54516403-54516681 | − |
| ANKDD1B | chr5:74907331-74907750 | + |
| SH2B2 | chr7:101961701-101962105 | + |
| MEST;MESTIT1 | chr7:130131962-130132110 | +;+;+;+;− |
| TMEM176B;TMEM176A | chr7:150497959-150498298 | −,+ |
| KCNH2 | chr7:150655309-150655540 | −;− |
| KBTBD11 | chr8:1950518-1950729 | + |
| INT.chr8_38508331_38508694 | chr8:38508331-38508694 | NA |
| INT.chr8_48675655_48676143 | chr8:48675655-48676143 | NA |
| C9orf3 | chr9:97807476-97807681 | + |
| C9orf172 | chr9:139740230-139740378 | + |
| CLIC3 | chr9:139889657-139889955 | − |

TABLE 2

Selected top marker regions

| Marker Region Name | Genomic Coordinates | Strand |
|---|---|---|
| SCGB3A1 | chr5: 180017902-180018673 | + |
| ANKDD1B | chr5: 74907443-74907561 | + |
| C5orf49 | chr5: 7850160-7850286 | − |
| C9orf3 | chr9: 97807476-97807681 | + |
| GPR75-ASB3 | chr2: 54086834-54087017 | − |

TABLE 3

Performance data for the selected top marker regions tested in a set of 52 normal and 47 tumor patient tissue samples

| Locus | Sensitivity | Specificity | PPV | NPV | AUC |
|---|---|---|---|---|---|
| SEQ ID NO:127 | 78.80% | 98.20% | 97.10% | 86.10% | 0.909 |
| SEQ ID NO:201 | 88.10% | 94.70% | 92.50% | 91.50% | 0.943 |
| SEQ ID NO:134 | 73.80% | 89.50% | 83.80% | 83.90% | 0.883 |
| SEQ ID NO:43 | 88.10% | 91.20% | 88.10% | 91.20% | 0.924 |
| SEQ ID NO:96 | 81.00% | 86.00% | 81.00% | 86.00% | 0.921 |

TABLE 4

Signal ratio of the selected top marker regions tested in a set of 52 normal and 47 patient tissue samples

| Locus | Normal Mean Ratio | Normal Standard Deviation | Cancer Mean Ratio | Cancer Standard Deviation |
|---|---|---|---|---|
| SEQ ID NO:127 | 78.2 | 2.8 | 5.1 | 3.6 |
| SEQ ID NO:201 | 52.0 | 2.9 | 3.0 | 3.1 |
| SEQ ID NO:134 | 3.0 | 2 | 2.5 | 2.2 |
| SEQ ID NO:43 | 34.3 | 3.7 | 4.1 | 4.3 |
| SEQ ID NO:96 | 4.2 | 1.8 | 1.8 | 1.7 |

TABLE 5

Area under an ROC curve (AUC) with respect to identification of prostate cancer using combinations of one or more loci

| Loci | Sensitivity | Specificity | AUC |
|---|---|---|---|
| {SEQ ID NO:134} | 80.9% | 82.4% | 0.883 |
| {SEQ ID NO:134, SEQ ID NO:127} | 76.2% | 87.7% | 0.895 |
| {SEQ ID NO:134, SEQ ID NO:127, SEQ ID NO:43} | 78.6% | 98.2% | 0.904 |
| {SEQ ID NO:134, SEQ ID NO:127, SEQ ID NO:43, SEQ ID NO:96} | 80.9% | 98.2% | 0.908 |
| {SEQ ID NO:134, SEQ ID NO:127, SEQ ID NO:43, SEQ ID NO:96, SEQ ID NO:201} | 83.3% | 98.2% | 0.917 |

TABLE 6

Sequences of the DMRs in Table 1

| Marker Region Name | Sequence | SEQ ID NO: |
|---|---|---|
| FOXE3 | ggcccgctgcccgctgagcccctcctggccttggccGGGCCGGCAGCCGCTCTCGGCCCGCTCAGCCCTGGGGAGGCCTACCTGAGGCAGCCGGGCTTCGCGTCGGGGCTGGAGCGCTACCTGTGAGCCTGCGCCGCGCGGGCAGGCACCTGTGCGACCTGTGCCCCGGACCTGCGGCGC | 277 |
| INTchr1_178456064_178456230 | GGAGGCGGAAGCGCGCGAGTAGGAGGTGCGGAGGTCGGGCTCGCGGGGCTCCGGGCTGCCCCTCTGAGTGAGCCGCGCTGCTGAAGCCGGGCCCTGCGAGGCGCCCACGGGGCCGGTGCTGGTCCCTAGGGCCAGAGAGAAGACTTCTGTGGGGTCCGCTGCGCCC | 278 |
| SYT15 | GGGGGTGCTCAGACGCTGGGTTCCAACCGCTGGCCACCTGGGGCGGGCCAAAAAGGTGCCTCCCTTAGGGTGACGTGCGGCCGCGGGGCATTCAGGTCTCAGGGATCTGCACTGGGTGGGGTGGTGAGAAGGCCGGACCCCCCACACCTCCTAAGCCGCAACTGACCGCGAAGAGCGGGCCTCAGCG | 279 |
| EPS8L2 | CAACTGCGCCCTGGACGACATCGAGTGGTTTGTGGCCCGGCTGCAGAAGGCAGCCGAGGCTTTCAAGCAGCTGAACCAGCGGAAAAAGGGGAAGAAGAAGGGCAAGAAGGCGCCAGCAGGTGCAggggacagggacggggccggcaggtgcaggggacggggccagcaggtgcaggggacgggacgggac | 280 |
| SLC15A3 | GGCACCGAAGGAGGTGAGGTTGCTCCGGACGGAGCTGGCGGCCAGGCCGAGTAGCAGCAGGCCCGCGTAGAGGACGGGCGCGCAGTAGGGGCTGGGCGAGGAGCGCGGGCAGCCGGCCGAGGGGCAGGCAGGTCCCAGCGGCGACGC | 281 |

TABLE 6-continued

Sequences of the DMRs in Table 1

| Marker Region Name | Sequence | SEQ ID NO: |
|---|---|---|
| KDM2A | CCCGGATCGCGGCTGGGCTGCTCGCATGGCA CTGCTCGGGTACCTCCGGCCGGGCTCCGTCGA CGTTCGGAGCCTGCTGGCCCGTCGGGCAGCT | 282 |
| INT.chr11_69452031_69452146 | GGAGTGGGGCATGCCGTGGGAGCCCACGAGG GCCTCAGCGCGGATCCTCCGCCGGAAAACCG GCTCCCGCGAGCCGCCGCCGCAGGTTTCCTA GGCCCCGCGAGTCCCGCAGCGA | 283 |
| INT.chr11_69452505_69452633 | CCCCTACCTGTTGGGTTTGCGTTTTAACTCCA GCGCACACCTTGCCGGCAGCCCTCGGAGCTA GGGGAGGGGTCTCGTTTCCCCGCAGCCCGCC GGACAGACGACTGGGGCACGGGAGGGGCGG TGGC | 284 |
| BIN2 | aaataaataaataaataaataaatGAGGAACAACTAAG CTGGAGATAGAAACAGGGTAGGGGGCTGGTT CTTAGGCAAGAGAATGATCACATTGAAAAAA GGCTGAGGAGGATAGTATGGACGCCC | 285 |
| RHOF | GTCCCGGATCAGCCCCCCCTCACCCCGCTGGG CTCTGGAATTCCCGAGGGGGCGCCCCGGGGT GGCGGCCGCCTGTCCGTGCTCGGGACGCTGG GGACTGAGGGT | 286 |
| ZIC2 | cggcggcggctgcggcggcggcggccgcggtgtccgcggtgcaccg | 287 |
| NPAS3 | cccggcgccgacggcgcggccgcccgcAAGACTCAGTTCG GCGCCTC | 288 |
| INT.chr14_54413694_54413930 | CGCCGCGGACGCGCCGAGCCCTCTCAGTGTG GCGCTGCCCGGCGGCGAGGGGGGTGTGGAAC GAAGCACGGTCAAGACAGAAAACAAAGTCA GCAGGTCACCTGGCAGGTTCTGGGCGAATTA TGCAACGAAAGCAGGGGAATGTTTGATGCGT CCCACTCCACACCCCCCAACCTTTTTTTTTTT TTTTTAAGCTCCTAGGAAGCCGGTTCCAGTTT AAGGGTTGGGTAGGGAT | 289 |
| AMN | GTGCACAGGGTCTCGGCTTCTCGTCCCAGGG GACTGGGGGCGGGGTGGGCGCGGAGCAGGC CCGGACCCCCGCGTGGCGCCGCCTCAGCCCG TGTCTCTTGCAGCTCCTGCCGCTGGATGGGA ACTCGTCCTGGCTTCAGGAGCCGGATT | 290 |
| SYNGR3 | GGCGAGCCCAGGCGAGGCGCCCCAAGCCTCG GGCCCACCGACCTTTCCTCCTCCGGGCGAGGC CGCCGTGGGCCACCGCGTGGAGCGTCGCCCT GACGCGCCG | 291 |
| FAM18A | CGCCCAGGCCCGGGGCTCCAGCTCCGCCCGT CGCCGCTGAAGGGGTCGGACGCCGGGCGGGC | 292 |
| INT.chr16_88700552_88700661 | CATGACGATTTTGCACCCCCGCCAGCAGTGCC CTCGGCTGGACACACCTGCGTTGTGGGCAGC CGGCAGCGCGTGACCCACTGTGCACCTGCGC CTTGATGTAGGGGGG | 293 |
| CYBA | CCAGCCCGCGGCCTGAGGGTCCCGCCCCCGT TCCCCGCACCCTCCTGGCCTGACCCCGGCCCG GCCTGGCCCGCCTGGCGCCCCACTTCCCCACC CTGTAAGTAGCCCGAGGTCCCGGCTGGGGTC TTGGGACACCCCTCCAGGCTGCAGCCTCCACC GTCCCTGACGTGCACTCACTCAGGCCGGACG CCAGCGCCTGTTCGTTGGCCCACATGGCCCAC TCGATCTGCCCCATGGCGACACGAACCCGGC TGGGA | 294 |
| ALOX12; LOC100506713 | GGGTCCCAGCCCAGAAAAGCGGAGACCTTCC CCTCCGTTTGGAAGATGGACTCATCCCCTACT TCCTCCTGGCTCCCCAGAAGACCTGGAGACCT CGGGAAGTGTTCTCATCTATGTTCGCTCCAAC CCGGGGGCTCAGGCCCACCTCGATCCCGCCTT CCCG | 295 |

TABLE 6-continued

Sequences of the DMRs in Table 1

| Marker Region Name | Sequence | SEQ ID NO: |
|---|---|---|
| RAI1 | GGGGCCTCCGCGAGGCCGGGCCTCGTCCGCC GAGGCCGCAGTCCGGCCCCTCTCGTCCTCGG GGCGCGGCGCGTTCGTTTCATTAATTTATCG | 296 |
| STAC2 | GGCCGCGGCCTCGCGTCCCCGAGCCCAACAG GGCTAGGAGCGGGGAATGCAGGACTGCGGA GGGGCAGGGAGAGACGCCCTGAGACGCGGA GATAAACACCCGGAGACGCCGGGAGAGACG GGGAGAGACGCACACAGAGACACCAAGACA CAGACACGCAGGTTGTAGAGACAAATTCAGA GACACGAGCGAGGATAGAGGCGC | 297 |
| HSF5 | GCCAATGGGTCCCCGGCGCCTTTCCGACGCCC ATAGCGTGAGGACGTGCGAAAATGCGCCCTC CAGCGGCGGTTGCTCCCCGCCGCCCATGTGCC CACTGTGGGCGAGGGCACGGGCAGTCCGGAC TCACCGTGCGGCTcgggccggggccccgcgggcggcggcg gcTGCTGGTGCTGCAGTGGCGCGGTGGCGGCG GAGGCC | 298 |
| UTS2R | GCGCGCCTGGCCCGCGCCTACCGCCGCTCGC AGCGCGCCTCCTTCAAgcgggcccggcggcggggggcg cgcgcgcTGCGCCTGGTGCTGGGCAT | 299 |
| CELF4 | GGTCCGTCTGGTTCCCTCCCAACCCCCGTccccg cgccccggccgccccccggTTACCTGTGCGAGTCCTGGT CTCCCCCGGGGGACGCTCCCGCCGGCGCTCA GTACGGGCGATTGGCGTCTTTGGGCCGCTTCA GCTGCACCTTGA | 300 |
| NFATC1 | GCAGCCCTCGCGTGGCGTTGCTGCCTCTGCAG ATGCCTCCGGAGGGACTCGGTGTGTCTCGGT GTTGATTTCAGAACAGGGGAGATGCTGACGT GTCCCGGTGGCTCTCACAGCACAGTGGAAGG CGAGTGGCAGCTCC | 301 |
| INT.chr18_77377808_77378030 | CCCGCGCGGACAAGCAGCTTCCCAGAGGCCT CAGGAAGCCCCGCCCGAGGGTGTCAGCTCCA GCTCTGAGCGGGTCCCGCAAACGCCCCAGCG TGTTCCCACCGGTGACCCCGACACCCCAACA CCCCAACGCCCCGCACCGCCCTCAGCAGCCG CGCCTTGGCCAGCGGGTGCCCCGGTGCCTGC GGCCTCTGACATAGAAAACGAGGAAGGAGGc gggcg | 302 |
| GNG7 | CGGGGCGACCCGAGAAACAGGAAACCCTGTT TCTGAGCTTCGCAGGCTCTTCTGGGAGACCAG CGGGTAATCCCCTTCCTCCGACATTTCTCTGA GAAGTCTCTCTGCGTTCTGCTTCTCAGAAAGA AACCAGGGTCCGGGGCAGGCATTCACGCCCT CCACCCACTCAGGGGTTTGCAGTAACACCCTT GGGATCTGCAGGTTCACACAGAGCCAGAGCC GTGAGTCACCGCAGCCCCGGAGCTGCCGGGG TCCCCACCTGCTCAGCCCCAGGAACACACAT CTACAGCGGGTTCCTTTT | 303 |
| ICAM5 | CGCCTTCTGCTCCCAGCTTGGAGCCCCGCGCC CACAGCTTTGGCCTCCGGTTCCATCGCTGCCC TTGTAGGGATCCTCCTCACTGTGGGCGCTGCG TACCTATGCAAGTGCCTAGCTATGAAGTCCCA GGCGTAAAGGGGGATGTTCTATGCCGGCTGA GCGAGAAAAGA | 304 |
| LYL1 | CCCGGGAGGGGTGGGGCCTGCGGCCAGAGCT GCGGCTTGGTCGCGCAGCAGCCGCACCAGGA AGCCGATGTACTTCATGGCTAGGCGGAGCAC CTCGTTCTTGCTCAGCTTCCGGTCGGGCGGGT GCGTCGGCAGCAGCTTCCTCAGCTCGGCGAA GGCGCCGTTAACGTTCTGCTGCCGCCAGCGCT CCCGGCTGTTGGTGAACACGCGCCGGGCCAC CTTCTGGGGCTGGTGCCCTGTGGACAAGGAG GGCCGGGTTGGTGCCATGGCCCAAAGGGCGG CCCCTCCTGCCCTCCCG | 305 |

TABLE 6-continued

Sequences of the DMRs in Table 1

| Marker Region Name | Sequence | SEQ ID NO: |
|---|---|---|
| KCNN4 | CACGGCGGGCCCCGCACGGGCGCCGGGTGCA GCCCACACACCACCAGCTCCAGCACGATCTG CGCCGCCTGCCGCCCGGTCAGCGCCACGCGC CAGTCCCGCAGCCCGTTGTCGGTCATGAACA GCTGCC | 306 |
| DACT3 | GGCTGCGCATCGCCACGGCGTGCAGGGGGCT GGGCGTCAGAAAgggcccggcgcgggcccgccgcTCCG CCGAGGAGCAGGCCTCCGGGCCGGCGGACCC CCCTGCCGTCGGGTAGGGCGCTGAGAAGGAC CGCGGCACCGCTGCCCGCGCGCCCACCACCT CCGGAGCGCTGGGACTGGC | 307 |
| GRIN2D | gggggcgcgggccTGGCCGACGGCTTCCACCGCTA CTACGGCCCCATCGAGCCGCAGGGCCTAGGC CTCGGCCTGGGCGAAgcgcgcgcggcaccgcgggggcgca gccgggcgcccgctgtccccgccggccgcTCAGCCCCCGCA GAAGCCGCCGCCCTCCTATTTCGCCATCGTAC GCGACAAGGAGCCAGCC | 308 |
| ARHGEF33; LOC375196 | GTAAGCACAGCTCTTTTGTACTCTGTTTTCCC CCTAAAGACATCTGATGCCCCCAGTGAAGAA AAGCCAACAGCAGCAAAGCCTGATGGAGAGC ATGCAGCCCGGGAAGCCCAGTGACTGGGAGC TGGAGGGCAGGAAGCACGAGCGGCCCGAGA GCCTTCTGGCACCGACGCAGTTCTGCGCGGCC GAGCAGGACGTGAAGGCGCTGGCCGGGCCCC TGCAGGCCATCCCGGAGATGGACTTCGAGTC CTCTCCGGCGGAGCCGCTGGGCAACGTGGAG CGCTCCCTGCGCGCCCCGGCCGAGCTCCTGCC CGATGCCCGCGGCTTCGTGCCCGCGGCCTAC GAAGAGTTCGAGTACGGCGGCGAGATCTTCG CGCTGCCCGCGCCCTACGACGAGG | 309 |
| GPR75-ASB3 | CACCAGGAAGACAGGTACGCGGAGCCGGGCC TGGCCCAGCGCAGCCGCGCTCCTCGCTATCCC GCCAGCCTCCGGGAGCCGTCTCCGGCATCGT GGGGTTGTCCTCCTCCAGGGGCCCGCGGCCTC TCACCTGCCGGGTGGCCGCAGCGCCGCCCCT CCTCCATCTCGCAGTCCGGACCCCAGCTCCGC CTGCCGCTCTGGATGATGCAGGACTAGAGGC ATCATCGCCATCGCCACCGCCTCCGCGCATCC CGGGAGCCGCGGCAAGACGCGGGCGCAGAG GCGCAGTCACGGAGACGCCGAGGGCACCGC | 310 |
| LOXL3; DOK1 | TTTGGAAGCCCCAGATCCCAAATCGACTTGC GCCGCAACCTCCTTCCCCGTCGGGACCCGGG CCGCCTGCGCACGCCACTCCCTCTCGAGCACT CTCTCTCTCTCCCTAGAGGTGGAGGAAGACCT GGGCCGTGCTCTACCCGGCCAGTCCCCACGG CGTAGCGCGGCTCGAG | 311 |
| OBSL1; MIR3132 | CATCTCATACTTATCTCCCGGGCACAGCTCGG CCCCCTCCCGCAGCCAGCACACGTGGCCCCC CGAGCGGGACACAGTCACCTCCAGCACCGCC CGGCGGCCCACCAGAACGGTCTTCTCGCGAG GGGGGTGGC | 312 |
| MIR5095; RBM38 | CCTTTCTATGGCTGGGGGCCGGATGAGGGAC CCGGGTCTGCTCTTACTCGCCCCAAGGGTCCC TGACACCAGCCCAGAACGGGGTGGAGCTGGA AAGAGCCCACACCTGCTTCCTCTGCCCACCTC ATCTCCCGCGGGGCCTCTGAGACCGCCCGGG ACCCGCTTCTATCGCGG | 313 |
| PRIC285 | GCTGCAGCCCCAGGGCCAAGCAGCAGCGGGC CGGAAGCAGCAGCCACAGCGCCTGCTCTGAG CTGGCCCGCCTCTCCAGCCGCACCTCGAACAC CGTATTGTCGGGTGCAGGTACAGGGGCCACC AGGGCTGTGCTGACCGCCCGGCCCAGC | 314 |
| CLDN5 | GGTCCATGCGGGGCTCCCCAGGCTTATCCAA CGCCTCGCAGGCGTGGCTGGCAGGAGGGGCC CGGCCGTGCCCAGCGCCCTCAGACGTAGTTCT TCTTGTCGTAGTCGCCGGTGGCCGTGGGCCGC CGCGGC | 315 |

TABLE 6-continued

Sequences of the DMRs in Table 1

| Marker Region Name | Sequence | SEQ ID NO: |
|---|---|---|
| BCR | ACGGCGCGGGCTCGAGCGTGGGGGATGCATC<br>CAGGCCCCCTTACCGGGGACGCTCCTCGGAG<br>AGCAGCTGCGGCGTCGACGGCGACTACGAGG<br>ACGCCGAGTTGAACCCCCGCTTCCTGAAGGA<br>CAACCTGATCGACGCCAATGGCGGTAGCAGG<br>CCCCCTTGGCCGCCCCTGGAGTACCAGCCCTA<br>CCAGAGCATCTACGTCGGGGGCATGATGGAA<br>GGGGAGGGCAAGGGCCCGCTCCTGCGCAGCC<br>AGAGCACCTCTGAGCAGGAGAAGCGCCTTAC<br>CTGGCCCCGCAGGTCCTACTCCCCCGGAGTT<br>TTGAGGATTGCGGAGGCGGCTATACCCCGGA<br>CTGCAGCTCCAATGAGAACCTCACCTCCAGC<br>GAGGAGGACTTCTCCTCTGGCCAGTCCAGCC<br>GCGTGTCCCCAAGCCCCACCACCTACCGCAT<br>GTTCCGGGACAAAAGCCGCTCTCCCTCGCAG<br>AACTCGCAACAGTCCTTCGACAGCAGCAGTC<br>CCCCCACGCCGCAGTGCCATAAGCGGCACCG<br>GCACTGCCCGGTTGTCGTGTCCGAGGCCACC<br>ATCGTGGGCGTCCGCAAGACCGGGCAGA | 316 |
| BAIAP2L2 | GTGCGGGGCAGGGAGCGACGGTCTGGCTCTA<br>GCTGGGACGCGGGCCTCGCGTCGGGCTCGGT<br>GCCGTAGGAGCCG | 317 |
| CELSR1 | GGTTCGTTCTCAAACAACGCCACCTGGTAGTT<br>GGGCATCGGAAACTTCAGGCTCCCTCTGCCG<br>CTCGTgccccgccgggcccgtcgcgccggccccgccgggcTT<br>CGGGCAAGTTCGGCGGCAGGGCGGCGATGG<br>GGATGGCGACGCGGAGGGCGTCCCCGCGGTG<br>GCGGCCTCCAGCGCCAGTCCCACCCGGACGG<br>CGCCAGCCGCGCGCCGCAGGGCGCACAGCAG<br>ACGCAGGCGGACCGAGCCGCCC | 318 |
| PLXNB2 | GGCCTGTGTGGAGCGCCCTGGACTATTCCTCG<br>CAGGCCGACCCAGGTGGCACAGCCCCTCCCC<br>CGGCGCCGGCACCGCCAGACTCCCCGGAGGG<br>CGCAGAACGGTTGCCCGGGAGCCAGGGGCAA<br>AGCGCGCCCGGGGCCAGGAAGCGCAGGGACT<br>AGGCCCGCGCCTCCTCGGCGCCGCCCACTGC<br>CCCCCGCGAGCCCAAGCTCCACGGCCACCGC<br>CCGCGCCCTCCCGGGGACTCCGGCGCCCCGT<br>CCGCCCCTCGGCCTCG | 319 |
| GPR62 | GCGCGCTGCTGGTCGTGGTGCTGCGCACGCC<br>GGGACTGCGCGACGCGCTCTACCTGGCGCAC<br>CTGTGCGTCGTGGACCTGCTGGCGGCCGCCTC<br>CATCATGCCGCTGGGCCTGCTGGCCGCACCG<br>CCGCCCGGGCTGGGCCGCGTGCGCCTGGGCC<br>CCGCGCCATGCCGCGCCGCTCGCTTCCTCTCC<br>GCCGCTCTGCTGCCGGCCTGCACGCTCGGGGT<br>GGCC | 320 |
| INT.chr4_55015512_55015839 | ccgcggagcagggggtggggaggggcgggcggcggggctccgg<br>ggctcgcgcatggcgggctgccagtcgcagccatgggagtcgggga<br>gccgggggaggaaggcagctgaggcccgacgagaattcgagcgccga<br>cccggtgggccagcactgctgagggacccggcgcaccctctgcagctgc<br>tggcccgggtgctaagcccctcactgactggtgcggtggcgccggccgg<br>ccgctccaagtgcggggcccgccgagcccacgcccatccggaactcgc<br>gctggccggcgagcacggggcacggcccggttcccgcccg | 321 |
| C5orf49 | GACTCGCAGATCCCATCCCAGGAAATGCACG<br>GGCCGGTGTGGCCAGGACAGAACAGAGGGA<br>CCACTCTCAGTCCAGCCCTCCCTGCAGGCGGC<br>TCGCCAGCTATTCCTTCTGGTCTTCGGTTTGC<br>AGGAGGGCAGAGGGTTTCCCGCGCCCTGGAC<br>CATCCGGGCGTAGTCCCGGCAGCAAGGCCTT<br>CTTTCCTTGCTAGCCTGGGCCTGCCGCAGACA<br>GACCCCAGAGGGAGCGCGCCCAGCCCGCTG<br>GGCGGCCCCGGCTTCCCGCGACCCCCTCCAG<br>ACCCTGGGCAGAAAGAGCGCCCTGCTGTCCC<br>GACAGAGCCACTGTGCTTTTGAGGGATCCTG<br>ACACCTAGTGGCTCCCGCTCCCTTCTCCGAAG<br>AGCACCGGGTCCTATCTGAGCATTCCCGCGA<br>CTCCCAGCCCCTGATCGCAGCTAAGACACCC | 322 |

TABLE 6-continued

Sequences of the DMRs in Table 1

| Marker Region Name | Sequence | SEQ ID NO: |
|---|---|---|
| | ATTCGCGCACCCGGCTTCTCCCACATCCTCGT<br>CCCAGGGGTTCAGCTGACACTGGTAGTCGCC<br>TGAGCTGTACTCTTTGGGGCCCAGGCGCCTTG<br>GCGGGAGCTCACCCTCCCTGTCTCCCCAGCTG<br>ACCCTGCCGCGCCCCCTTCATCTCCGCACGCT<br>CCCACCCGGCCCCCTCCACAGGCTGTCCAGCC<br>CCGCCCCTCGGAAC | |
| MCI | GGGCCTGGTGTCAGTATTCGCGGGCTCTGGC<br>AGCAGTCGGGGCCGCTTGGGATCGCGGCTCT<br>GAAGGGCTTCATCGCAGCGCTCGGAAATCTC<br>CCTCAGGATGGCGTCCACTTCCGCGCAATCCT<br>GCCCCGCAGCGCTGACCAACTCCTCCAGGCT<br>CCTTTTGGCCTTCGCCTTGAGCAGGAAGGGCT<br>CGGCCGCCGCCCCACAATCCCGGGACTGTGT<br>GATCATCAGCTTCTACGAAAGACAGGGAAGA<br>GCGCCGCCCTGGGGCCTGCCGGACCCTC | 323 |
| ANKDD1B | GGCTGACCTGCCTGCGTCCAGCCCCCGCGCCC<br>TGGGCCTGCctgggtctggatctgtgtccgagtctgggtctggatct<br>gggtccgagtctgggtctggCCCTGCGCTCAGGGCCCGC<br>GGAGGAGACTATGGAccccgccgggcgcgcccggggcc<br>AAGGGGCCACGGCAGGGGGGCTGCTGCTCCG<br>GGCTGCTGCGGCCGCCAAGGGTCTCAGGGAA<br>GACCTGTGGGGCGCGGCCGCCCTGCCTTGGA<br>GGAGCCTGTCCCGGATCCCGAAGCGGGAGGG<br>TCTTGGAGAGGAGGACACAGCAGTTGCCGGA<br>CACGAGCTCCGTGAGTCCCGGGACGAGGTCT<br>CAGAAAATCAGGCTGCGGGGCGGGCTGGGTC<br>GAAGGGACTTGAGAAGGTACCCAGAGCAGCA<br>CCTCCGGACGCTGCA | 324 |
| SCGB3A1 | GCGCCCCCGCGGGAGGCGCCCAGGAACCGTC<br>GCGCCCTGCCCGGCTCCCCGACCGCCCCTCCC<br>TCCTGCGCCGAGGCCTGCCAGGTGCGAGCCC<br>CCGGGACACAGGCGGGTCTGGGGAGGCGGCC<br>CCGCCAGGAGACGCTGCAGGGTCACCGGAGT<br>GGCCTGAGGGTGGCGGAAGGACCGGTGAACT<br>CTGTGCAGGGTCCGGGACAGGCCCCCAAGGG<br>AGGGGACACTCGCGCTGCGCCTTGCAGGATG<br>AGGAGCCGGTCTCCAGACGGGGGGCAGACGG<br>GTGTCCCCAGGCCAGGGGCGGCCTCCATCCC<br>GGCACGAGGCTGGAGACAGCCCTGAGAGGG<br>GGAGGCCGCGGGCTGCAGGCGCGGGGCCCCG<br>GGGTGGCGGAGCCCTCTGGGCGCCGGGCGAG<br>GCTGGAAGGACCTGGGATCCACGATCGGCGC<br>AGGCAGCGGCGGGGGCGCAGCGGGCGCCGA<br>GGCCTCAGGCCCCACCGTGCGCGCCAGGAGC<br>CCGGGGCGCTCACCGGAGCTGCAGGACAGGG<br>CCACGCAGAGCCCCAGGAGGGCGGCGAGCTT<br>CATGGCGCGGGGGCTCGGGGCGCGCGGGGAA<br>CCTGCGGCTGCCCGGGCAAGGCCACGAGGCT<br>TCTTATACCCGGTCCTCGCCCCTCCAGCGCCG<br>GCCTCGCCCGCGCTCCTGAGAAAGCCCTGCC<br>CGCTCCGCTCACGGCCGTGCCCTGGCCAACTT<br>CCTGCTGCGGCCGGCGGGCCCTGGGAAGCCC<br>GTGCCCCCTTCCCTGCCCGGGCCTCG | 325 |
| SH2B2 | GGCCTCCCTGCAGGATGTGGCCAGCCCAGGT<br>CCCCACTCACGCCCTGCCGTCGCCTTGTTGCA<br>GAGCCGGGCCCCACGCCCCCTGCCGCGCCCG<br>CGTCCCCGGCCTGCTGGAGCGACTCGCCCGG<br>CCAGCACTACTTCTCCAGCCTCGCCGCGGCCG<br>CCTGCCCGCCTGCCTCGCCCTCCGACGCCGCC<br>GGCGCCTCCTCGTCTTCCGCCTCGTCGTCCTC<br>TGCCGCGTcggggcccgccccccgcgccccgTCGAGGG<br>CCAGCTCAGCGCGCGGAGCCGCAGCAACAGC<br>GCCGAGCGCCTGCTGGAGGCCGTGGCCGCCA<br>CCGCCGCCGAGGAgccccggaggccgcgcccggccgcgc<br>gcgcgccgTGGAGAACCAGTACTCCTTCTACTAG<br>CCCGCGGC | 326 |

TABLE 6-continued

Sequences of the DMRs in Table 1

| Marker Region Name | Sequence | SEQ ID NO: |
|---|---|---|
| MEST; MESTIT1 | GGCAGCTGCGCCTCGCAAGCGCAGTGCCGCA GCGCACGCCGGAGTGGCTGTAGCTgcccggcgcgg cgccgccctgcgcgggcTGTGGGCTGCGGGCTGCGCC CCCGCTGCTGGCCAGCTCTGCACGGCTGCGG GCTCTGCGGCGCCC | 327 |
| TMEM176B; TMEM176A | GCACGCACCCCGAGCTGCCTCCGCACAGTTG GAGGAGCGTAGGAGGGACCCCCACCCAGGG ATGACACTCCAGGAAGGGGACTGCAGAGGAA GCCAGGTGCGGCCCCGGCTTTTGACCTACCTC CGCACCGCAGCGCGGTCCTTCACGGGGCAGG GGCGGCGTGAACCCGTCGGGCGTGAGCAGCA GTCGGTGGAGCGGGAGGTCGGCGGTGGCGGG GATGGGGGTATCCGGAGCGCAGCCGGGGCGC AGCTGCTGGCACAGGAGCTCCACAGGCAGCC AAGGACTCGGTCCTGTCCCAGAGCCTGCGGA CTGTGGAGGGGAGGCCGCAGGAAGAGCCC | 328 |
| KCNH2 | GGGCGATGGGAGCTGGCCGGGCGCGCTGCGG GGCGGAGAGCCGGGACCCACCAGCGCACGCC GCTCCTCCGCGGGCCCGAGCCCTGCCACGTG GTTGTCCATGGCTGTCACTTCGTCCAGGGCCA GCGACTCGCTGCTGGGTGCCGCGGGCGTCAG GTCCACGTCCACCACCAcggccccggggcgcccgcgc cgcccgcgccgcccgACCGCACCGACGACTCCCGGGC | 329 |
| KBTBD11 | GGCCACGGACAGCTGGAGCGCCGTGAGGCCC CTGCGCCAGGCGCGCTCGCAGCTGCGGCTGC TGGCCCTGGACGGTCACCTCTACGCCGTGGG CGGCGAGTGCCTGCTCAGCGTGGAGCGCTAC GAcccgcgcgccgaccgctgggcccccgtggcgccgctgccccggg gcgccTTCGCCGTGGCGCATGAGGCCACCACCT GCCACGGC | 330 |
| INT.chr8_38508331_38508694 | GGCCGCCAGCCCCAGAACAAATGGCGGCTTT CCCGCTGTATTCAGCTAGTCAGCGTTCCCCGG TTAAAAGGCGCTGGGGCAGGAACGGCCGGGG CCTTCGGGGGCGCGACGCGGCGACGCCCAGC CTGGGAAGGGGCGCGGGGCCCGTGTTGGCCG CGGTGGGTCCCGGCTCCCTGGAGGCTGAGCC CCGGGCGCTCTTTCCTCGCGGCGCTGCCGTGG GGTGGCCGGGAGGGCAGAACGAGGGGCTGC GGGACGGTGTTCGGAAGAAAATCGTGCGAGT TTAAAAACATCCAAAGTGAGCCGAGCTGGGC CCCAAGCCTCGGCCTCGCGCACTCGCCAGGC CCAGGAGGCGGAGCAGGCGTC | 331 |
| INT.chr8_48675655_48676143 | GGGAATTAGCGTTTTAGTCTGTTCTGCTAACA ATCGGTGTTTCTCAGTGCCAACCAGTCACAGC ACGCGCGGCGCCCAGCCCCTGGTTTCTAAAC CCCATTCTGTCGTCCCGGGACGAATGTCTTGG GATGTCTGGCTGGGTCCAGGGCAAACATCCT GCAGTGACAAAATGTGTGAAAGTGAAGTTGA GCAACAAGAGGAACAGCATAGCAGCAGATTG TAACCCAACAGATAAAGACATTGTCTGAGTC AATGCGTACAGACCCATTATTCTCCGTGAGG GAAGTGCGCGTCTTCCCTAGCCGCTACTGTCC TCTTTCTGCGCCGCCGGGCTGGGCTCAGTCCG CAGTGACCCAGTCTCGTGTAGGTGGGACCAG CATCTTCACCGGCCGAGGAGACGCCCCTGGA CCACCTGCGTGGGCAGGATCCAGGCAGGCGA CAGGGCTCAGGGCTGCAGCCAAGTCCCCCAG AAACAGTCCCCCTGGGAC | 332 |
| C9orf3 | CTGTGCTTGGAGGAAAGGACGACAGGTTTTA AAGAGGGAGTGTCATCGCCTGCAGCGGGCGG ACCCGTGTCCCGGCAGTGCAGCTCCGCAGGC GCAGGAGGGATGCGGGCTGGGGACGCCTTGG GGCGGCTGCAGGCTGGGGCGCGCCCCTGCAC CCGGCGGGCCTCCGCTGCGTCCACTGCGGAC AGGGGTCGGTGAGAGGCCC | 333 |

TABLE 6-continued

Sequences of the DMRs in Table 1

| Marker Region Name | Sequence | SEQ ID NO: |
|---|---|---|
| C9orf172 | GGGGCCGCGCCGAGAAGACCCGTTGGGCCGC GGCCGCAGCTACGAGAACCTGCTGGGGCGCG AGGTGCGGGAGCCGCGAGGCGTGTCCCCCGA AGGCCGGCGCCCGCCCGTCGTCGTGAACCTG TCCACCTCTCCCAGACGCTACGCC | 334 |
| CLIC3 | GGGTTCTTGATGAACGCGGAGAACTTGTGGA AAACGTCGTTGCCGGCGGTGTTGGACTCCCTG TAACGAGGCGCCAGGCTGGGGAAGCTGCGGG ATGAGGGGGTGGGACTCCATTAGACTGGGGG CAGCCCCGTCCCGGCCCCACAGTACCCCCAC AGCGCCTTCCTGGGCTCTGTCTTGCGCGCGTC CTCCCTGGGCCCCCCTCTTTTCCCCTCCCACC CTGCCGGGGCTCTCACTCGGGCGGCCCCAGC GTCTCCTCCAGAAAGTCCTCGATCTGCAGCGT GTCTGTCTTGGCGTC | 335 |

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for analyzing a plurality of deoxyribonucleic (DNA) molecules from prostate cells in a biological sample obtained from a test subject, and providing a treatment to said test subject, said method comprising:
   (a) providing a first portion of said plurality of DNA molecules, wherein said first portion comprises DNA molecules with methylated and unmethylated cytosines in CpG dinucleotides, and generating fragments by subjecting said first portion to methylation status-dependent fragmentation conditions at one or more CpG sites sufficient to produce fragments of at least a subset of said DNA molecules of said first portion;
   (b) providing a second portion of said plurality of DNA molecules, wherein said second portion is not subjected to said fragmentation conditions;
   (c) for one or more genomic regions, processing: (i) said first portion of said plurality of DNA molecules subjected to said fragmentation conditions, or derivatives thereof, to yield a first quantitative measure of DNA methylation, and (ii) said second portion of said plurality of DNA molecules not subjected to said fragmentation conditions, or derivatives thereof, to yield a second quantitative measure of DNA methylation, wherein said one or more genomic regions include genomic coordinates chr5:74907443-74907561 of the ANKDD1B locus;
   (d) processing said first quantitative measure of DNA methylation with said second quantitative measure of DNA methylation to yield a third quantitative measure of DNA methylation at said one or more genomic regions in said plurality of DNA molecules, thereby generating a methylation profile of said plurality of DNA molecules at said one or more genomic regions;
   (e) processing said methylation profile to indicate a likelihood of said test subject having prostate cancer, wherein processing said methylation profile indicates increased methylation in said genomic region that is chr5:74907443-74907561 in said plurality of DNA molecules as compared to methylation in chr5:74907443-74907561 in a sample obtained from a control subject without prostate cancer, wherein processing said methylation profile indicates an increased likelihood of said test subject having prostate cancer; and
   (f) administering to said test subject a therapeutic intervention for treatment of prostate cancer, wherein said therapeutic intervention comprises a surgical prostate tumor resection, a chemotherapy, a radiotherapy, a targeted therapy, or an immunotherapy.

2. The method of claim 1, wherein said biological sample is obtained or derived from a tissue sample, a blood sample, a plasma sample, a serum sample, an exosome sample, or a urine sample.

3. The method of claim 1, further comprising performing an assay selected from the group consisting of methylation-sensitive restriction enzyme (MSRE) digestion, polymerase chain reaction (PCR), quantitative PCR (qPCR), nucleic acid sequencing, target capture, mass spectrometry-based target fragmentation assay, flap endonuclease-based assay, CRISPR-based assay, methylation-specific assay comprising bisulfite treatment, methylation-specific PCR, targeted sequencing, targeted bisulfite sequencing, pyrosequencing, mass spectroscopy-based bisulfite sequencing (EpiTYPER), reduced representation bisulfite sequence (RRBS), whole genome sequencing (WGS), and a combination thereof.

4. The method of claim 1, wherein said fragmentation conditions comprise MSRE digestion at said one or more CpG sites.

5. The method of claim 4, wherein said MSRE comprises HpaII.

6. The method of claim 1, wherein:
processing said first portion of said plurality of DNA molecules subjected to said fragmentation conditions, or derivatives thereof, in (c) (i) comprises amplification; and
processing said second portion of said plurality of DNA molecules not subjected to said fragmentation conditions, or derivatives thereof, in (c) (ii) comprises amplification.

7. The method of claim 6, wherein:
said amplification comprises targeted quantitative polymerase chain reaction (qPCR) at said one or more genomic regions;
processing said first portion of said plurality of DNA molecules subjected to said fragmentation conditions, or derivatives thereof, in (c) (i) comprises determining a first cycle threshold (Ct) value for amplification of said one or more genomic regions; and
processing said second portion of said plurality of DNA molecules not subjected to said fragmentation conditions, or derivatives thereof, in (c) (ii) comprises determining a second cycle threshold (Ct) value for amplification of said one or more genomic regions.

8. The method of claim 7, wherein (c) comprises:
determining a reference Ct value for amplification of one or more reference genomic regions in said first portion of said plurality of DNA molecules subjected to said fragmentation conditions, or derivatives thereof, and in said second portion of said plurality of DNA molecules not subjected to said fragmentation conditions, or derivatives thereof; and
normalizing said first quantitative measure of DNA methylation and said second quantitative measure of DNA methylation using said reference Ct value.

9. The method of claim 7, wherein processing said first quantitative measure of DNA methylation with said second quantitative measure of DNA methylation in (d) comprises calculating an intensity ratio of said first quantitative measure of DNA methylation and said second quantitative measure of DNA methylation at said one or more genomic regions.

10. The method of claim 1, further comprising subjecting said first portion of said plurality of DNA molecules and said second portion of said plurality of DNA molecules to conditions sufficient to permit methylated nucleic acid bases to be distinguished from unmethylated nucleic acid bases.

11. The method of claim 10, wherein said conditions sufficient to permit methylated nucleic acid bases to be distinguished from unmethylated nucleic acid bases comprise performing bisulfite treatment.

12. The method of claim 1, wherein each of said one or more genomic regions comprises one or more CpG sites.

13. The method of claim 1, further comprising processing said methylation profile with one or more reference methylation profiles obtained from reference biological samples of one or more additional subjects, wherein said one or more additional subjects comprise subjects having prostate cancer.

14. A method for analyzing a plurality of deoxyribonucleic (DNA) molecules from prostate cells in a biological sample obtained from a test subject, and providing a treatment to said test subject, said method comprising:
(a) providing a first portion of said plurality of DNA molecules, wherein said first portion comprises DNA molecules with methylated and unmethylated cytosines in CpG dinucleotides, and generating fragments by subjecting said first portion to methylation status-dependent fragmentation conditions at one or more CpG sites sufficient to produce fragments of at least a subset of said DNA molecules of said first portion;
(b) providing a second portion of said plurality of DNA molecules, wherein said second portion is not subjected to said fragmentation conditions, wherein said second portion has a substantially equal amount of DNA molecules as said first portion;
(c) for one or more genomic regions, processing: (i) said first portion of said plurality of DNA molecules subjected to said fragmentation conditions, or derivatives thereof, to yield a first quantitative measure of DNA methylation and; (ii) said second portion of said plurality of DNA molecules not subjected to said fragmentation conditions, or derivatives thereof, to yield a second quantitative measure of DNA methylation, wherein said one or more genomic regions include genomic coordinates chr5:74907443-74907561 of the ANKDD1B locus;
(d) processing said first quantitative measure of DNA methylation with said second quantitative measure of DNA methylation to yield a third quantitative measure of DNA methylation at said one or more genomic regions in said plurality of DNA molecules, thereby generating a methylation profile of said plurality of DNA molecules at said one or more genomic regions;
(e) processing said methylation profile to indicate a likelihood of said test subject as having prostate cancer, wherein processing said methylation profile indicates increased methylation in said genomic region that is chr5:74907443-74907561 in said plurality of DNA molecules as compared to methylation in chr5:74907443-74907561 in a sample obtained from a control subject without prostate cancer, wherein processing said methylation profile indicates an increased likelihood of said test subject having prostate cancer; and
(f) administering to said test subject a therapeutic intervention for said treatment of prostate cancer, wherein said therapeutic intervention comprises a surgical prostate tumor resection, a chemotherapy, a radiotherapy, a targeted therapy, or an immunotherapy.

15. A method for processing or analyzing a plurality of deoxyribonucleic (DNA) molecules from a biological sample of a subject, comprising:
(a) providing a first portion of said plurality of DNA molecules, wherein said first portion comprises DNA fragments generated upon subjecting at least a subset of said plurality of DNA molecules to fragmentation conditions sufficient to fragment at least a subset of said plurality of DNA molecules at one or more CpG sites, wherein at least a subset of said DNA fragments comprises methylated nucleic acid bases;

(b) providing a second portion of said plurality of DNA molecules, wherein said second portion has a substantially equal amount of DNA as said first portion;

(c) for one or more genomic regions, processing (i) said first portion of said plurality of DNA molecules or derivatives thereof to yield a first quantitative measure of DNA methylation, and (ii) said second portion of said plurality of DNA molecules or derivatives thereof to yield a second quantitative measure of DNA methylation;

(d) processing said first quantitative measure of DNA methylation with said second quantitative measure of DNA methylation to yield a third quantitative measure of DNA methylation at said one or more genomic regions, thereby generating a methylation profile of said plurality of DNA molecules at said one or more genomic regions;

(e) processing said methylation profile to generate a likelihood of said subject having or being suspected of having prostate cancer; and (f) providing a subject that is suspected as having or being suspected of having prostate cancer based on said likelihood with a therapeutic intervention, wherein said therapeutic intervention comprises a surgical tumor resection, an effective dose of chemotherapy, an effective dose of radiotherapy, an effective dose of targeted therapy, or an effective dose of immunotherapy, wherein said one or more genomic regions comprise ANKDD1B with genomic coordinate of chr5: 74907443-74907561.

16. The method of claim 1, wherein said one or more genomic regions further comprise genomic coordinates chr5:180017902-180018673 of the SCGB3A1 locus.

17. The method of claim 1, wherein said one or more genomic regions further comprise genomic coordinates chr5:7850160-7850286 of the C5orf49 locus.

18. The method of claim 1, wherein said one or more genomic regions further comprise genomic coordinates chr9:97807476-97807681 of the C9orf3 locus.

19. The method of claim 1, wherein said one or more genomic regions further comprise genomic coordinates chr2:54086834-54087017 of the GPR75-ASB3 locus.

20. The method of claim 1, wherein processing said methylation profile in (e) comprises using a classifier.

* * * * *

UNITED STATES PATENT AND TRADEMARK OFFICE
CERTIFICATE OF CORRECTION

| | | |
|---|---|---|
| PATENT NO. | : 11,427,874 B1 | |
| APPLICATION NO. | : 16/995180 | |
| DATED | : August 30, 2022 | |
| INVENTOR(S) | : Fang Fang and Neng Yang | |

It is certified that error appears in the above-identified patent and that said Letters Patent is hereby corrected as shown below:

In the Claims

After Claim 13, Line 5:
Insert --14. The method of claim 1, wherein said first portion of said plurality of DNA molecules and said second portion of said plurality of DNA molecules each comprises a first amount of external DNA molecules, wherein said external DNA molecules do not contain CpG sites.--.

Claim 14, Line 1:
Replace "14. A method for analyzing a plurality of deoxyribo-" with --20. A method for analyzing a plurality of deoxyribo- --.

Claim 14, Line 22:
Replace "methylation and; (ii) said second portion of said plu-" with --methylation, and (ii) said second portion of said plu- --.

Claim 14, Line 37:
Replace "lihood of said test subject as having prostate cancer," with --lihood of said test subject having prostate cancer,--.

Claim 14, Line 47:
Replace "vention for said treatment of prostate cancer, wherein" with --vention for treatment of prostate cancer--.

Claim 15, Lines 1 to 41:
Delete entire claim.

Claim 16, Line 1:
Replace "16. The method of claim 1, wherein said one or more" with --15. The method of claim 1, wherein said one or more--.

Signed and Sealed this
Sixteenth Day of May, 2023

Katherine Kelly Vidal
*Director of the United States Patent and Trademark Office*

Claim 17, Line 1:
Replace "17. The method of claim 1, wherein said one or more" with --16. The method of claim 1, wherein said one or more--.

Claim 18, Line 1:
Replace "18. The method of claim 1, wherein said one or more" with --17. The method of claim 1, wherein said one or more--.

Claim 19, Line 1:
Replace "19. The method of claim 1, wherein said one or more" with --18. The method of claim 1, wherein said one or more--.

Claim 20, Line 1:
Replace "20. The method of claim 1, wherein processing said" with --19. The method of claim 1, wherein processing said--.

SEQUENCE LISTING

<160> NUMBER OF SEQ ID NOS: 335

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atatgtggtt gaggaaggaa ttaatact                                      28

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cgactgttag tatcaagggt agaattgtt                                     29

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
acattttaag tggcatctct cttccct                                          27

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gtacgacctg cgttcgttct acattgccg                                        29

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gccggaagca aacctaatgg tttgctaggc tgaatg                                36

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aagagagaat tcgcatacc agtgtccg                                          28

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aatcactgga caaacggacg tatacgttgt atagat                                36

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
taacaaaaat gttaacaccc ggaaattaga t                                     31

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ttggacataa tgattcgtca atcgctaagc ct                                      32

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tatgactcgc aataaacgca a                                                  21

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tttctacttt acgagatgtc gtttggccca c                                       31

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gtcaagcccg agcccgtcat cgctggcctg gtttg                                   35

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ctagaataca acgtggggc                                                     19

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gtaatcactg ccttgtggca gtcaact                                            27

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15

```
caggaagctg ctgatcccgt cgggt                                          25
```

```
<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gagtatccag tttggaggaa ta                                             22

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ctgtatctgt ggacataacg ctaatgcaca atta                                34

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
caacagagac atcttaaaga cacgtgagag gc                                  32

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tgtcgttact tctcagcggc a                                              21

<210> SEQ ID NO 20
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ttgtagtctg tatttataat gtctacgttg ggtgg                               35

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ccactgacac ctaattgct                                                 19
```

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggtagccccc agatggagtc gataacggat g                              31

<210> SEQ ID NO 23
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ttcgacgtaa gatagctgac tcactttgtt cccaaata                       38

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
acaatgattg ttttcgtgcg acatttc                                   27

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ttccttactg gtgcgttgcg gcggctt                                   27

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
atattggtta acagatgtat ttgat                                     25

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cagagcgctt ttaaaagata ggta                                      24

<210> SEQ ID NO 28
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
caggtcgcat tcgcaaactt gacaggcttt cactgac                              37

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tagcttaacg ctaaaacact actcgtgcag cgggc                                35

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ggggtgattc atcgtactga                                                 20

<210> SEQ ID NO 31
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tgacttgact taattagcct acgccgaatg cttgaga                              37

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
aaagtttcat ttctataact c                                               21

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ggcgtcttgc ctaccctaca                                                 20

<210> SEQ ID NO 34
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cgcgatctaa ccacgttcag tgggccctcg aaggtgtg                              38

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tgacctgggc aatcacggtc tat                                              23

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tggcttactg gtctcggtgt gg                                               22

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gtatatagta tcctattg                                                    18

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cagacagtct tctggccaga tgacttaac                                        29

<210> SEQ ID NO 39
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gcacgcacct acaaaccaca ggcgtcacga taaaa                                 35

<210> SEQ ID NO 40

```
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
cacttcatag tacgtctcag tattccgaag gc                                     32

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
aggatatagg ttagtcta                                                     18

<210> SEQ ID NO 42
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tctgtagctt gtgggcggga gcctaaatta caagggca                               38

<210> SEQ ID NO 43
<211> LENGTH: 213
<212> TYPE: DNA
<213> ORGANISM: Homo sapiens

<400> SEQUENCE: 43
cccagaaggc aggtccagga cgcgcccccg cgggaggcgc ccaggaaccg tcgcgccctg        60
cccggctccc cgaccgcccc tccctcctgc gccgaggcct gccaggtgcg agccccggg        120 acacaggcgg gtctggggag gcggccccgc caggagacgc tgcagggtca ccggagtggc       180
ctgagggtgg cggaaggacc ggtgaactct gtg                                    213

<210> SEQ ID NO 44
<211> LENGTH: 18
<212> TYPE: DNA
<213> ORGANISM: Homo sapiens

<400> SEQUENCE: 44
cccagaaggc aggtccag                                                     18

<210> SEQ ID NO 45
<211> LENGTH: 20
<212> TYPE: DNA
<213> ORGANISM: Homo sapiens

<400> SEQUENCE: 45
cacagagttc accggtcctt                                                   20

<210> SEQ ID NO 46
<211> LENGTH: 25
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 46
atgtcggtaa tccatccacc ggaag                                              25

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
aaggtaatac cgagaacttg ggaa                                               24

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ttaaaattgg ttcgatgcct c                                                  21

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
tggtcgccgt tactaaaatt ata                                                23

<210> SEQ ID NO 50
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gtttccggga tatctggtta gtacgcgtcg gg                                      32

<210> SEQ ID NO 51
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
attttgagcc tagaggtagg ttcgct                                             26

<210> SEQ ID NO 52
<211> LENGTH: 35
<212> TYPE: DNA
<213> ORGANISM: Artificial Sequence
<220> FEATURE:
<223> OTHER INFORMATION: Description of Artificial Sequence: Synthetic

```
         oligonucleotide

<400> SEQUENCE: 52
aataggtcaa gggacttaca tcgctcagac tcaga                              35

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
cgagttcctc caagtatc                                                 18

<210> SEQ ID NO 54
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
agtctagcat gaatgcgatc ttcgtccacg aaccta                             36

<210> SEQ ID NO 55
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gctcatcctt gcagtcatag aacgatggat ttag                               34

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ttgatagtgc gttcgttgtt a                                             21

<210> SEQ ID NO 57
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ccgacgtatt actgtattca atgcttatta agg                                33

<210> SEQ ID NO 58
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 58
tcgaggttcg gaaagcgctt ataccatg a                              31

<210> SEQ ID NO 59
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
agtcagctaa acagcgtgat atttaag                                 27

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
agtcccgtaa ttaggtaatt cgtgca                                  26

<210> SEQ ID NO 61
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
aactgccgat caagtgcgca tcatcattcc cc                           32

<210> SEQ ID NO 62
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ccaactgtgc cggcaaactc aagtcaatga gcga                         34

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
cgatcgcgtc caagggttcg aataggt                                 27

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gcgagttata catgaaaacc t                                              21

<210> SEQ ID NO 65
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gtcagatagc tcctgattgt tcgtatccag aggct                               35

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gatccgttca tagtgttagt t                                              21

<210> SEQ ID NO 67
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gagagttcga cgagtaacgg ggagtgcccg g                                   31

<210> SEQ ID NO 68
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ttcgcatata aatatcagac gtaatagatc tttgcaag                            38

<210> SEQ ID NO 69
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ggagtcgcat tgctcctgta gcccgacgta ttggtaga                            38

<210> SEQ ID NO 70
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
aatcatgtga aatatgatcc gcaattgct                                    29

<210> SEQ ID NO 71
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gtagtcaacg tacagcagtc gtaagtcccg t                                 31

<210> SEQ ID NO 72
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
agctccaaag aagtacctat cagtgga                                      27

<210> SEQ ID NO 73
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ctgacaatac gaacatcccg caggtaaagg ca                                32

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
ggtagcctgt tataggaccg                                              20

<210> SEQ ID NO 75
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
atctgacaca ctagagccct cattttgcac taca                              34

<210> SEQ ID NO 76
<211> LENGTH: 112
<212> TYPE: DNA
<213> ORGANISM: Homo sapiens

<400> SEQUENCE: 76
aggacctggg atccacgatc ggcgcaggca gcggcggggg cgcagcgggc gccgaggcct   60
caggccccac cgtgcgcgcc aggagcccgg ggcgctcacc ggagctgcag ga          112

<210> SEQ ID NO 77
<211> LENGTH: 18
<212> TYPE: DNA
<213> ORGANISM: Homo sapiens

<400> SEQUENCE: 77
aggacctggg atccacga                                                18

<210> SEQ ID NO 78
<211> LENGTH: 18
<212> TYPE: DNA
<213> ORGANISM: Homo sapiens

<400> SEQUENCE: 78
tcctgcagct ccggtgag                                                18

<210> SEQ ID NO 79
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gcgatacacg ctgtctcatc gtgac                                        25

<210> SEQ ID NO 80
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ctaaagcgaa tagaagcggc ttcgttaaag cgttg                             35

<210> SEQ ID NO 81
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
cgcttaaacg atagctttac acgtattgct cgatgtag                          38

<210> SEQ ID NO 82
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ctccaaatta gccaataatg gttcacccca ctt                               33

<210> SEQ ID NO 83
<211> LENGTH: 18
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 83
aatgcaaaga atttggcg                                                      18

<210> SEQ ID NO 84
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
atagcgtcgc gaaggtgcgg ttatcagggc catctac                                 37

<210> SEQ ID NO 85
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
cccgtctacg ttaatgtacg tagtctgtca                                         30

<210> SEQ ID NO 86
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gtgctaggac tgccctcga                                                     19

<210> SEQ ID NO 87
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
tctcgtcgca gacattcatt gcccgg                                             26

<210> SEQ ID NO 88
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
aggaaaccat caagcgtgag tggggctgct c                                       31

<210> SEQ ID NO 89
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 89
tactggtccg ccctggatgt aattgaccgt ggtt                         34

<210> SEQ ID NO 90
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gttactctat ttaacccaag cttacta                                 27

<210> SEQ ID NO 91
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
atgggagaga ttgtcgactt gacatttcct ggg                          33

<210> SEQ ID NO 92
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gccatcttca gcggaatttt tagggcata ccgcaa                        36

<210> SEQ ID NO 93
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
ccgctcttac aaccgtacat gaatggt                                 27

<210> SEQ ID NO 94
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
aggcgcccct ctgataaatg catcta                                  26

<210> SEQ ID NO 95
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
tcatcgagtt gtctggaggt catgggggat gca                               33

<210> SEQ ID NO 96
<211> LENGTH: 202
<212> TYPE: DNA
<213> ORGANISM: Homo sapiens

<400> SEQUENCE: 96
actgtgcttg gaggaaagga cgacaggttt taaagaggga gtgtcatcgc ctgcagcggg   60
cggacccgtg tcccggcagt gcagctccgc aggcgcagga gggatgcggg ctggggacgc  120
cttggggcgg ctgcaggctg gggcgcgccc ctgcacccgg cgggcctccg ctgcgtccac  180
tgcggacagg ggtcggtgag ag                                          202

<210> SEQ ID NO 97
<211> LENGTH: 20
<212> TYPE: DNA
<213> ORGANISM: Homo sapiens

<400> SEQUENCE: 97
actgtgcttg gaggaaagga                                              20

<210> SEQ ID NO 98
<211> LENGTH: 18
<212> TYPE: DNA
<213> ORGANISM: Homo sapiens

<400> SEQUENCE: 98
ctctcaccga ccctgtc                                                 18

<210> SEQ ID NO 99
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gcggccacct catcacaaac agactgt                                      27

<210> SEQ ID NO 100
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
tgtagtcccg gttgaagggc cag                                          23

<210> SEQ ID NO 101
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
caggttccga ctctgcgata gcaccggagt acagccag                          38

<210> SEQ ID NO 102
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
gcacgtcaag cgtagggagc ctcgtatact gg                          32

<210> SEQ ID NO 103
<211> LENGTH: 102
<212> TYPE: DNA
<213> ORGANISM: Homo sapiens

<400> SEQUENCE: 103
tgagggtggc ggaaggaccg gtgaactctg tgcagggtcc gggacaggcc cccaagggag    60
gggacactcg cgctgcgcct tgcaggatga ggagccggtc tc                     102

<210> SEQ ID NO 104
<211> LENGTH: 18
<212> TYPE: DNA
<213> ORGANISM: Homo sapiens

<400> SEQUENCE: 104
tgagggtggc ggaaggac                                          18

<210> SEQ ID NO 105
<211> LENGTH: 19
<212> TYPE: DNA
<213> ORGANISM: Homo sapiens

<400> SEQUENCE: 105
gagaccggct cctcatcct                                         19

<210> SEQ ID NO 106
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gtaatctccc tgatggatcg gctggagtat actg                        34

<210> SEQ ID NO 107
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
tccagatgct tactgaagaa atctgcacta tgtg                        34

<210> SEQ ID NO 108
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 108
agaacatgcc cttactaaac ctagcgatgc ctagcga                           37

<210> SEQ ID NO 109
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
tttgtgaaag ccttgtgtgc tcttaccca                                    29

<210> SEQ ID NO 110
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
ggcgaattga cttgctactg gttcttactc acag                              34

<210> SEQ ID NO 111
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
tccacggctt ctctgttcgc tggttac                                      27

<210> SEQ ID NO 112
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
aataatgtag gaagtgtt                                                18

<210> SEQ ID NO 113
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gggtcgtatc cactgttacg acccatttac ttgt                              34

<210> SEQ ID NO 114
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
cgaaccttct ctgctaccga ttgtctaccg gcg                               33

<210> SEQ ID NO 115
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
acactgcctc ttaccgatat acggcaaccg atgt                              34

<210> SEQ ID NO 116
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
aacctctgca atctaatgta ttg                                          23

<210> SEQ ID NO 117
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
ctagtattac gactggttg                                               19

<210> SEQ ID NO 118
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
tatttggcat gctattacgc atatcg                                       26

<210> SEQ ID NO 119
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ttcggctcaa tcgaatacag tcacactagt tcctg                             35

<210> SEQ ID NO 120
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 120
ctaaagctcg agatatgccg ccgcgtcta                                    29

<210> SEQ ID NO 121
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
cggtgactcg tcaggacaaa gagacgtttg tc                                32

<210> SEQ ID NO 122
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ccgaccggta gctctacgta gttctgggca ggatcgac                          38

<210> SEQ ID NO 123
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
cagctaacgc aggctgttag agggttttcc ctagca                            36

<210> SEQ ID NO 124
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
cttcctcctt cttggactac taatgccaa                                    29

<210> SEQ ID NO 125
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
agcaaggtgt catttact                                                18

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
```
caaacaagat tagcttatct                                              20

<210> SEQ ID NO 127
<211> LENGTH: 119
<212> TYPE: DNA
<213> ORGANISM: Homo sapiens

<400> SEQUENCE: 127
ggcccgcgga ggagactatg accccgccg ggcgcgcccg gggccaaggg gccacggcag    60
gggggctgct gctccgggct gctgcggccg ccaagggtct caggaagac ctgtggggc    119

<210> SEQ ID NO 128
<211> LENGTH: 20
<212> TYPE: DNA
<213> ORGANISM: Homo sapiens

<400> SEQUENCE: 128
ggcccgcgga ggagactatg                                              20

<210> SEQ ID NO 129
<211> LENGTH: 20
<212> TYPE: DNA
<213> ORGANISM: Homo sapiens

<400> SEQUENCE: 129
gccccacagg tcttccctga                                              20

<210> SEQ ID NO 130
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
tcttatgcac aactccattg gg                                           22

<210> SEQ ID NO 131
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
ccttctgaga catgacccat tgtcc                                        25

<210> SEQ ID NO 132
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
ctggcgagat gtacgcgtga tgggccggtg                                   30

<210> SEQ ID NO 133
<211> LENGTH: 25
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 133
aggcatccgc tacaaagacg tgaca                                          25

<210> SEQ ID NO 134
<211> LENGTH: 175
<212> TYPE: DNA
<213> ORGANISM: Homo sapiens

<400> SEQUENCE: 134
gcaccaggaa gacaggtacg cggagccggg cctggcccag cgcagccgcg ctcctcgcta   60
tcccgccagc ctccgggagc cgtctccggc atcgtggggt tgtcctcctc caggggcccg  120
cggcctctca cctgccgggt ggccgcagcg ccgcccctcc tccatctcgc agtcc        175

<210> SEQ ID NO 135
<211> LENGTH: 20
<212> TYPE: DNA
<213> ORGANISM: Homo sapiens

<400> SEQUENCE: 135
gcaccaggaa gacaggtacg                                                20

<210> SEQ ID NO 136
<211> LENGTH: 19
<212> TYPE: DNA
<213> ORGANISM: Homo sapiens

<400> SEQUENCE: 136
ggactgcgag atggaggag                                                 19

<210> SEQ ID NO 137
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
ttagttcgag tgggcatgcc tgagg                                          25

<210> SEQ ID NO 138
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
caatcgcgta aaatccattc atcgtgcagg ca                                  32

<210> SEQ ID NO 139
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
```
acaccgggta ggttgctcta gcta                                          24

<210> SEQ ID NO 140
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
ccgccgttgg ccactcaa                                                 18

<210> SEQ ID NO 141
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
cttaagaaat agctgtcgta agttctgaat                                    30

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
agaatgcgta gacaatgccc                                               20

<210> SEQ ID NO 143
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
gaacaacatg agcgcgtcat ataggggtcc gt                                 32

<210> SEQ ID NO 144
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
ttctaccctc atgcgggcc                                                19

<210> SEQ ID NO 145
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
aggctagtac gtgtgggacc ctggcc                                        26

<210> SEQ ID NO 146
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
cctaatcgtt aggccaggcc attctaacaa agaggg                          36

<210> SEQ ID NO 147
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
acagagtgcc attaaactcc aattacagtc cttgta                          36

<210> SEQ ID NO 148
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
ccgagggcct aagcccccgg tcgt                                       24

<210> SEQ ID NO 149
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
tccaatacat attggcaatc ttacatatta tct                             33

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
taagttccgg gaggatgagc                                            20

<210> SEQ ID NO 151
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
cctgacagct tacgaataac atc                                        23

<210> SEQ ID NO 152
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
cgtagttctt ctggatcgcc caacc                                          25

<210> SEQ ID NO 153
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
tacctccctg cagacccata gcccgccgct cgg                                 33

<210> SEQ ID NO 154
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
tcccctcaac gggatattga tcaccgatat ggttaaaa                            38

<210> SEQ ID NO 155
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
atagccatta ttcaattact cgga                                           24

<210> SEQ ID NO 156
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
caataataaa tgccttggca cctaagaaga g                                   31

<210> SEQ ID NO 157
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
ctacggactc catctaggag ggttaatgaa                                     30

```
<210> SEQ ID NO 158
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
acagtacttt tcatatgtcg aatcggagaa tgcat                                   35

<210> SEQ ID NO 159
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
tgacagtcca gaacgctcc                                                     19

<210> SEQ ID NO 160
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
tttccacgta cctacgcgta ccgtttcgtg gcttgc                                  36

<210> SEQ ID NO 161
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
ggtaagaaga atgagggcag ccaatcca                                           28

<210> SEQ ID NO 162
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
ctgaaccatt aaaagcatgt ctttgtgtgg tc                                      32

<210> SEQ ID NO 163
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
tcacactcac tacgtcgacc ggactggtcg acaaatc                                 37

<210> SEQ ID NO 164
```

```
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
aaccgtcacc tcaagaagca gcaagacatc ggtta                               35

<210> SEQ ID NO 165
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
caattgtccg ctgttcaagt tgcatagcac gga                                 33

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
ctcccaaggt accgagggaa t                                              21

<210> SEQ ID NO 167
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
tatatcggaa caatctcact cctgtgccgt ct                                  32

<210> SEQ ID NO 168
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
aggctgacta gtcacgtcgg gttgcc                                         26

<210> SEQ ID NO 169
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
gcgagggttg acatccgg                                                  18

<210> SEQ ID NO 170
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
atgtaaaagc cacctgaagg                                              20

<210> SEQ ID NO 171
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
gttgatattt gagtcaggtc gcac                                         24

<210> SEQ ID NO 172
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
ccacagatta aggacata                                                18

<210> SEQ ID NO 173
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
ttgtggatcc cctgtaatta aggtcggcg                                    29

<210> SEQ ID NO 174
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
ccgatttgag gccgttctga atggccgcgc                                   30

<210> SEQ ID NO 175
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
ggtcgtcatt gtctcgtatc g                                            21

<210> SEQ ID NO 176
<211> LENGTH: 22
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 176
ctggcctaaa aatatataga tg                                        22

<210> SEQ ID NO 177
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
tagatacagt agttggtgt                                            19

<210> SEQ ID NO 178
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
gaggacactg tcatgagtga agtccccggg tta                            33

<210> SEQ ID NO 179
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
taagaagtgt cgaatcaaac ggagtg                                    26

<210> SEQ ID NO 180
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
cttcaagcac cagcatcgcg tagcaagtgt ac                             32

<210> SEQ ID NO 181
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
tgccttttta gtagccggc                                            19

<210> SEQ ID NO 182
<211> LENGTH: 27
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 182
catgagtagc agcgctacga tgactgt                                          27

<210> SEQ ID NO 183
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
actcgccact acgcatcgaa aaccctgagt ggaactca                              38

<210> SEQ ID NO 184
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
ccaaataact attaagagct tccagtatgt acaagc                                36

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
ttgctgtcta accagcttcg                                                  20

<210> SEQ ID NO 186
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
caaggttttg cgagtctact gtcgtcacgt taccttag                              38

<210> SEQ ID NO 187
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
tcgtgttata cacagtttt                                                   19

<210> SEQ ID NO 188
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 188
ggttacgaca gcgatctgg                                                       19

<210> SEQ ID NO 189
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
cccggcgtgt gaggctcacg aaggggg                                              27

<210> SEQ ID NO 190
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
gtataggggt agggaaagct atccag                                               26

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
ccagtttgta ccaagctgtt t                                                    21

<210> SEQ ID NO 192
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
tgagggcgca tagtaacggc atatcacccg tcttgtc                                   37

<210> SEQ ID NO 193
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
tgcgcaaatt acaagtctac acaagtt                                              27

<210> SEQ ID NO 194
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 194
gccggtttgt gttcgcagtg t                                      21

<210> SEQ ID NO 195
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
catagatatc gtcaggactg cggcccgtcg c                           31

<210> SEQ ID NO 196
<211> LENGTH: 119
<212> TYPE: DNA
<213> ORGANISM: Homo sapiens

<400> SEQUENCE: 196
cggtttgcag gagggcagag ggtttcccgc gccctggacc atccgggcgt agtcccggca    60
gcaaggcctt ctttccttgc tagcctgggc ctgccgcaga cagacccag agggagccg    119

<210> SEQ ID NO 197
<211> LENGTH: 20
<212> TYPE: DNA
<213> ORGANISM: Homo sapiens

<400> SEQUENCE: 197
cggtttgcag gagggcagag                                        20

<210> SEQ ID NO 198
<211> LENGTH: 20
<212> TYPE: DNA
<213> ORGANISM: Homo sapiens

<400> SEQUENCE: 198
cggctccctc tggggtctgt                                        20

<210> SEQ ID NO 199
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
tattattaat aagactctag tgtggg                                 26

<210> SEQ ID NO 200
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
ggtcttgaac agacatctac tgcgaatgca ca                          32

<210> SEQ ID NO 201

```
<211> LENGTH: 127
<212> TYPE: DNA
<213> ORGANISM: Homo sapiens

<400> SEQUENCE: 201
cgctcccttc tccgaagagc accgggtcct atctgagcat tcccgcgact cccagcccct      60
gatcgcagct aagacaccca ttcgcgcacc cggcttctcc cacatcctcg tcccaggggt     120
tcagctg                                                              127

<210> SEQ ID NO 202
<211> LENGTH: 21
<212> TYPE: DNA
<213> ORGANISM: Homo sapiens

<400> SEQUENCE: 202
cgctcccttc tccgaagagc a                                               21

<210> SEQ ID NO 203
<211> LENGTH: 20
<212> TYPE: DNA
<213> ORGANISM: Homo sapiens

<400> SEQUENCE: 203
cagctgaacc cctgggacga                                                 20

<210> SEQ ID NO 204
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
cctttgaggt cggggagcta tttcccgtcg c                                    31

<210> SEQ ID NO 205
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
gactggcccg attcgaacac cgtgtacctg tcaact                               36

<210> SEQ ID NO 206
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
ttgagtttga ggctctgaag at                                              22

<210> SEQ ID NO 207
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 207
gagtaggagg tctagtcccc ctagctc    27

<210> SEQ ID NO 208
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
atcggctaca tactgatcgg acagt    25

<210> SEQ ID NO 209
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
ttgtagtatg tcagggggcgg ttggcttgt    29

<210> SEQ ID NO 210
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
ctttgggcgg accggaaccc tcggag    26

<210> SEQ ID NO 211
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
atcacgcata atctaccggg cgtagcaa    28

<210> SEQ ID NO 212
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
ctactcgagg ataggcagag ggccaccgtt ttgtgc    36

<210> SEQ ID NO 213
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 213
gtggcaacgc cgctattgcg gggccgctca cg                                    32

<210> SEQ ID NO 214
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
acgtgccaag ggaactcgcc atg                                              23

<210> SEQ ID NO 215
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
cacccattca tctaaacgtc ttcataa                                          27

<210> SEQ ID NO 216
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
agtacggtac ccttgatccc gacctca                                          27

<210> SEQ ID NO 217
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
aatgggaggt gccgccgtaa c                                                21

<210> SEQ ID NO 218
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
tccgcttgcc ttatggtctc ttccgtgaca tt                                    32

<210> SEQ ID NO 219
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
```
cacgtgtgag tttcttacga gaa                                          23

<210> SEQ ID NO 220
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
gtcgaagctt gagatgccga aaat                                         24

<210> SEQ ID NO 221
<211> LENGTH: 110
<212> TYPE: DNA
<213> ORGANISM: Homo sapiens

<400> SEQUENCE: 221
gctctggatg atgcaggact agaggcatca tcgccatcgc caccgcctcc gcgcatcccg   60
ggagccgcgg caagacgcgg gcgcagaggc gcagtcacgg agacgccgag              110

<210> SEQ ID NO 222
<211> LENGTH: 20
<212> TYPE: DNA
<213> ORGANISM: Homo sapiens

<400> SEQUENCE: 222
gctctggatg atgcaggact                                              20

<210> SEQ ID NO 223
<211> LENGTH: 18
<212> TYPE: DNA
<213> ORGANISM: Homo sapiens

<400> SEQUENCE: 223
ctcggcgtct ccgtgact                                                18

<210> SEQ ID NO 224
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
aaactggtaa gtcccaccta ggcgagagtc ccgact                            36

<210> SEQ ID NO 225
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
gacaagcata tgaaatatga ctgaattgag gtgt                              34

<210> SEQ ID NO 226
<211> LENGTH: 30
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 226
tgaatgtccc gagctcatgg aacgagggat                                     30

<210> SEQ ID NO 227
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
cgttatatcc tctaccgccc gacggggcgg                                     30

<210> SEQ ID NO 228
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
gtcggtggtt acagacatta cac                                            23

<210> SEQ ID NO 229
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
gaacaatata catcgagagc gcaac                                          25

<210> SEQ ID NO 230
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
atagtcaccc cagtagccac tagaatgcta aacctcgg                            38

<210> SEQ ID NO 231
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
tagcctcacg gcataacttt catcaggcgc caatct                              36

<210> SEQ ID NO 232
<211> LENGTH: 30
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 232
gtcattcgcg ggcgaacagt ttacaaacgt                                    30

<210> SEQ ID NO 233
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
atcatagatc gcgatgcgcc tacagtggtg c                                  31

<210> SEQ ID NO 234
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
aaccaccgac tccatagtgc a                                             21

<210> SEQ ID NO 235
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
tcctcatgat ggtcaccagc gagttcgtct gata                               34

<210> SEQ ID NO 236
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
aaggtttcag tggccaatgt ctggtgacc                                     29

<210> SEQ ID NO 237
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
cgtccggatc gtaattgagg c                                             21

<210> SEQ ID NO 238
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 238
gagtgctctg tgcatcttgc gtgagcatgg                                                30

<210> SEQ ID NO 239
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
gggccctgag gagatttggg acaag                                                   25

<210> SEQ ID NO 240
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
tcagggagta ctgtcgttca cgag                                                    24

<210> SEQ ID NO 241
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
cccgacctaa acgtctaggc tacgg                                                   25

<210> SEQ ID NO 242
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
ggagtcactg taagggaagg aatctagtag tc                                           32

<210> SEQ ID NO 243
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
cgcttctgcg tcgaaggaca tgg                                                     23

<210> SEQ ID NO 244
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
ggcttggaga cctatacttg aacg                                          24

<210> SEQ ID NO 245
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
ctagctttac accttattag gtcgtgt                                       27

<210> SEQ ID NO 246
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
tagacacgtg cattagtctc                                               20

<210> SEQ ID NO 247
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247 accccgtta tgtacgtttg ccta                                           24

<210> SEQ ID NO 248
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
agctatgttt tagttcaaga agaggcggat cca                                33

<210> SEQ ID NO 249
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
ttaaatcaag cgactttatt tctttgtta                                     29

<210> SEQ ID NO 250
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 250
aggcctatcc aggcaaggag tgattttcca catgcgg                              37

<210> SEQ ID NO 251
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
gaaaaacagt agggagct                                                  18

<210> SEQ ID NO 252
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
atggtacgtc gtcgcgacgt gaaagcacat ggattt                              36

<210> SEQ ID NO 253
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
tatctacccg gtatgatga                                                 19

<210> SEQ ID NO 254
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
taggaggaaa caagccaaac ttcatgg                                        27

<210> SEQ ID NO 255
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
acgtgagcca agatagcac                                                 19

<210> SEQ ID NO 256
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
```
gtgtaaatca cgcggttctc tgccctggt                                    29

<210> SEQ ID NO 257
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
tggtgttggg ctaccactaa ggaaccccga acagcc                            36

<210> SEQ ID NO 258
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
caagcgataa cgtgctaacc ga                                           22

<210> SEQ ID NO 259
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
gcagtcaaga ggttggtaag cagctgacaa ctacc                             35

<210> SEQ ID NO 260
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
aaattggcag cggaattcca tgttgt                                       26

<210> SEQ ID NO 261
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
cggccgatat ttggtgggtc ctgttcgctc g                                 31

<210> SEQ ID NO 262
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262

```
cgatctctca gagtacgc                                                     18
```

<210> SEQ ID NO 263
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263

```
atgcccccag aaatccgagg gtcagctcgg                                        30
```

<210> SEQ ID NO 264
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264

```
cgcctcacca ctcatagc                                                     18
```

<210> SEQ ID NO 265
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265

```
caacttatat cgcggcaaga ggt                                               23
```

<210> SEQ ID NO 266
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266

```
ctatgcatta ctcctcaccg tt                                                22
```

<210> SEQ ID NO 267
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267

```
gtaggctaaa cgactaatat gcacaccc                                          28
```

<210> SEQ ID NO 268
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268

```
tatacgctct agaattaaag caca                                              24
```

<210> SEQ ID NO 269
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
caagccctgg atcaagcgtg gaatccgtgc aca                                  33

<210> SEQ ID NO 270
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
gcccgttcgc acatagagag ttgaaactaa ggtctg                               36

<210> SEQ ID NO 271
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
caggttaagg gacttacaga ccagggaatc                                      30

<210> SEQ ID NO 272
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
aaatctgccc ctctgataag cggttcccgg t                                    31

<210> SEQ ID NO 273
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
cgcctatagt acacttatta tgctgc                                          26

<210> SEQ ID NO 274
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
ggtagtagcc gtaacacgct aagatt                                          26

```
<210> SEQ ID NO 275
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
tcctgaggat tttcgggatt gaagcccgtg cacta                              35

<210> SEQ ID NO 276
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
caggattctg gacgccacca taactcggcc c                                  31

<210> SEQ ID NO 277
<211> LENGTH: 180
<212> TYPE: DNA
<213> ORGANISM: Homo sapiens

<400> SEQUENCE: 277
ggcccgctgc ccgctgagcc cctcctggcc ttggccgggc cggcagccgc tctcggcccg   60
ctcagccctg gggaggccta cctgaggcag ccgggcttcg cgtcggggct ggagcgctac  120
ctgtgagcct gcgccgcgcg ggcaggcacc tgtgcgacct gtgccccgga cctgcggcgc  180

<210> SEQ ID NO 278
<211> LENGTH: 166
<212> TYPE: DNA
<213> ORGANISM: Homo sapiens

<400> SEQUENCE: 278
ggaggcggaa gcgcgcgagt aggaggtgcg gaggtcgggc tcgcggggct ccgggctgcc   60
cctctgagtg agccgcgctg ctgaagccgg gccctgcgag gcgcccacgg ggccggtgct  120
ggtccctagg gccagagaga agacttctgt ggggtccgct gcgccc                 166

<210> SEQ ID NO 279
<211> LENGTH: 187
<212> TYPE: DNA
<213> ORGANISM: Homo sapiens

<400> SEQUENCE: 279
gggggtgctc agacgctggg ttccaaccgc tggccacctg ggcgggcca aaaaggtgcc   60 tcccttaggg tgacgtgcgg ccgcggggca ttcaggtctc agggatctgc actgggtggg  120
gtggtgagaa ggccggaccc cccacacctc ctaagccgca actgaccgcg aagagcgggc  180
ctcagcg                                                            187

<210> SEQ ID NO 280
<211> LENGTH: 192
<212> TYPE: DNA
<213> ORGANISM: Homo sapiens

<400> SEQUENCE: 280
caactgcgcc ctggacgaca tcgagtggtt tgtggcccgg ctgcagaagg cagccgaggc   60
```

```
tttcaagcag ctgaaccagc ggaaaaaggg gaagaagaag ggcaagaagg cgccagcagg    120 tgcagggac agggacgggg ccggcaggtg caggggacgg ggccagcagg tgcagggac     180 agggacgggg ac                                                         192
```

<210> SEQ ID NO 281
<211> LENGTH: 147
<212> TYPE: DNA
<213> ORGANISM: Homo sapiens

<400> SEQUENCE: 281

```
ggcaccgaag gaggtgaggt tgctccggac ggagctggcg gccaggccga gtagcagcag    60
gcccgcgtag aggacgggcg cgcagtaggg gctgggcgag gagcgcgggc agccggccga   120
ggggcaggca ggtcccagcg gcgacgc                                        147
```

<210> SEQ ID NO 282
<211> LENGTH: 94
<212> TYPE: DNA
<213> ORGANISM: Homo sapiens

<400> SEQUENCE: 282

```
cccggatcgc ggctgggctg ctcgcatggc actgctcggg tacctccggc cgggctccgt    60
cgacgttcgg agcctgctgg cccgtcgggc agct                                94
```

<210> SEQ ID NO 283
<211> LENGTH: 115
<212> TYPE: DNA
<213> ORGANISM: Homo sapiens

<400> SEQUENCE: 283

```
ggagtggggc atgccgtggg agcccacgag ggcctcagcg cggatcctcc gccggaaaac    60
cggctcccgc gagccgccgc cgcaggtttc ctaggccccg cgagtcccgc agcga        115
```

<210> SEQ ID NO 284
<211> LENGTH: 128
<212> TYPE: DNA
<213> ORGANISM: Homo sapiens

<400> SEQUENCE: 284

```
cccctacctg ttgggtttgc gttttaactc cagcgcacac cttgccggca gccctcggag    60
ctaggggagg ggtctcgttt ccccgcagcc cgccggacag acgactgggg cacgggaggg   120
gcggtggc                                                            128
```

<210> SEQ ID NO 285
<211> LENGTH: 130
<212> TYPE: DNA
<213> ORGANISM: Homo sapiens

<400> SEQUENCE: 285

```
aaataaataa ataaataaat aaataaatga ggaacaacta agctggagat agaaacaggg    60 taggggctg gttcttaggc aagagaatga tcacattgaa aaaggctga ggaggatagt    120 atggacgccc                                                          130
```

<210> SEQ ID NO 286
<211> LENGTH: 105
<212> TYPE: DNA
<213> ORGANISM: Homo sapiens

```
<400> SEQUENCE: 286
gtcccggatc agcccccct caccccgctg ggctctggaa ttcccgaggg ggcgccccgg      60
ggtggcggcc gcctgtccgt gctcgggacg ctggggactg agggt                    105

<210> SEQ ID NO 287
<211> LENGTH: 46
<212> TYPE: DNA
<213> ORGANISM: Homo sapiens

<400> SEQUENCE: 287
cggcggcggc tgcggcggcg gcggccgcgg tgtccgcggt gcaccg                    46

<210> SEQ ID NO 288
<211> LENGTH: 47
<212> TYPE: DNA
<213> ORGANISM: Homo sapiens

<400> SEQUENCE: 288
cccggcgccg acggcgcggc cgcccgcaag actcagttcg gcgcctc                   47

<210> SEQ ID NO 289
<211> LENGTH: 236
<212> TYPE: DNA
<213> ORGANISM: Homo sapiens

<400> SEQUENCE: 289
cgccgcggac gcgccgagcc ctctcagtgt ggcgctgccc ggcggcgagg ggggtgtgga    60
acgaagcacg gtcaagacag aaaacaaagt cagcaggtca cctggcaggt tctgggcgaa   120
ttatgcaacg aaagcagggg aatgtttgat gcgtcccact ccacaccccc ccaaccttt    180 tttttttttt ttaagctcct aggaagccgg ttccagttta agggttgggt agggat        236

<210> SEQ ID NO 290
<211> LENGTH: 151
<212> TYPE: DNA
<213> ORGANISM: Homo sapiens

<400> SEQUENCE: 290
gtgcacaggg tctcggcttc tcgtcccagg ggactggggg cggggtgggc gcggagcagg    60
cccggacccc cgcgtggcgc cgcctcagcc cgtgtctctt gcagctcctg ccgctggatg   120
gggaactcgt cctggcttca ggagccggat t                                   151

<210> SEQ ID NO 291
<211> LENGTH: 103
<212> TYPE: DNA
<213> ORGANISM: Homo sapiens

<400> SEQUENCE: 291
ggcgagccca ggcgaggcgc cccaagcctc gggcccaccg acctttcctc ctccgggcga    60
ggccgccgtg ggccaccgcg tggagcgtcg ccctgacgcg ccg                      103

<210> SEQ ID NO 292
<211> LENGTH: 62
<212> TYPE: DNA
<213> ORGANISM: Homo sapiens

<400> SEQUENCE: 292
cgcccaggcc cggggctcca gctccgcccg tcgccgctga aggggtcgga cgccgggcgg    60
gc                                                                    62
```

<210> SEQ ID NO 293
<211> LENGTH: 109
<212> TYPE: DNA
<213> ORGANISM: Homo sapiens

<400> SEQUENCE: 293

```
catgacgatt ttgcaccccc gccagcagtg ccctcggctg acacacctg cgttgtgggc      60 agccggcagc gcgtgaccca ctgtgcacct gcgccttgat gtagggggg               109
```

<210> SEQ ID NO 294
<211> LENGTH: 257
<212> TYPE: DNA
<213> ORGANISM: Homo sapiens

<400> SEQUENCE: 294

```
ccagcccgcg gcctgagggt cccgcccccg ttccccgcac cctcctggcc tgaccccggc      60
ccggcctggc ccgcctggcg ccccacttcc caccctgta agtagcccga ggtcccggct     120
ggggtcttgg gacacccctc caggctgcag cctccaccgt ccctgacgtg cactcactca     180
ggccggacgc cagcgcctgt tcgttggccc acatggccca ctcgatctgc cccatggcga     240
cacgaacccg gctggga                                                    257
```

<210> SEQ ID NO 295
<211> LENGTH: 163
<212> TYPE: DNA
<213> ORGANISM: Homo sapiens

<400> SEQUENCE: 295

```
gggtcccagc ccagaaaagc ggagaccttc ccctccgttt ggaagatgga ctcatcccct      60
acttcctcct ggctccccag aagacctgga gacctcggga agtgttctca tctatgttcg     120
ctccaacccg ggggctcagg cccacctcga tcccgccttc ccg                       163
```

<210> SEQ ID NO 296
<211> LENGTH: 93
<212> TYPE: DNA
<213> ORGANISM: Homo sapiens

<400> SEQUENCE: 296

```
ggggcctccg cgaggccggg cctcgtccgc cgaggccgca gtccggcccc tctcgtcctc      60
ggggcgcggc gcgttcgttt cattaattta tcg                                   93
```

<210> SEQ ID NO 297
<211> LENGTH: 205
<212> TYPE: DNA
<213> ORGANISM: Homo sapiens

<400> SEQUENCE: 297

```
ggccgcggcc tcgcgtcccc gagcccaaca gggctaggag cggggaatgc aggactgcgg      60
aggggcaggg agagacgccc tgagacgcgg agataaacac ccggagacgc cgggagagac     120
ggggagagac gcacacagag acaccaagac acagacacgc aggttgtaga gacaaattca     180
gagacacgag cgaggataga ggcgc                                           205
```

<210> SEQ ID NO 298
<211> LENGTH: 204
<212> TYPE: DNA
<213> ORGANISM: Homo sapiens

```
<400> SEQUENCE: 298
gccaatgggt ccccggcgcc tttccgacgc ccatagcgtg aggacgtgcg aaaatgcgcc      60
ctccagcggc ggttgctccc cgccgcccat gtgcccactg tgggcgaggg cacgggcagt     120
ccggactcac cgtgcggctc ggccgggggc cccgcgggcg cggcggctg ctggtgctgc      180 agtggcgcgg tggcggcgga ggcc                                            204

<210> SEQ ID NO 299
<211> LENGTH: 95
<212> TYPE: DNA
<213> ORGANISM: Homo sapiens

<400> SEQUENCE: 299
gcgcgcctgg cccgcgccta ccgccgctcg cagcgcgcct ccttcaagcg ggcccggcgg      60
ccgggggcgc gcgcgctgcg cctggtgctg ggcat                                 95

<210> SEQ ID NO 300
<211> LENGTH: 147
<212> TYPE: DNA
<213> ORGANISM: Homo sapiens

<400> SEQUENCE: 300
ggtccgtctg gttccctccc aaccccgtc cccgcgcccc ggccgccccc ggttacctgt       60
gcgagtcctg gtctccccccg ggggacgctc ccgccggcgc tcagtacggg cgattggcgt    120
ctttgggccg cttcagctgc accttga                                         147

<210> SEQ ID NO 301
<211> LENGTH: 139
<212> TYPE: DNA
<213> ORGANISM: Homo sapiens

<400> SEQUENCE: 301
gcagccctcg cgtggcgttg ctgcctctgc agatgcctcc ggagggactc ggtgtgtctc      60
ggtgttgatt tcagaacagg ggagatgctg acgtgtcccg gtggctctca cagcacagtg    120
gaaggcgagt ggcagctcc                                                  139

<210> SEQ ID NO 302
<211> LENGTH: 222
<212> TYPE: DNA
<213> ORGANISM: Homo sapiens

<400> SEQUENCE: 302
cccgcgcgga caagcagctt cccagaggcc tcaggaagcc ccgcccgagg gtgtcagctc      60
cagctctgag cgggtcccgc aaacgcccca gcgtgttccc accggtgacc ccgacacccc    120
aacaccccaa cgccccgcac cgccctcagc agccgcgcct tggccagcgg gtgccccggt    180
gcctgcggcc tctgacatag aaaacgagga aggaggcggg cg                        222

<210> SEQ ID NO 303
<211> LENGTH: 301
<212> TYPE: DNA
<213> ORGANISM: Homo sapiens

<400> SEQUENCE: 303
cggggcgacc cgagaaacag gaaaccctgt ttctgagctt cgcaggctct tctgggagac      60
cagcgggtaa tccccttcct ccgacatttc tctgagaagt ctctctgcgt tctgcttctc    120
agaaagaaac cagggtccgg ggcaggcatt cacgccctcc acccactcag gggtttgcag    180
```

-continued

| taacaccctt gggatctgca ggttcacaca gagccagagc cgtgagtcac cgcagccccg | 240 |
| gagctgccgg ggtccccacc tgctcagccc caggaacaca catctacagc gggttccttt | 300 |
| t | 301 |

<210> SEQ ID NO 304
<211> LENGTH: 171
<212> TYPE: DNA
<213> ORGANISM: Homo sapiens

<400> SEQUENCE: 304

| cgccttctgc tcccagcttg gagccccgcg cccacagctt tggcctccgg ttccatcgct | 60 |
| gcccttgtag ggatcctcct cactgtgggc gctgcgtacc tatgcaagtg cctagctatg | 120 |
| aagtcccagg cgtaaagggg gatgttctat gccggctgag cgagaaaaag a | 171 |

<210> SEQ ID NO 305
<211> LENGTH: 298
<212> TYPE: DNA
<213> ORGANISM: Homo sapiens

<400> SEQUENCE: 305

| cccgggaggg gtggggcctg cggccagagc tgcggcttgg tcgcgcagca gccgcaccag | 60 |
| gaagccgatg tacttcatgg ctaggcggag cacctcgttc ttgctcagct tccggtcggg | 120 |
| cgggtgcgtc ggcagcagct tcctcagctc ggcgaaggcg ccgttaacgt tctgctgccg | 180 |
| ccagcgctcc cggctgttgg tgaacacgcg ccgggccacc ttctggggct ggtgccctgt | 240 |
| ggacaaggag ggccgggttg gtgccatggc ccaaagggcg gcccctcctg ccctcccg | 298 |

<210> SEQ ID NO 306
<211> LENGTH: 130
<212> TYPE: DNA
<213> ORGANISM: Homo sapiens

<400> SEQUENCE: 306

| cacggcgggc cccgcacggg cgccgggtgc agcccacaca ccaccagctc cagcacgatc | 60 |
| tgcgccgcct gccgcccggt cagcgccacg cgccagtccc gcagcccgtt gtcggtcatg | 120 |
| aacagctgcc | 130 |

<210> SEQ ID NO 307
<211> LENGTH: 181
<212> TYPE: DNA
<213> ORGANISM: Homo sapiens

<400> SEQUENCE: 307

| ggctgcgcat cgccacggcg tgcaggggc tgggcgtcag aaagggcccg gcgcgggccc | 60 |
| gccgctccgc cgaggagcag gcctccgggc cggcggaccc ccctgccgtc gggtagggcg | 120 |
| ctgagaagga ccgcggcacc gctgcccgcg cgcccaccac ctccggagcg ctgggactgg | 180 |
| c | 181 |

<210> SEQ ID NO 308
<211> LENGTH: 196
<212> TYPE: DNA
<213> ORGANISM: Homo sapiens

<400> SEQUENCE: 308

| gggggggcgcg ggcctggccg acggcttcca ccgctactac ggccccatcg agccgcaggg | 60 |

```
cctaggcctc ggcctgggcg aagcgcgcgc ggcaccgcgg ggcgcagccg ggcgcccgct    120
gtccccgccg gccgctcagc ccccgcagaa gccgccgccc tcctatttcg ccatcgtacg    180
cgacaaggag ccagcc                                                    196
```

<210> SEQ ID NO 309
<211> LENGTH: 398
<212> TYPE: DNA
<213> ORGANISM: Homo sapiens

<400> SEQUENCE: 309

```
gtaagcacag ctcttttgta ctctgttttc cccctaaaga catctgatgc ccccagtgaa     60
gaaaagccaa cagcagcaaa gcctgatgga gagcatgcag cccgggaagc ccagtgactg    120
ggagctggag ggcaggaagc acgagcggcc cgagagcctt ctggaccga cgcagttctg     180 cgcggccgag caggacgtga aggcgctggc cgggcccctg caggccatcc cggagatgga    240
cttcgagtcc tctccggcgg agccgctggg caacgtggag cgctccctgc gcgccccggc    300
cgagctcctg cccgatgccc gcggcttcgt gcccgcggcc tacgaagagt tcgagtacgg    360
cggcgagatc ttcgcgctgc ccgcgcccta cgacgagg                            398
```

<210> SEQ ID NO 310
<211> LENGTH: 312
<212> TYPE: DNA
<213> ORGANISM: Homo sapiens

<400> SEQUENCE: 310

```
caccaggaag acaggtacgc ggagccgggc ctggcccagc gcagccgcgc tcctcgctat     60
cccgccagcc tccgggagcc gtctccggca tcgtggggtt gtcctcctcc aggggcccgc    120
ggcctctcac ctgccgggtg gccgcagcgc cgcccctcct ccatctcgca gtccggaccc    180
cagctccgcc tgccgctctg gatgatgcag gactagaggc atcatcgcca tcgccaccgc    240
ctccgcgcat cccgggagcc gcggcaagac gcgggcgcag aggcgcagtc acggagacgc    300
cgagggcacc gc                                                        312
```

<210> SEQ ID NO 311
<211> LENGTH: 173
<212> TYPE: DNA
<213> ORGANISM: Homo sapiens

<400> SEQUENCE: 311

```
tttggaagcc ccagatccca aatcgacttg cgccgcaacc tccttcccg tcgggacccg      60 ggccgcctgc gcacgccact ccctctcgag cactctctct ctctccctag aggtggagga    120
agacctgggc cgtgctctac ccggccagtc cccacggcgt agcgcggctc gag           173
```

<210> SEQ ID NO 312
<211> LENGTH: 134
<212> TYPE: DNA
<213> ORGANISM: Homo sapiens

<400> SEQUENCE: 312

```
catctcatac ttatctcccg ggcacagctc ggcccctcc cgcagccagc acacgtggcc      60
ccccgagcgg gacacagtca cctccagcac cgccggcgg cccaccagaa cggtcttctc     120
gcgagggggg tggc                                                      134
```

<210> SEQ ID NO 313
<211> LENGTH: 174

```
<212> TYPE: DNA
<213> ORGANISM: Homo sapiens

<400> SEQUENCE: 313
cctttctatg gctgggggcc ggatgaggga cccgggtctg ctcttactcg ccccaagggt      60
ccctgacacc agcccagaac ggggtggagc tggaaagagc ccacacctgc ttcctctgcc     120
cacctcatct cccgcggggc ctctgagacc gcccgggacc cgcttctatc gcgg           174

<210> SEQ ID NO 314
<211> LENGTH: 152
<212> TYPE: DNA
<213> ORGANISM: Homo sapiens

<400> SEQUENCE: 314
gctgcagccc cagggccaag cagcagcggg ccggaagcag cagccacagc gcctgctctg      60
agctggcccg cctctccagc cgcacctcga acaccgtatt gtcgggtgca ggtacagggg     120
ccaccagggc tgtgctgacc gcccggccca gc                                   152

<210> SEQ ID NO 315
<211> LENGTH: 132
<212> TYPE: DNA
<213> ORGANISM: Homo sapiens

<400> SEQUENCE: 315
ggtccatgcg gggctcccca ggcttatcca acgcctcgca ggcgtggctg gcaggagggg      60
cccggccgtg cccagcgccc tcagacgtag ttcttcttgt cgtagtcgcc ggtggccgtg     120
ggccgccgcg gc                                                         132

<210> SEQ ID NO 316
<211> LENGTH: 588
<212> TYPE: DNA
<213> ORGANISM: Homo sapiens

<400> SEQUENCE: 316
acggcgcggg ctcgagcgtg ggggatgcat ccaggccccc ttaccgggga cgctcctcgg      60
agagcagctg cggcgtcgac ggcgactacg aggacgccga gttgaacccc cgcttcctga     120
aggacaacct gatcgacgcc aatggcggta gcaggccccc ttggccgccc ctggagtacc     180
agccctacca gagcatctac gtcggggca tgatggaagg ggagggcaag ggcccgctcc     240
tgcgcagcca gagcacctct gagcaggaga agcgccttac ctggccccgc aggtcctact     300
ccccccggag ttttgaggat tgcggaggcg gctataccc ggactgcagc tccaatgaga      360
acctcacctc cagcgaggag gacttctcct ctggccagtc cagccgcgtg tccccaagcc     420
ccaccaccta ccgcatgttc cgggacaaaa gccgctctcc ctcgcagaac tcgcaacagt     480
ccttcgacag cagcagtccc cccacgccgc agtgccataa gcggcaccgg cactgcccgg     540
ttgtcgtgtc cgaggccacc atcgtgggcg tccgcaagac cgggcaga                 588

<210> SEQ ID NO 317
<211> LENGTH: 75
<212> TYPE: DNA
<213> ORGANISM: Homo sapiens

<400> SEQUENCE: 317
gtgcggggca gggagcgacg gtctggctct agctgggacg cgggcctcgc gtcgggctcg      60
gtgccgtagg agccg                                                      75
```

<210> SEQ ID NO 318
<211> LENGTH: 252
<212> TYPE: DNA
<213> ORGANISM: Homo sapiens

<400> SEQUENCE: 318

```
ggttcgttct caaacaacgc cacctggtag ttgggcatcg gaaacttcag gctccctctg      60
ccgctcgtgc cccgccgggc ccgtcgcgcc ggccccgccc gggcttcggg caagttcggc     120
ggcaggggcg gcgatgggga tggcgacgcg gagggcgtcc ccgcggtggc ggcctccagc     180
gccagtccca cccggacggc gccagccgcg cgccgcaggg cgcacagcag acgcaggcgg     240
accgagccgc cc                                                         252
```

<210> SEQ ID NO 319
<211> LENGTH: 265
<212> TYPE: DNA
<213> ORGANISM: Homo sapiens

<400> SEQUENCE: 319

```
ggcctgtgtg gagcgccctg gactattcct cgcaggccga cccaggtggc acagcccctc      60
ccccggcgcc ggcaccgcca gactcccctc agggcgcaga acggttgccc gggagccagg     120
ggcaaagcgc gcccggggcc aggaagcgca gggactaggc ccgcgcctcc tcggcgccgc     180
ccactgcccc ccgcgagccc aagctccacg gccaccgccc gcgccctccc ggggactccg     240
gcgccccgtc cgcccctcgg cctcg                                           265
```

<210> SEQ ID NO 320
<211> LENGTH: 224
<212> TYPE: DNA
<213> ORGANISM: Homo sapiens

<400> SEQUENCE: 320

```
gcgcgctgct ggtcgtggtg ctgcgcacgc cgggactgcg cgacgcgctc tacctggcgc      60
acctgtgcgt cgtggacctg ctggcggccg cctccatcat gccgctgggc ctgctggccg     120
caccgccgcc cgggctgggc cgcgtgcgcc tgggccccgc gccatgccgc gccgctcgct     180
tcctctccgc cgctctgctg ccggcctgca cgctcggggt ggcc                      224
```

<210> SEQ ID NO 321
<211> LENGTH: 327
<212> TYPE: DNA
<213> ORGANISM: Homo sapiens

<400> SEQUENCE: 321

```
ccgcggagca gggggtgggg aggggcgggg gcggcggggc tccggggctc gcgcatggcg      60
ggctgccagt cgccagccat gggagtcggg ggagccgggg gaggaaggca gctgaggccc     120
gacgagaatt cgagcgccga cccggtgggc cagcactgct gagggacccg cgcacccctc     180
tgcagctgct ggccccgggtg ctaagcccct cactgactgg tgcggtggcg ccggccggcc    240
gctccaagtg cggggcccgc cgagcccacg cccatccgga actcgcgctg gccggcgagc     300
acggggcacg gccccggttc ccgcccg                                         327
```

<210> SEQ ID NO 322
<211> LENGTH: 642
<212> TYPE: DNA
<213> ORGANISM: Homo sapiens

<400> SEQUENCE: 322

```
gactcgcaga tcccatccca ggaaatgcac gggccggtgt ggccaggaca gaacagaggg      60
accactctca gtccagccct ccctgcaggc ggctcgccag ctattccttc tggtcttcgg     120
tttgcaggag ggcagagggt ttcccgcgcc ctggaccatc cgggcgtagt cccggcagca     180
aggccttctt tccttgctag cctgggcctg ccgcagacag accccagagg gagccgcgcc     240
cagcccgctg ggcggccccg gcttcccgcg accccctcca gaccctgggc agaaagagcg     300
ccctgctgtc ccgacagagc cactgtgctt ttgagggatc ctgacaccta gtggctcccg     360
ctcccttctc cgaagagcac cgggtcctat ctgagcattc ccgcgactcc cagcccctga     420
tcgcagctaa gacacccatt cgcgcacccg gcttctccca catcctcgtc ccaggggttc     480
agctgacact ggtagtcgcc tgagctgtac tctttgggc ccaggcgcct tggcgggagc     540
tcaccctccc tgtctcccca gctgaccctg ccgcgccccc ttcatctccg cacgctccca     600
cccggccccc tccacaggct gtccagcccc gcccctcgga ac                        642
```

```
<210> SEQ ID NO 323
<211> LENGTH: 278
<212> TYPE: DNA
<213> ORGANISM: Homo sapiens

<400> SEQUENCE: 323
gggcctggtg tcagtattcg cgggctctgg cagcagtcgg ggccgcttgg gatcgcggct      60
ctgaagggct tcatcgcagc gctcggaaat ctccctcagg atggcgtcca cttccgcgca     120
atcctgcccc gcagcgctga ccaactcctc caggctcctt ttggccttcg ccttgagcag     180
gaagggctcg gccgccgccc cacaatcccg ggactgtgtg atcatcagct tctacgaaag     240
acagggaaga gcgccgccct ggggcctgcc ggaccctc                             278
```

```
<210> SEQ ID NO 324
<211> LENGTH: 419
<212> TYPE: DNA
<213> ORGANISM: Homo sapiens

<400> SEQUENCE: 324
ggctgacctg cctgcgtcca gccccgcgc cctgggcctg cctgggtctg gatctgtgtc       60
cgagtctggg tctggatctg gtccgagtc tgggtctggc cctgcgctca gggcccgcgg     120
aggagactat ggaccccgcc gggcgcgccc ggggccaagg ggccacggca gggggggctgc   180 tgctccgggc tgctgcggcc gccaagggtc tcagggaaga cctgtgggc gcggccgccc    240 tgccttggag gagcctgtcc cggatcccga agcggaggg tcttggagag gaggacacag     300
cagttgccgg acacgagctc cgtgagtccc ggacgaggt ctcagaaaat caggctgcgg    360
ggcgggctgg gtcgaaggga cttgagaagg tacccagagc agcacctccg gacgctgca     419
```

```
<210> SEQ ID NO 325
<211> LENGTH: 771
<212> TYPE: DNA
<213> ORGANISM: Homo sapiens

<400> SEQUENCE: 325 gcgccccgc gggaggcgcc caggaaccgt cgcgccctgc ccggctcccc gaccgcccct       60
ccctcctgcg ccgaggcctg ccaggtgcga gccccggga cacaggcggg tctggggagg    120
cggccccgcc aggagacgct gcagggtcac cggagtggcc tgagggtggc ggaaggaccg    180
gtgaactctg tgcagggtcc gggacaggcc cccaagggag gggacactcg cgctgcgcct    240
```

-continued

| | |
|---|---|
| tgcaggatga ggagccggtc tccagacggg gggcagacgg gtgtccccag gccaggggcg | 300 |
| gcctccatcc cggcacgagg ctggagacag ccctgagagg gggaggccgc gggctgcagg | 360 |
| cgcggggccc cggggtggcg gagccctctg ggcgccgggc gaggctggaa ggacctggga | 420 |
| tccacgatcg gcgcaggcag cggcgggggc gcagcgggcg ccgaggcctc aggccccacc | 480 |
| gtgcgcgcca ggagcccggg gcgctcaccg gagctgcagg acagggccac gcagagcccc | 540 |
| aggagggcgg cgagcttcat ggcgcggggg ctcggggcgc gcggggaacc tgcggctgcc | 600 |
| cgggcaaggc cacgaggctt cttatacccg gtcctcgccc ctccagcgcc ggcctcgccc | 660 |
| gcgctcctga gaaagccctg cccgctccgc tcacggccgt gccctggcca acttcctgct | 720 |
| gcggccggcg ggcctgggga agcccgtgcc cccttccctg cccgggcctc g | 771 |

<210> SEQ ID NO 326
<211> LENGTH: 404
<212> TYPE: DNA
<213> ORGANISM: Homo sapiens

<400> SEQUENCE: 326

| | |
|---|---|
| ggcctccctg caggatgtgg ccagcccagg tccccactca cgccctgccg tcgccttgtt | 60 |
| gcagagccgg gccccacgcc ccctgccgcg cccgcgtccc cggcctgctg gagcgactcg | 120 |
| cccggccagc actacttctc cagcctcgcc gcggccgcct gccgcctgc ctcgccctcc | 180 |
| gacgccgccg gcgcctcctc gtcttccgcc tcgtcgtcct ctgccgcgtc ggggcccgcc | 240 |
| cccccgcgcc ccgtcgaggg ccagctcagc gcgcggagcc gcagcaacag cgccgagcgc | 300 |
| ctgctggagg ccgtggccgc caccgccgcc gaggagcccc cggaggccgc gcccggccgc | 360 |
| gcgcgcgccg tggagaacca gtactccttc tactagcccg cggc | 404 |

<210> SEQ ID NO 327
<211> LENGTH: 148
<212> TYPE: DNA
<213> ORGANISM: Homo sapiens

<400> SEQUENCE: 327

| | |
|---|---|
| ggcagctgcg cctcgcaagc gcagtgccgc agcgcacgcc ggagtggctg tagctgcccg | 60 |
| gcgcggcgcc gccctgcgcg ggctgtgggc tgcgggctgc gccccgctg ctggccagct | 120 |
| ctgcacggct gcgggctctg cggcgccc | 148 |

<210> SEQ ID NO 328
<211> LENGTH: 339
<212> TYPE: DNA
<213> ORGANISM: Homo sapiens

<400> SEQUENCE: 328

| | |
|---|---|
| gcacgcaccc cgagctgcct ccgcacagtt ggaggagcgt aggagggacc cccacccagg | 60 |
| gatgacactc caggaagggg actgcagagg aagccaggtg cggccccggc ttttgaccta | 120 |
| cctccgcacc gcagcgcggt ccttcacggg gcaggggcgg cgtgaacccg tcgggcgtga | 180 |
| gcagcagtcg gtggagcggg aggtcggcgg tggcggggat gggggtatcc ggagcgcagc | 240 |
| cggggcgcag ctgctggcac aggagctcca caggcagcca aggactcggt cctgtcccag | 300 |
| agcctgcgga ctgtggaggg gaggccgcag gaagagccc | 339 |

<210> SEQ ID NO 329
<211> LENGTH: 231
<212> TYPE: DNA
<213> ORGANISM: Homo sapiens

<400> SEQUENCE: 329

```
gggcgatggg agctggccgg gcgcgctgcg gggcggagag ccgggaccca ccagcgcacg    60
ccgctcctcc gcgggcccga gccctgccac gtggttgtcc atggctgtca cttcgtccag   120
ggccagcgac tcgctgctgg gtgccgcggg cgtcaggtcc acgtccacca ccacggcccc   180
cggggcgccc gcgccgcccg cgccgcccga ccgcaccgac gactcccggg c            231
```

<210> SEQ ID NO 330
<211> LENGTH: 211
<212> TYPE: DNA
<213> ORGANISM: Homo sapiens

<400> SEQUENCE: 330

```
ggccacggac agctggagcg ccgtgaggcc cctgcgccag gcgcgctcgc agctgcggct    60
gctggccctg acggtcacc tctacgccgt gggcggcgag tgcctgctca gcgtggagcg   120
ctacgacccg cgcgccgacc gctgggcccc cgtggcgccg ctgccccggg gcgccttcgc   180
cgtggcgcat gaggccacca cctgccacgg c                                  211
```

<210> SEQ ID NO 331
<211> LENGTH: 363
<212> TYPE: DNA
<213> ORGANISM: Homo sapiens

<400> SEQUENCE: 331

```
ggccgccagc cccagaacaa atggcggctt tcccgctgta ttcagctagt cagcgttccc    60
cggttaaaag gcgctggggc aggaacggcc ggggccttcg ggggcgcgac gcggcgacgc   120
ccagcctggg aaggggcgcg gggcccgtgt tggccgcggt gggtcccggc tccctggagg   180
ctgagccccg ggcgctcttt cctcgcggcg ctgccgtggg gtggccggga gggcagaacg   240
aggggctgcg ggacggtgtt cggaagaaaa tcgtgcgagt ttaaaaacat ccaaagtgag   300
ccgagctggg ccccaagcct cggcctcgcg cactcgccag gcccaggagg cggagcaggc   360
gtc                                                                 363
```

<210> SEQ ID NO 332
<211> LENGTH: 488
<212> TYPE: DNA
<213> ORGANISM: Homo sapiens

<400> SEQUENCE: 332

```
gggaattagc gttttagtct gttctgctaa caatcggtgt ttctcagtgc caaccagtca    60
cagcacgcgc ggcgcccagc ccctggtttc taaacccat tctgtcgtcc cgggacgaat    120
gtcttgggat gtctggctgg gtccagggca aacatcctgc agtgacaaaa tgtgtgaaag   180
tgaagttgag caacaagagg aacagcatag cagcagattg taacccaaca gataaagaca   240
ttgtctgagt caatgcgtac agacccatta ttctccgtga gggaagtgcg cgtcttccct   300
agccgctact gtcctctttc tgcgccgccg ggctgggctc agtccgcagt gacccagtct   360
cgtgtaggtg ggaccagcat cttcaccggc cgaggagacg cccctggacc acctgcgtgg   420
gcaggatcca ggcaggcgac agggctcagg gctgcagcca gtcccccag aaacagtccc   480
cctgggac                                                            488
```

<210> SEQ ID NO 333
<211> LENGTH: 205
<212> TYPE: DNA

```
<213> ORGANISM: Homo sapiens

<400> SEQUENCE: 333
ctgtgcttgg aggaaaggac gacaggtttt aaagagggag tgtcatcgcc tgcagcgggc      60
ggacccgtgt cccggcagtg cagctccgca ggcgcaggag ggatgcgggc tggggacgcc     120
ttggggcggc tgcaggctgg ggcgcgcccc tgcacccggc gggcctccgc tgcgtccact     180
gcggacaggg gtcggtgaga ggccc                                           205

<210> SEQ ID NO 334
<211> LENGTH: 148
<212> TYPE: DNA
<213> ORGANISM: Homo sapiens

<400> SEQUENCE: 334
ggggccgcgc cgagaagacc cgttgggccg cggccgcagc tacgagaacc tgctggggcg      60
cgaggtgcgg gagccgcgag gcgtgtcccc cgaaggccgg cgcccgcccg tcgtcgtgaa     120
cctgtccacc tctcccagac gctacgcc                                        148

<210> SEQ ID NO 335
<211> LENGTH: 298
<212> TYPE: DNA
<213> ORGANISM: Homo sapiens

<400> SEQUENCE: 335
gggttcttga tgaacgcgga gaacttgtgg aaaacgtcgt tgccggcggt gttggactcc      60
ctgtaacgag gcgccaggct gggggaagctg cgggatgagg gggtgggact ccattagact    120
gggggcagcc ccgtcccggc cccacagtac ccccacagcg ccttcctggg ctctgtcttg     180
cgcgcgtcct ccctgggccc ccctctttc ccctcccacc ctgccgggc tctcactcgg      240 gcggcccag cgtctcctcc agaaagtcct cgatctgcag cgtgtctgtc ttggcgtc       298
```